(12) United States Patent
Barth et al.

(10) Patent No.: US 7,361,687 B2
(45) Date of Patent: Apr. 22, 2008

(54) ARYLSULPHONAMIDE DERIVATIVES AND METHODS OF PREPARING

(75) Inventors: Martine Barth, Asnieres les Dijon (FR); Michel Bondoux, Fontaine les Dijon (FR); Pierre Dodey, Fontaine les Dijon (FR); Christine Massardier, Dijon (FR); Jean-Michel Luccarini, Dijon (FR)

(73) Assignee: Laboratoires Fournier SA (FR)

( * ) Notice: Subject to any disclaimer, the term of this patent is extended or adjusted under 35 U.S.C. 154(b) by 566 days.

(21) Appl. No.: 10/517,909

(22) PCT Filed: Jun. 12, 2003

(86) PCT No.: PCT/FR03/01763

§ 371 (c)(1),
(2), (4) Date: Dec. 9, 2004

(87) PCT Pub. No.: WO03/106428

PCT Pub. Date: Dec. 24, 2003

(65) Prior Publication Data

US 2006/0084699 A1   Apr. 20, 2006

(30) Foreign Application Priority Data

Jun. 14, 2002 (FR) .................... 02 07387

(51) Int. Cl.
*C07D 233/54* (2006.01)
*C07D 239/06* (2006.01)
*C07D 409/12* (2006.01)

(52) U.S. Cl. .............. 514/604; 514/360; 514/310; 514/183

(58) Field of Classification Search .......... 514/310
See application file for complete search history.

(56) References Cited

U.S. PATENT DOCUMENTS 6,015,812 A * 1/2000 Ferrari et al. ............. 514/235.8

2004/0063725 A1 * 4/2004 Barth et al. ............. 514/255.01

FOREIGN PATENT DOCUMENTS

| EP | 0236 164 B1 | 9/1990 |
|---|---|---|
| EP | 0 236 163 B1 | 10/1990 |
| EP | 0558 961 A2 | 9/1993 |
| EP | 0 614 911 B1 | 4/1999 |
| WO | WO 92/16549 A1 | 10/1992 |
| WO | WO 96/40639 | 12/1996 |
| WO | WO 97/24349 | 7/1997 |
| WO | WO 97/25315 | 7/1997 |
| WO | WO 98/03503 | 1/1998 |
| WO | WO 98/24783 | 6/1998 |
| WO | WO 99/00387 | 1/1999 |
| WO | WO 00/34313 | 6/2000 |
| WO | WO 00/75107 A2 | 12/2000 |
| WO | WO 02/076964 A1 | 10/2002 |

OTHER PUBLICATIONS

Dutta, A.S. et al., "Inhibitors of Porcine Pancreatic Elastase. Peptides Incorporating α-Aza-amino Acid Residues in the P1 Position", *Journal of the Chemical Society*, Perkin Transactions 1, 1986, 9, 1655-1664.
Shibata, M. et al., "Modified Formalin Test: Characteristic Biphasic Pain Response", *Pain*, 38, 347-352, (1989).

* cited by examiner

*Primary Examiner*—Ardin H. Marschel
*Assistant Examiner*—Meghan Finn
(74) *Attorney, Agent, or Firm*—Woodcock Washburn LLP

(57) ABSTRACT

The present invention relates to novel arylsulphonamide compounds, defined by formula I and the description, as well as their method of preparation and their therapeutic use

21 Claims, No Drawings

ARYLSULPHONAMIDE DERIVATIVES AND METHODS OF PREPARING

CROSS-REFERENCE TO RELATED APPLICATIONS

This application is the National Stage of International Application No. PCT/FR03/01763, filed Jun. 12, 2003, which claims priority to French Patent Application No. 02 07387, filed Jun. 14, 2002, the entire disclosures of which are incorporated herein by reference.

The present invention relates to novel compounds of arylsulphonamide type, their method of preparation and their use to obtain pharmaceutical compositions.

These new compounds can be given therapeutic use, especially to treat pain.

PRIOR ART

Compounds are already known whose structure includes a group of arylsulphonamide type. For example, through EP 236 163 and EP 236 164, N-α-arylsulphonylaminoacyl-p-amidino-phenyl-alaninamide derivatives may be cited which are selective inhibitors of thrombin and can be used as anti-thrombotics. Also, according to EP 614 911, compounds are known whose structure is fairly close to the preceding compounds, simultaneously comprising an arylsulphamoyl group and a substituted phenylamidine group, which have the property of binding onto the receptors of the Y neuropeptide and which may be used to treat hypertension, angina pectoris, atherosclerosis, depression, anxiety, inflammation, allergy or excess fat.

EP 558 961 also suggests the use of arylsulphonamide-type compounds of substituted amino acids for the treatment of thrombosis on account of their anticoagulant properties. Studies on the antithrombotic properties of compounds whose structure includes an arylsulphonamide group and a phenylamidine group, have also been published in Pharmazie 1984 vol. 39 (5) pages 315-317 and Pharmazie 1986 vol. 41 (4) p 233-235.

In the same area of pharmacological activity, WO 92/16549 A1 describes derivatives of phenylalanine comprising an arylsulphonamide group, which are proteinase inhibitors, in particular thrombin inhibitors.

Compounds are also known, from WO 97/25315, having N-(arylsulphonyl)amino-acid structure, which can be used to treat inflammatory diseases.

In a different therapeutic domain, WO 00/34313 describes peptides which may have an end-chain arylsulphonyl group and which are claimed for their ability to inhibit procollagen-C-proteinase. Also, through the publication in J. Chem. Soc., Perkin Trans. 1(1986), (9) p 1655-64 compounds are known with closely similar structure which are presented as inhibitors of porcine pancreatic elastase.

Among the prior art documents proposing elements with a structure of arylsulphonamide type, mention may be made of WO 96/40639, WO 97/24349, WO 98/03503, WO 98/24783 and WO 99/00387, pertaining to antagonist compounds of the $B_2$ receptor of bradykinin.

OBJECT OF THE INVENTION

The invention concerns novel compounds comprising the substituted arylsulphonamide chain, said compounds being useful in particular as active ingredients for medicinal products intended to treat pain, in particular hyperalgesia and major algesia.

DESCRIPTION

According to the present invention, as a novel industrial product, an arylsulphonamide compound is proposed, characterized in that it chosen from among the group formed by:
i) compounds having the formula:

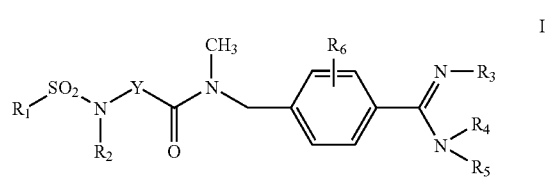

in which
$R_1$ represents a aromatic system which is non-substituted or substituted by one or more atoms or groups of atoms chosen from among halogens, $C_1$-$C_3$ alkyl groups, $C_1$-$C_3$ alcoxy groups, nitro, cyano, trifluoromethyl or trifluoromethoxy,
$R_2$ represents a hydrogen atom or a $C_1$-$C_4$ alkyl group optionally substituted by a phenyl group, by a $CONH_2$ group or by one or more fluorine atoms,
$R_3$ represents a hydrogen atom, a hydroxy group, or with $R_4$ forms a —CH=N— group or a straight or branched $C_2$-$C_4$ alkylene group,
$R_4$ represents a hydrogen atom or with $R_3$ forms a —CH=N— group or a straight or branched $C_2$-$C_4$ alkylene group,
$R_5$ represents a hydrogen atom or a $C_1$-$C_3$ alkyl group,
$R_6$ represents a hydrogen atom or a halogen,
Y represents a $C_2$-$C_4$ alkylene group that is saturated or unsaturated, straight or branched, optionally interrupted between two carbon atoms by an oxygen atom,
ii) the addition salts of the above formula I compounds with an acid.

According to the invention, a method is also advocated for preparing compounds having formula I and their addition salts.

The use is also proposed of a substance chosen from among the formula I compounds and their non-toxic addition salts, to prepare a medicinal product which can be used for human or animal therapy intended for the prevention or treatment of pain-related pathologies, in particular hyperalgesia subsequent to an inflammatory condition, or major algesia related to other pathologies such as cancer for example.

DETAILED DESCRIPTION

In formula I, by $C_1$-$C_4$ alkyl group is meant a hydrocarbon chain having 1 to 4 carbon atoms, whether straight, branched or cyclic. Said group is in particular a methyl, ethyl, propyl, butyl, 1-methyl-ethyl, 1-methylpropyl, 2-methylpropyl, 1,1-dimethylethyl, cyclopropyl and cyclopropylmethyl group.

By $C_1$-$C_4$ alkyl group substituted by a phenyl group is meant a $C_1$-$C_4$ alkyl group of which one of the hydrogen atoms is replaced by a phenyl group. Said group is in particular a phenylmethyl group, a 2-(phenyl)-ethyl group, a 1-(phenyl)ethyl group, a phenylpropyl group or a phenylbutyl group.

By $C_1$-$C_4$ alkyl group substituted by a $CONH_2$ group is meant a $C_1$-$C_4$ alkyl group of which one of the carbon atoms is replaced by a $CONH_2$ group. Said group may, for example, be a —CH$_2$—CONH$_2$ group, a —(CH$_2$)$_2$—CONH$_2$ group, —CH(CH$_3$)—CH$_2$—CONH$_2$ group or still further a —(CH$_2$)$_4$—CONH$_2$ group.

By halogen is meant an atom of fluorine, chlorine or bromine, and preferably a fluorine or chlorine atom.

By aromatic system is meant a phenyl system, a 1- or 2-naphthyl system or a 2- or 3-thienyl system.

By C$_1$-C$_3$ alkoxy group is meant an OR group in which R is a C$_1$-C$_3$ alkyl group, the term alkyl having the denotation given above. Said group is for example a methoxy, ethoxy, propoxy or 1-methylethoxy group.

By saturated C$_2$-C$_4$ alkylene group is meant a —(CH$_2$)$_n$— group in which n is 2, 3 or 4 if it is a straight-chain group, or for example a —CH(CH$_3$)—CH$_2$—CH$_2$— or —C(CH$_3$)$_2$—CH$_2$— group if it is a branched group. By alkylene group interrupted by an oxygen atom is meant for example the groups —CH$_2$—CH$_2$—O—CH$_2$—, —CH$_2$—O—CH$_2$—CH$_2$— or —CH$_2$—CH$_2$—O—CH$_2$—CH$_2$—. By unsaturated C$_2$-C$_4$ alkylene group is meant a group comprising 2 to 4 carbon atoms of which 2 consecutive atoms are bound by an ethylene bond, for example the groups —CH$_2$—CH=CH—CH$_2$—, —CH=CH—CH$_2$—, —CH=C(CH$_3$)—CH$_2$—, CH$_2$—CH=CH— or —CH=CH—CH(CH$_3$)—.

By addition salts is meant addition salts obtained by reaction of a formula 1 compound, containing at least one base function in its non-salified form, with a mineral or organic acid. Preferably, these are pharmaceutically acceptable salts.

Among the mineral acids suitable for salifying a formula 1 base compound, preference is given to hydrochloric, hydrobromic, phosphoric and sulphuric acids. Among the organic acids suitable for salifying a base compound of formula 1, preference is given to methanesulphonic, benzenesulphonic, toluenesulphonic, maleic, fumaric, oxalic, citric, tartaric, lactic and trifluoroacetic acids.

According to one preferred aspect, the subject of the invention is compounds of formula:

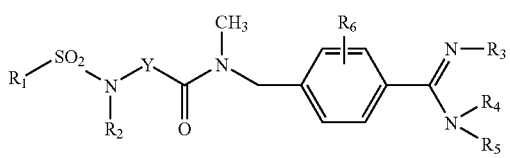

Ia in which

R$_1$, R$_2$, R$_5$, R$_6$ and Y are as defined for the compounds of formula I,

R$_3$ represents a hydrogen atom, a hydroxy group, or with R$_4$ forms an C$_2$-C$_4$ alkylene group, straight or branched, R$_4$ represents a hydrogen atom or with R$_3$ forms a C$_2$-C$_4$ straight or branched alkylene group.

Among the compounds of fomula I or Ia, preference is given to those in which R$_1$ represents a phenyl ring substituted by one or more atoms or groups, of atoms chosen from among a halogen atom, preferably chlorine, and the C$_1$-C$_3$ alkyl groups and C$_1$-C$_3$ alkoxy groups.

Preference is also given to:
those in which R$_2$ represents a C$_1$-C$_4$ alkyl group;
those in which R$_3$ et R$_4$ together form a C$_2$-C$_3$ alkylene group;
those in which R$_5$ et R$_6$ each represent a hydrogen atom; and those in which Y represents a saturated C$_2$-C$_4$ alkylene chain, optionally interrupted by an oxygen atom, in particular a —(CH$_2$)$_4$— group or a —(CH$_2$)$_2$—O—CH$_2$— group.

According to the invention, a general method is proposed for preparing compounds of their invention and their addition salts, comprising the steps consisting of:

1) reacting an acid of formula:

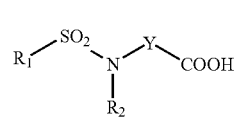

II in which

R$_1$ represents an aromatic system that is non-substituted or substituted by one or more atoms or groups of atoms chosen from among the halogens, C$_1$-C$_3$, alkyl groups, C$_1$-C$_3$ alkoxy groups, nitro, cyano, trifluoromethyl or trifluoromethoxy, R$_2$ represents a hydrogen atom, a C$_1$-C$_4$ alkyl group optionally substituted by a phenyl group, by a CONH$_2$ group or by one or more fluorine atoms, and Y represents a saturated or unsaturated C$_2$-C$_4$ alkylene group, straight or branched, optionally interrupted between two carbon atoms by an oxygen atom, with an amine of formula:

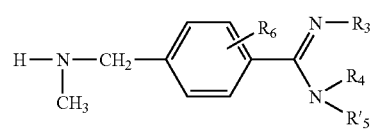

III in which

R$_3$ represents a hydrogen atom or with R$_4$ forms a straight or branched C$_2$-C$_4$ alkylene group, R$_4$ represents a hydrogen atom or with R$_3$ forms a straight or branched C$_2$-C$_4$ alkylene group, R'$_5$ represents a C$_1$-C$_3$ alkyl group, a hydrogen atom or an amino-protecting group, for example the Boc group (1,1-dimethyl-ethoxycarbonyl), R$_6$ represents a hydrogen atom or a halogen, the reaction being conducted in a solvent, dichloromethane for example, in the presence of at least one activator agent such as 1-(3-dimethylaminopropyl)-3-ethylcarbodiimide (EDCI) in particular and 1-hydroxy-7-azabenzotriazole (HOAT), at a temperature generally lying between room temperature (approximately 15° C.) and 60° C. preferably for around 2 to 15 hours to obtain the amide having the formula:

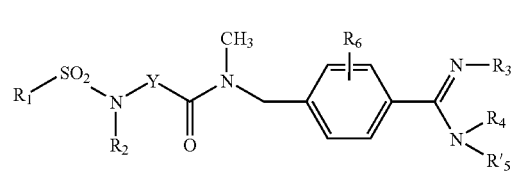

IV in which $R_1$, $R_2$, $R_3$, $R_4$, $R'_5$, $R_6$ and Y maintain the same meanings as in the starting products, 2) if necessary, when the substituent $R'_5$ is an amino-protecting group, to react the compound of formula IV so as to remove the amino-protecting group and replace it by a hydrogen atom, for example if $R'_5$ represents the Boc group, through the action of trifluoroacetic acid in the presence of anisole, thereby obtaining the compound of formula I in which $R_5$ represents a hydrogen atom, 3) if necessary, to react the compound of formula IV or I obtained above with a mineral or organic acid, to obtain an addition salt of the compound of formula IV or I.

According to another preparation method, the formula I compounds of the invention in which $R_3$, $R_4$ and $R_5$ represent a hydrogen atom, may be obtained by conducting the steps consisting of:

1) reacting an acid of formula:

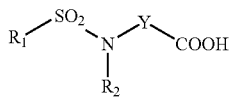

II in which $R_1$ represents an aromatic system that is non-substituted or substituted by one or more atoms or groups of atoms chosen from among the halogens, $C_1$-$C_3$, alkyl groups, $C_1$-$C_3$ alkoxy groups, trifluoromethyl or trifluoromethoxy, $R_2$ represents a hydrogen atom, a $C_1$-$C_4$ alkyl group optionally substituted by a phenyl group, by a $CONH_2$ group or by one or more fluorine atoms, and Y represents a $C_2$-$C_4$ alkylene group, saturated or unsaturated, straight or branched, optionally interrupted between two carbon atoms by an oxygen atom, with an amine of formula:

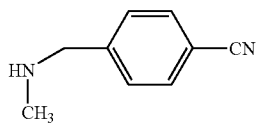

V the reaction being conducted under similar conditions to those described previously (step 1 of the general method), to obtain the compound of formula:

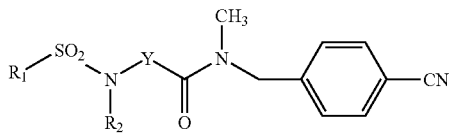

VI in which $R_1$, $R_2$, and Y maintain the same meanings as in the initial acid, 2) reacting the above formula VI compound with hydroxylamine, in a solvent such as dimethylsulphoxide (DMSO) for example in the presence of triethylamine, at a temperature generally close to room temperature, for approximately 2 to 15 hours, to obtain the compound of formula:

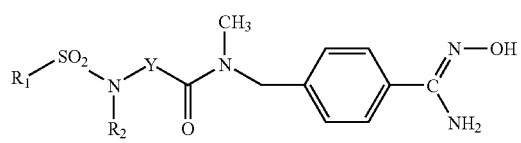

VII in which $R_1$, $R_2$ and Y remain unchanged, 3) reacting the formula VII compound with acetic anhydride, in a solvent such as dichloromethane for example, at a temperature generally close to room temperature for approximately 2 to 15 hours, to obtain the compound of formula:

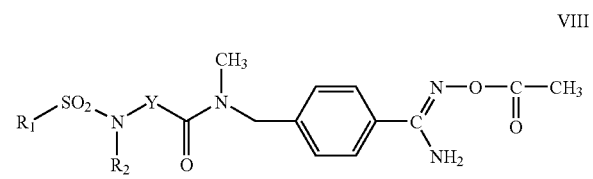

VIII 4) conducting reduction by catalytic hydrogenation of the formula VIII compound, for example in the presence of palladium black, in a solvent such as methanol for example, at a temperature close to room temperature, to obtain the compound of formula:

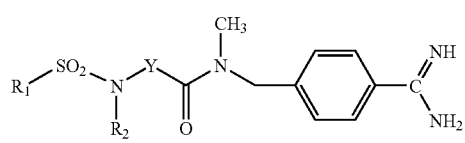

IX in which $R_1$, $R_2$ and Y remain unchanged, 5) if necessary, to obtain the salt of the formula IX compound through the addition of a suitable acid.

The compounds of formula (I) in which $R_3$ and $R_4$ together form a —CH=N— group can be obtained starting from the compound of formula VI, by successive reaction with:

1) hydrogen sulfide, for example by using pyridine as a solvent and operating at room temperature, in order to give rise to a thioamide (aminothioxomethyl) group at the site of and as a replacement for the original cyano group, 2) methyl iodide, in a solvent such as acetone, in order to give rise to an iminomethylthiomethyl group, at the site of and as a replacement for the thioamide group, 3) formylhydrazine, in a solvent such as ethanol, in order to give rise to triazole ring, at the site of and as a replacement for the previously present iminomethylthiomethyl group.

According to another method of preparation, the formula I compounds of the invention may be obtained by conducting the steps consisting of:

1) reacting an amine of formula:

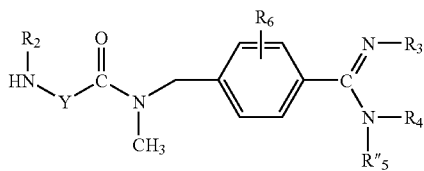

in which
R$_2$ represents a hydrogen atom, a C$_1$-C$_4$ alkyl group optionally substituted by a phenyl group, a CONH$_2$ group or by one or more fluorine atoms,
R$_3$ represents a hydrogen atom or with R$_4$ forms a straight or branched C$_2$-C$_4$ alkylene group,
R$_4$ represents a hydrogen atom or with R$_3$ forms a straight or branched C$_2$-C$_4$ alkylene group,
R"$_5$ represents an amino-protecting group, in particular the Boc group,
R$_6$ represents a hydrogen atom or a halogen,
Y represents a straight or branched C$_2$-C$_4$ alkylene group, optionally interrupted by an oxygen atom,
with an arylsulphonyl chloride of formula:

$$R_1\text{—}SO_2Cl \quad\quad XI$$

in which R$_1$ represents a non-substituted aromatic nucleus or substituted by one or more atoms or groups of atoms chosen from among the halogens, C$_1$-C$_3$ alkyl groups, C$_1$-C$_3$ alcoxy groups, nitro, cyano, trifluoromethyl or trifluoromethoxy,
the reaction being conducted in a solvent such as dichloromethane for example, in the presence of an aprotic base such as triethylamine, at room temperature and for approximately 1 to 12 hours, to obtain the compound of formula:

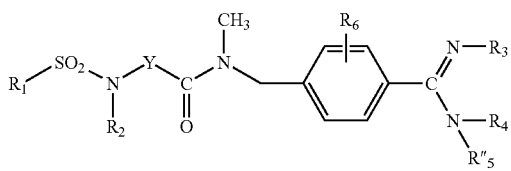

in which R$_1$, R$_2$, R$_3$, R$_4$, R"$_5$, R$_6$ and Y remain unchanged.
2) reacting the above formula IV compound, so as to remove the R"$_5$ amino-protecting group and replace it by a hydrogen atom, for example if R"$_5$ represents the Boc group, through action of trifluoroacetic aicd in the presence of anisole, thereby obtaining the compound of formula I in which R$_5$ represents a hydrogen atom.
The compounds of formula II:

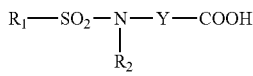

can be obtained in particular through the action of an arylsulphonyl chloride $$R_1\text{—}SO_2Cl \quad\quad XI$$

with an amine $$R_2\text{—}NH_2 \quad\quad XII,$$

followed by reaction of the amide obtained successively with sodium hydride and a halogenated acid of formula:

$$X\text{—}Y\text{—}COOH \quad\quad XIII$$

in which X represents a halogen, preferably bromine, and Y represents a C$_2$-C$_4$ alkylene group to obtain the acid of formula II.
The compounds of formula III:

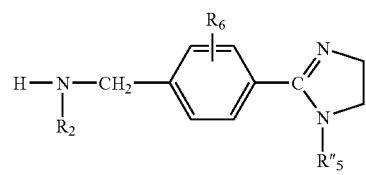

may be obtained using a method consisting of:
1) reacting an amine of formula:

XIV

H—N—CH$_2$—⟨ ⟩—CN
   |
   R$_2$
            R$_6$ with the benzyl chloroformiate, in a solvent such as dichloromethane for example and in the presence of an aprotic base to obtain the compound of formula:

XV (benzyl-CH$_2$-O-C(=O)-N(R$_2$)-CH$_2$-⟨ ⟩(R$_6$)-CN)

2) reacting the above formula XV compound with ethylenediamine, so as to obtain the compound of formula:

XVI (benzyl-CH$_2$-O-C(=O)-N(R$_2$)-CH$_2$-⟨ ⟩(R$_6$)-C(=N-)(NH-) imidazoline)

3) reacting the compound of formula XVI with the dicarbonate of di-tert-butyl, in a solvent and in the presence of an aprotic base so as to obtain the product of formula:

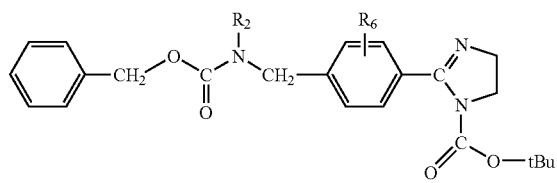

XVII 4) performing partial deprotection of the formula XVII compound, by catalytic hydrogenation for example in the presence of palladium black, so as to obtain the expected amine of formula III
in which R"$_5$ is the Boc protector group

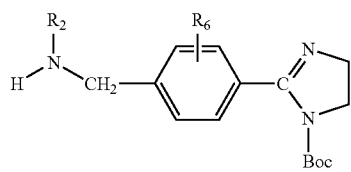

III

The invention will be more readily understood on reading the examples of preparation and the results of pharmacological tests conducted using compounds of the invention. These non-restrictive examples are solely intended to illustrate the invention and cannot be interpreted as limiting the scope thereof.

Among the abbreviations used in the following descriptions, M denotes mole, mM denotes millimole ($10^{-3}$ mole). DCM denotes dichloromethane, DMSO denotes dimethylsulphoxide.

PREPARATION I

[(4-cyanophenyl)methyl]methylcarbamic acid, phenylmethyl ester

A mixture of 7 g (47.9 mM) of [(4-cyanophenyl)methyl]methanamine is prepared in 60 ml of DCM and 5.8 g (57.5 mM) of triethylamine are added. The mixture is cooled to 0° C. and a solution of 9.8 g (57.5 mM) of benzyl chloroformate in 20 ml of DCM is added dropwise. The mixture is then agitated for 20 hours at ambient temperature and then washed with a solution of 0.1 N hydrochloric acid, and then with water, dried over sodium sulphate and concentrated under reduced pressure. The residue is purified by chromatography on silica gel in eluting with the aid of a mixture of toluene/ethyl acetate (95/5; v/v). 11.4 g of the desired product are thus obtained as an oil (yield=87%).
$n_D^{22}$=1.564

PREPARATION II

[[4-(4,5-dihydro-1H-imidazol-2-yl)phenyl]methyl] methylcarbamic acid, phenylmethyl ester A mixture of 11.3 g (40 mM) of the compound obtained according to preparation I is prepared in 40 ml of ethylenediamine and 0.64 g (20 mM) of flowers of sulphur are added. The reaction mixture is agitated for 2 hours at 100° C. and then cooled. Water is added and extraction is carried out with ethyl acetate. The organic phase is washed with water, dried over sodium sulphate and concentrated under reduced pressure. The residue is purified by chromatography on silica gel in eluting with the aid of a mixture of dichloromethane/methanol/aqueous ammonia (95/5/0.05; v/v/v). 11 g of the expected product are thus obtained as a white solid (yield=85%).
M.Pt.=84° C.

PREPARATION III 4,5-dihydro-2-[4-[[methyl[(phenylmethoxy)carbonyl]amino]methyl]-phenyl]-1H-imidazole-1-carboxylic acid, 1,1-dimethylethyl ester A solution of 3.22 g (10 mM) of the compound obtained according to preparation II is prepared in 45 ml of DCM, and 1.34 g (11 mM) of N,N-dimethylaminopyridine are added. A solution of 2.4 g (11 mM) of di-tert-butyl dicarbonate in 45 ml of DCM is then added dropwise. The reaction mixture is agitated for 2 hours at ambient temperature and then washed with the aid of a solution of 0.5 N hydrochloric acid, and then with water. The organic phase is dried over sodium sulphate and then concentrated under reduced pressure. The residue is crystallised in isopropyl ether and then filtered and dried. 4 g of the desired product are thus obtained as fine white crystals (yield=94%).
M.Pt.=124° C.

PREPARATION IV 4,5-dihydro-2-[4-[(methylamino)methyl]phenyl]-1H-imidazole-1-carboxylic acid, 1,1-dimethylethyl ester A mixture of 4.23 g (10 mM) of the compound obtained according to preparation III is prepared in 80 ml of methanol and 0.4 g of palladium on carbon (10% Pd) are added. The mixture is agitated under a hydrogen atmosphere at ambient temperature and atmospheric pressure for 2 hours. The catalyst is removed by filtration and the filtrate is then concentrated under reduced pressure. The residue is purified by chromatography on silica gel in eluting with the aid of a mixture of dichloromethane/methanol/aqueous ammonia (90/10/0.1; v/v/v). 2.5 g of the desired product are thus obtained as an off-white solid (yield=90%).
M.Pt.=65° C.

PREPARATION V

N-methyl-2,4-dichloro-3-methylbenzenesulphonamide

A suspension of 2.55 g (37.8 mM) of methanamine hydrochloride is prepared in 120 ml of dichloromethane (DCM) and 7.5 g of 2,4-dichloro-3-methylbenzenesulphonyl chloride in solution in 30 ml of DCM, and 10.5 ml of triethylamine, are added; the reaction mixture is kept under agitation for 15 hours at ambient temperature and then washed with a solution of 1N hydrochloric acid, with a solution of sodium bicarbonate, and then with water. The organic phase is dried over magnesium sulphate and then concentrated under reduced pressure. The solid residue obtained is purified by chromatography on silica gel in eluting with the aid of a mixture of cyclohexane/ethyl acetate (8/2, v/v). 6.2 g of the expected compound are thus obtained as a white solid (yield=85%).
M.Pt.=118° C.

PREPARATION VI

5-[[(2,4-dichloro-3-methylphenyl)sulphonyl]methylamino]pentanoic acid, ethyl ester A solution of 1 g (3.9 mM) of the compound obtained according to Preparation V is prepared in 30 ml of dimethylformamide and 1.63 g (11.8 mM) of potassium carbonate, and then 987 mg (4.7 mM) of ethyl 5-bromopentanoate, are added. The reaction mixture is agitated at ambient temperature for 15 hours, and water is then added thereto, and extraction is carried out with ethyl acetate. The organic phase is washed with water several times and then dried over magnesium sulphate and concentrated under reduced pressure. 1.5 g of the desired product are thus obtained as a colourless oil (quantitative yield).

$^1$H NMR (300 MHz, DMSO) δ: 7.83 (d, 1H); 7.65 (d, 1H); 4.04 (q, 2H); 3.19 (t, 2H); 2.80 (s, 3H); 2.49 (s, 3H); 2.28 (t, 2H); 1.49 (m, 4H); 1.17 (t, 3H).

PREPARATION VII

5-[[(2,4-dichloro-3-methylphenyl)sulphonyl]methylamino]pentanoic acid

A solution of 1.45 g (3.79 mM) of the ester obtained according to Preparation VI is prepared in 15 ml of tetrahydrofuran (THF) and 320 mg (7.56 mM) of lithia, and 30 ml of water, are added. The reaction mixture is agitated for 15 hours at ambient temperature. The THF is drawn off under reduced pressure and 50 ml of water are added to the residual aqueous phase, and the aqueous phase is acidified with the aid of an N solution of hydrochloric acid, and then extracted with the aid of ethyl acetate. The organic phase obtained is washed with water, dried over magnesium sulphate and concentrated under reduced pressure. 1.3 g of the expected acid are thus obtained as a colourless oil (yield=97%).

$^1$H NMR (300 MHz, DMSO) δ: 12.0 (broad s, 1H); 7.83 (d, 1H); 7.64 (d, 1H); 3.20 (t, 2H); 2.80 (s, 3H); 2.57 (s, 3H); 2.20 (t, 2H); 1.49 (m, 4H).

PREPARATION VIII

2-[4-[[[5-[[(2,4-dichloro-3-methylphenyl)sulphonyl]methylamino]-1-oxopentyl]methylamino]methyl]phenyl]-4,5-dihydro-1H imidazole-1-carboxylic acid, 1,1-dimethylethyl ester A solution of 200 mg (0.565 mM) of the acid obtained according to Preparation VII is prepared in 15 ml of dichloromethane, and then 120 mg of EDCI and 90 mg of HOAT are added. The mixture is agitated at ambient temperature for 20 min and then 163 mg (0.565 mM) of the amine obtained according to the preparation IV, in solution in 3 ml of dichloromethane, is added. The reaction mixture is kept under agitation at ambient temperature for 15 hours, and then diluted with 40 ml of dichloromethane. This organic phase is washed with water and then dried and concentrated under reduced pressure. The oily product obtained is purified by chromatography on silica gel in eluting with the aid of a mixture of dichloromethane/methanol (98/2, v/v).

260 mg of the expected compound are thus obtained as a colourless oil (yield=73%)

$^1$H NMR (300 MHz, DMSO) δ: 7.80 (t, 1H); 7.60 (m, 1H); 7.40 (m, 2H); 7.20 (m, 2H); 4.52 (d, 2H); 3.84 (m, 4H); 3.20 (m, 2H); 2.88 (s, 3H); 2.81 (s, 3H); 2.79 (m, 2H); 2.49 (s, 3H); 2.38 (m, 2H); 2.30 (m, 4H); 1.17 (s, 9H).

EXAMPLE 1

5-[[(2,4-dichloro-3-methylphenyl)sulphonyl]methylamino]-N-[[4-(4,5-dihydro-1H-imidazol-2-yl)phenyl]methyl]-N-methyl-pentanamide, trifluoroacetate A mixture of 240 mg of the compound obtained according to preparation VIII, 5 ml of trifluoroacetic acid, 5 ml of dichloromethane and 41 mg of anisole is prepared and this mixture is kept under agitation for 15 hours at ambient temperature. The solvents are drawn off under reduced pressure first of all, and then secondly in the presence of toluene. The residual oil is agitated with isopropyl ether which is then removed. The oily residue is taken up with pure water. The solution is filtered and the filtrate is lyophilised. 240 mg of the desired product are thus obtained as a cotton-like white solid (yield=97%).

M.Pt.=83° C.

In operating analogously to Preparation VI, the following compounds are obtained:

PREPARATION IX

4-[[(2,4-dichloro-3-methylphenyl)sulphonyl]methylamino]butanoic acid, ethyl ester (non-isolated)

PREPARATION X

N-[(2,4-dichloro-3-methylphenyl)sulphonyl]-N-methyl-β-alanine, ethyl ester (colourless oil, yield=43%)

$^1$H NMR (300 MHz, DMSO) δ: 7.83 (d, 1H); 7.66 (d, 1H); 4.04 (q, 2H); 3.46 (t, 2H); 2.85 (s, 3H); 2.59 (t, 2H); 2.5 (s, 3H); 1.17 (t, 3H).

PREPARATION XI

4-[[(2,4-dichloro-3-methylphenyl)sulphonyl]methylamino]-(2E)-2-butenoic acid, ethyl ester (white solid, yield=53%)
M.Pt.=90° C.

In operating analogously to Preparation VII, the following compounds are obtained:

PREPARATION XII

4-[[(2,4-dichloro-3-methylphenyl)sulphonyl]methylamino]butanoic acid (white solid, quantitative yield)
M.Pt.=104° C.

PREPARATION XIII

N-[(2,4-dichloro-3-methylphenyl)sulphonyl]-N-methyl-β-alanine (white solid, yield=98%).
M.Pt.=119° C.

PREPARATION XIV

4-[[(2,4-dichloro-3-methylphenyl)sulphonyl]methylamino]-(2E)-2-butenoic acid (white solid, yield=47%).
M.Pt.=160° C.
In operating analogously to Preparation VIII, the following compounds are obtained:

PREPARATION XV

2-[4-[[[4-[[(2,4-dichloro-3-methylphenyl)sulphonyl] methylamino]-1-oxobutyl]methylamino]methyl] phenyl]-4,5-dihydro-1H-imidazole-1-carboxylic acid, 1,1-dimethylethyl ester (oil, yield=34%)
$^1$H NMR (300 MHz, DMSO) δ: 7.95 (m, 1H); 7.82 (m, 1H); 7.41 (m, 2H); 7.21 (m, 2H); 4.52 (d, 2H); 3.84 (m, 4H); 3.22 (m, 2H); 2.85 (m, 6H); 2.49 (s, 3H); 2.24 (m, 2H); 1.79 (m, 2H); 1.17 (s, 9H).

PREPARATION XVI

2-[4-[[[3-[[(2,4-dichloro-3-methylphenyl)sulphonyl] methylamino]-1-oxopropyl]methylamino]methyl] phenyl]-4,5-dihydro-1H imidazole-1-carboxylic acid, 1,1-dimethylethyl ester (ecru foam, yield=55%)
M.Pt.=50° C.

PREPARATION XVII

2-[4-[[[(2E)-4-[[(2,4-dichloro-3-methylphenyl)sulphonyl]methylamino]-1-oxo-2-butenyl]methylamino]methyl]phenyl]-4,5-dihydro-1H-imidazole-1-carboxylic acid, 1,1-dimethylethyl ester.

(white solid, yield=74%).
M.Pt.=65° C.
In operating analogously to Example 1, the following 3 compounds are obtained:

EXAMPLE 2

4-[[(2,4-dichloro-3-methylphenyl)sulphonyl]methylamino]-N-[[4-(4,5-dihydro-1H-imidazol-2-yl)phenyl]methyl]-N-methyl-butanamide, trifluoroacetate (white solid, yield=92%)
M.Pt.=90° C.

EXAMPLE 3

3-[[(2,4-dichloro-3-methylphenyl)sulphonyl]methylamino]-N-[[4-(4,5-dihydro-1H-imidazol-2-yl)phenyl]methyl]-N-methyl-propanamide, trifluoroacetate (white solid, yield=87%)
M.Pt.=65° C.

EXAMPLE 4

4-[[(2,4-dichloro-3-methylphenyl)sulphonyl]methylamino]-N-[[4-(4,5-dihydro-1H-imidazol-2-yl)phenyl]methyl]-N-methyl-(2E)-2-butenamide, trifluoroacetate (white solid, yield=100%)
M.Pt.=55° C.
In operating analogously to Preparation V, the following compounds are obtained:

PREPARATION XVIII 2-chloro-N-methyl-benzenesulphonamide (yellow oil, yield=94%)
$^1$H NMR (300 MHz, DMSO) δ: 7.95 (d, 1H); 7.65 (m, 3H); 7.54 (t, 1H); 2.47 (s, 3H).

PREPARATION XIX 2,3-dichloro-N-methylbenzenesulphonamide (ecru solid, yield=76%)
M.Pt.=126° C.

PREPARATION XX 2,6-dichloro-N-methylbenzenesulphonamide (white solid, yield=99%)
M.Pt.=110° C.

PREPARATION XXI

N-methyl-1-naphthalenesulphonamide (beige solid, yield=94%)
$^1$H NMR (250 MHz, DMSO) δ: 8.63 (m, 1H); 8.23 (d, 1H); 8.10 (m, 2H); 7.72 (q, 1H); 7.66 (m, 3H); 2.42 (d, 3H).
In operating analogously to Preparation VI, the following compounds are obtained:

PREPARATION XXII

5-[[(2-chlorophenyl)sulphonyl]methylamino]-pentanoic acid, ethyl ester (non-isolated)

PREPARATION XXIII

4-[[(2-chlorophenyl)sulphonyl]methylamino]-(2E)-2-butenoic acid, ethyl ester (colourless oil, yield=78%)
$^1$H NMR (250 MHz, DMSO) δ: 8.02 (d, 1H); 7.71 (m, 2H); 7.60 (m, 1H); 6.79 (m, 1H); 6.04 (d, 1H); 4.08 (d, 2H); 3.67 (s, 3H); 2.80 (s, 3H).

PREPARATION XXIV

N-[(2,3-dichlorophenyl)sulphonyl]-N-methyl-β-alanine, ethyl ester (oil, yield=74%)
$^1$H NMR (250 MHz, DMSO) δ: 7.94 (m, 2H), 7.57 (m, 1H); 4.02 (q, 2H); 3.48 (t, 2H); 2.88 (s, 3H); 2.59 (t, 2H); 1.17 (t, 3H).

PREPARATION XXV

4-[[(2,3-dichlorophenyl)sulphonyl]methylamino] butanoic acid, ethyl ester (yellow oil, yield=69%)
$^1$H NMR (250 MHz, DMSO) δ: 7.93 (m, 2H); 7.57 (t, 1H); 4.03 (q, 2H); 3.24 (t, 2H); 2.84 (s, 3H); 2.29 (t, 2H); 1.75 (m, 2H); 1.17 (t, 3H).

PREPARATION XXVI

5-[[(2,3-dichlorophenyl)sulphonyl]methylamino] pentanoic acid, ethyl ester (non-isolated)

PREPARATION XXVII

4-[[(2,3-dichlorophenyl)sulphonyl]methylamino]-(2E)-2-butenoic acid, ethyl ester (white solid, yield=72%)
M.Pt.=98° C.

PREPARATION XXVIII

5-[[(2,6-dichlorophenyl)sulphonyl]methylamino] pentanoic acid, ethyl ester (non-isolated)

PREPARATION XXIX

4-[[(2,6-dichlorophenyl)sulphonyl]methylamino]-(2E)-2-butenoic acid, ethyl ester (white solid, yield=81%)
M.Pt.=84° C.

PREPARATION XXX

5-[methyl(1-naphthalenylsulphonyl)amino]pentanoic acid, ethyl ester (colourless oil, yield=93%)
$^1$H NMR (250 MHz, DMSO) δ: 8.58 (d, 1H); 8.27 (d, 1H); 8.08 (m, 2H); 7.69 (m, 3H); 4.04 (q, 2H); 3.16 (t, 2H); 2.77 (s, 3H); 2.25 (t, 2H); 1.45 (m, 4H); 1.16 (t, 3H).

PREPARATION XXXI

4-[methyl(1-naphthalenylsulphonyl)amino]-(2E)-2-butenoic acid, ethyl ester (white solid, yield=54%)
M.Pt.=75° C.

In operating analogously to Preparation VII, the following compounds are obtained:

PREPARATION XXXII

5-[[(2-chlorophenyl)sulphonyl]methylamino]pentanoic acid (white solid, yield=75%)
M.Pt.=120° C.

PREPARATION XXXIII

4-[[(2-chlorophenyl)sulphonyl]methylamino]-(2E)-2-butenoic acid (white solid, yield=50%)
M.Pt.=136° C.

PREPARATION XXXIV

N-[(2,3-dichlorophenyl)sulphonyl]-N-methyl-β-alanine (white solid, yield=74%)
M.Pt.=141° C.

PREPARATION XXXV

4-[[(2,3-dichlorophenyl)sulphonyl]methylamino] butanoic acid (white solid, yield=78%)
M.Pt.=114° C.

PREPARATION XXXVI

5-[[(2,3-dichlorophenyl)sulphonyl]methylamino] pentanoic acid (colourless oil, yield=63%)
$^1$H NMR (250 MHz, DMSO) δ: 12.0 (broad s, 1H); 7.94 (d, 2H); 7.56 (t, 1H); 3.25 (t, 2H); 2.73 (s, 3H); 2.24 (t, 2H); 1.50 (m, 4H).

PREPARATION XXXVII

4-[[(2,3-dichlorophenyl)sulphonyl]methylamino]-(2E)-2-butenoic acid (colourless oil, yield=60%)
$^1$H NMR (250 MHz, DMSO) δ: 7.96 (m, 2H); 7.58 (t, 1H); 6.58 (m, 1H); 5.90 (d, 1H); 4.04 (d, 2H); 2.81 (s, 3H).

PREPARATION XXXVIII

5-[[(2,6-dichlorophenyl)sulphonyl]methylamino] pentanoic acid (white ecru solid, yield=59%)
M.Pt.=105° C.

PREPARATION XXXIX

4-[[(2,6-dichlorophenyl)sulphonyl]methylamino]-(2E)-2-butenoic acid (white solid, yield=48%)
M.Pt.=158° C.

PREPARATION XL

5-[methyl(1-naphthalenylsulphonyl)amino]pentanoic acid (colourless oil, yield=74%)
$^1$H NMR (300 MHz, DMSO) δ: 12.0 (broad s, 1H); 8.62 (d, 1H); 8.58 (d, 1H); 8.25 (m, 2H); 8.08 (m, 3H); 3.16 (t, 2H); 2.77 (s, 3H); 2.20 (t, 2H); 1.48 (m, 4H).

PREPARATION XLI

4-[methyl(1-naphthalenylsulphonyl)amino]-(2E)-2-butenoic acid (white solid, yield=38%)
$^1$H NMR (250 MHz, DMSO) δ: 12.5 (broad s, 1H); 8.60 (d, 1H); 8.29 (d, 1H); 8.13 (m, 2H); 7.75 (m, 3H); 6.64 (m, 1H); 5.90 (d, 1H); 4.03 (d, 2H); 2.78 (s, 3H).

In operating analogously to Preparation VIII, the following compounds are obtained:

PREPARATION XLII

2-[4-[[[5-[[(2-chlorophenyl)sulphonyl]methylamino]-1-oxopentyl]methylamino]methyl]phenyl]-4,5-dihydro-1H-imidazole-1-carboxylic acid, 1,1-dimethylethyl ester (oil, yield=65%)
$^1$H NMR (300 MHz, DMSO) δ: 7.97 (t, 1H); 7.66 (m, 2H); 7.54 (m, 1H); 7.44 (m, 2H); 7.20 (m, 2H); 4.55 (d, 2H); 3.84 (m, 4H); 3.20 (m, 2H); 2.85 (m, 6H); 2.36 (m, 2H); 1.50 (m, 4H); 1.17 (d, 9H).

PREPARATION XLIII

2-[4-[[[(2E)-4-[[(2-chlorophenyl)sulphonyl]methylamino]-1-oxo-2-butenyl]methylamino]methyl]phenyl]-4,5-dihydro-1H-imidazole-1-carboxylic acid, 1,1-dimethylethyl ester (colourless paste, yield=82%)
$^1$H NMR (300 MHz, DMSO) δ: 8.03 (t, 1H); 7.67 (m, 2H); 7.51 (m, 1H); 7.42 (m, 2H); 7.20 (m, 2H); 6.60 (m, 2H); 4.60 (d, 2H); 4.05 (m, 2H); 3.84 (m, 4H); 2.88 (m, 6H); 1.18 (s, 9H).

PREPARATION XLIV

2-[4-[[[3-[[(2,3-dichlorophenyl)sulphonyl]methylamino]-1-oxopropyl]methylamino]methyl]phenyl]-4,5-dihydro-1H-imidazole-1-carboxylic acid, 1,1-dimethylethyl ester (white solid, yield=42%)
M.Pt.=65° C.

PREPARATION XLV

2-[4-[[[4-[[(2,3-dichlorophenyl)sulphonyl]methylamino]-1-oxobutyl]methylamino]methyl]phenyl]-4,5-dihydro-1H-imidazole-1-carboxylic acid, 1,1-dimethylethyl ester (white solid, yield=68%)
M.Pt.=50° C.

PREPARATION XLVI

2-[4-[[[5-[[(2,3-dichlorophenyl)sulphonyl]methylamino]-1-oxopentyl]methylamino]methyl]phenyl]-4,5-dihydro-1H-imidazole-1-carboxylic acid, 1,1-dimethylethyl ester (white solid, yield=47%)
M.Pt.=50° C.

PREPARATION XLVII

2-[4-[[[(2E)-4-[[(2,3-dichlorophenyl)sulphonyl]methylamino]-1-oxo-2-butenyl]methylamino]methyl]phenyl]-4,5-dihydro-1H-imidazole-1-carboxylic acid, 1,1-dimethylethyl ester (white paste, yield=69%)
$^1$H NMR (250 MHz, DMSO) δ: 8.02 (m, 2H); 7.59 (m, 1H); 7.43 (m, 2H); 7.21 (m, 2H); 6.60 (m, 2H); 4.70 (d, 2H); 4.00 (m, 2H); 3.82 (m, 4H); 2.86 (m, 6H); 1.18 (s, 9H).

PREPARATION XLVIII

2-[4-[[[5-[[(2,6-dichlorophenyl)sulphonyl]methylamino]-1-oxopentyl]methylamino]methyl]phenyl]-4,5-dihydro-1H-imidazole-1-carboxylic acid, 1,1-dimethylethyl ester (oil, yield=51%)
$^1$H NMR (250 MHz, DMSO) δ: 7.67 (m, 2H); 7.64 (m, 1H); 7.42 (m, 2H); 7.20 (m, 2H); 4.55 (d, 2H); 3.84 (m, 4H); 3.23 (m, 2H); 2.83 (m, 6H); 2.39 (m, 2H); 1.55 (m, 4H); 1.17 (s, 9H).

PREPARATION IL

2-[4-[[[(2E)-4-[[(2,6-dichlorophenyl)sulphonyl]methylamino]-1-oxo-2-butenyl]methylamino]methyl]phenyl]-4,5-dihydro-1H-imidazole-1-carboxylic acid, 1,1-dimethylethyl ester (white solid, yield=70%)
M.Pt.=70° C.

PREPARATION L

2-[4-[[[5-[methyl[(1-naphthalenyl)sulphonyl]amino]-1-oxopentyl]methylamino]methyl]phenyl]-4,5-dihydro-1H-imidazole-1-carboxylic acid, 1,1-dimethylethyl ester (white solid, yield=70%)
$^1$H NMR (300 MHz, DMSO) δ: 8.60 (m, 1H); 8.25 (d, 1H); 8.07 (m, 2H); 7.65 (m, 3H); 7.43 (m, 2H); 7.24 (m, 2H); 4.53 (d, 2H); 3.84 (m, 4H); 3.17 (m, 2H); 2.80 (m, 6H); 2.35 (m, 2H); 1.48 (m, 4H); 1.17 (s, 9H).

PREPARATION LI

2-[4-[[[(2E)-4-[methyl[(1-naphthalenyl)sulphonyl]amino]-1-oxo-2-butenyl]methylamino]methyl]phenyl]-4,5-dihydro-1H-imidazole-1-carboxylic acid, 1,1-dimethylethyl ester (colourless paste, yield=79%)
$^1$H NMR (300 MHz, DMSO) δ: 8.60 (t, 1H); 8.26 (d, 1H); 8.13 (m, 2H); 7.70 (m, 3H); 7.42 (d, 2H); 7.16 (m, 2H); 6.55 (m, 2H); 4.54 (s, 2H); 4.00 (m, 2H); 3.84 (m, 4H); 2.70 (m, 6H); 1.16 (d, 9H).

In operating analogously to Example 1, the following compounds are obtained:

EXAMPLE 5

5-[[(2-chlorophenyl)sulphonyl]methylamino]-N-[[4-(4,5-dihydro-1H-imidazol-2-yl)phenyl]methyl]-N-methyl-pentanamide, trifluoroacetate (white solid, yield=98%)
M.Pt.=60° C.

EXAMPLE 6

(2E)-4-[[(2-chlorophenyl)sulphonyl]methylamino]-N-[[4-(4,5-dihydro-1H-imidazol-2-yl)phenyl]methyl]-N-methyl-2-butenamide, trifluoroacetate (white solid, yield=90%)
M.Pt.=72° C.

EXAMPLE 7

3-[[(2,3-dichlorophenyl)sulphonyl]methylamino]-N-[[4-(4,5-dihydro-1H-imidazol-2-yl)phenyl]methyl]-N-methyl-propanamide, trifluoroacetate (white solid, yield=84%)
M.Pt.=60° C.

EXAMPLE 8

4-[[(2,3-dichlorophenyl)sulphonyl]methylamino]-N-[[4-(4,5-dihydro-1H-imidazol-2-yl)phenyl]methyl]-N-methyl-butanamide, trifluoroacetate (white solid, yield=91%)
M.Pt.=62° C.

EXAMPLE 9

5-[[(2,3-dichlorophenyl)sulphonyl]methylamino]-N-[[4-(4,5-dihydro-1H-imidazol-2-yl)phenyl]methyl]-N-methyl-pentanamide, trifluoroacetate (white solid, yield=80%)
M.Pt.=64° C.

EXAMPLE 10

(2E)-4-[[(2,3-dichlorophenyl)sulphonyl]methylamino]-N-[[4-(4,5-dihydro-1H-imidazol-2-yl)phenyl]methyl]-N-methyl-2-butenamide, trifluoroacetate (white solid, yield=94%)
M.Pt.=66° C.

EXAMPLE 11

5-[[(2,6-dichlorophenyl)sulphonyl]methylamino]-N-[[4-(4,5-dihydro-1H-imidazol-2-yl)phenyl]methyl]-N-methyl-pentanamide, trifluoroacetate (ecru solid, yield=65%)
M.Pt.=50° C.

EXAMPLE 12

(2E)-4-[[(2,6-dichlorophenyl)sulphonyl]methylamino]-N-[[4-(4,5-dihydro-1H-imidazol-2-yl)phenyl]methyl]-N-methyl-2-butenamide, trifluoroacetate (beige solid, yield=98%)
M.Pt.=83° C.

EXAMPLE 13

5-[methyl[(1-naphthalenyl)sulphonyl]amino]-N-[[4-(4,5-dihydro-1H imidazol-2-yl)phenyl]methyl]-N-methyl-pentanamide, trifluoroacetate (white solid, yield=97%)
$^1$H NMR (250 MHz, DMSO) δ: 10.5 (d, 2H); 8.60 (t, 1H); 8.26 (d, 1H); 8.09 (m, 2H); 7.90 (m, 2H); 7.70 (m, 3H); 7.45 (d, 2H); 4.60 (d, 2H); 4.01 (s, 4H); 3.20 (m, 2H); 2.85 (m, 6H); 2.40 (m, 2H); 1.52 (m, 4H).

EXAMPLE 14

(2E)-4-[methyl[(1-naphthalenyl)sulphonyl]amino]-N-[[4-(4,5-dihydro-1H-imidazol-2-yl)phenyl]methyl]-N-methyl-2-butenamide, trifluoroacetate (beige solid, yield=99%)
M.Pt.=77° C.

In operating analogously to Preparation V, the following compounds are obtained:

PREPARATION LII 2-chloro-N-cyclopropyl-benzenesulphonamide (white solid, yield=82%)
M.Pt.=117° C.

PREPARATION LIII

N-cyclopropyl-2,3-dichloro-benzenesulphonamide (ecru solid, yield=50%)
M.Pt.=140° C.

PREPARATION LIV

N-cyclopropyl-2,6-dichloro-benzenesulphonamide (white solid, yield=99%)
M.Pt.=76° C.

PREPARATION LV 2,3-dichloro-N-(1-methylethyl)-benzenesulphonamide (white solid, yield=93%)
M.Pt.=131° C.

PREPARATION LVI 2,6-dichloro-N-(1-methylethyl)-benzenesulphonamide (white solid, yield=99%)
M.Pt.=105° C.

PREPARATION LVII

N-(2-amino-2-oxoethyl)-2,4-dichloro-3-methylbenzenesulphonamide (oil, yield=95%)
$^1$H NMR (300 MHz, DMSO) δ: 8.04 (s, 1H); 7.82 (d, 1H); 7.62 (d, 1H); 7.12 (s, 1H); 7.03 (s, 1H); 3.50 (s, 2H); 2.48 (s, 3H).

PREPARATION LVIII

N-(3-amino-3-oxopropyl)-2,4-dichloro-3-methylbenzenesulphonamide (white solid, yield=81%)
M.Pt.=163° C.

PREPARATION LIX 2,3-dichloro-N-(2,2,2-trifluoroethyl)benzenesulphonamide (ecru solid, yield=76%)
M.Pt.=107° C.

PREPARATION LX 2,6-dichloro-N-(2,2,2-trifluoroethyl)benzenesulphonamide (white solid, yield=99%)
M.Pt.=106° C.

PREPARATION LXI 2,4-dichloro-3-methyl-N-(2-phenylethyl)benzenesulphonamide (white solid, yield=81%)
M.Pt.=75° C.

In operating analogously to Preparation VI, the following compounds are obtained:

PREPARATION LXII

5-[[(2-chlorophenyl)sulphonyl]cyclopropylamino]pentanoic acid, ethyl ester (white solid, yield=82%)
M.Pt.=117° C.

PREPARATION LXIII

5-[cyclopropyl[(2,3-dichlorophenyl)sulphonyl]amino]pentanoic acid, ethyl ester (yellow oil, yield=98%)
$^1$H NMR (250 MHz, DMSO$_3$) δ: 8.00 (m, 2H); 7.58 (t, 1H); 4.05 (q, 2H); 3.42 (t, 2H); 2.50 (m, 1H); 2.33 (t, 2H); 1.59 (m, 4H); 1.18 (t, 3H); 0.60 (m, 2H); 0.40 (m, 2H).

PREPARATION LXIV

5-[cyclopropyl[(2,6-dichlorophenyl)sulphonyl]amino]pentanoic acid, ethyl ester (non-isolated).

PREPARATION LXV

5-[[(2,6-dichlorophenyl)sulphonyl](1-methylethyl)amino]pentanoic acid, ethyl ester (non-isolated).

PREPARATION LXVI

5-[(2-amino-2-oxoethyl)[(2,4-dichloro-3-methylphenyl)sulphonyl]amino]pentanoic acid, ethyl ester (yellow oil, yield=95%)
$^1$H NMR (300 MHz, DMSO) δ: 7.91 (d, 1H); 7.64 (d, 1H); 7.15 (s, 1H); 7.01 (s, 1H); 4.04 (m, 2H); 3.95 (s, 2H); 3.27 (t, 2H); 2.49 (s, 3H); 2.15 (t, 2H); 1.62 (m, 1H); 1.20 (m, 3H); 1.17 (t, 3H).

PREPARATION LXVII

5-[(3-amino-3-oxopropyl)[(2,4-dichlorophenyl)sulphonyl]amino]-pentanoic acid, ethyl ester (colourless oil, yield=99%)
$^1$H NMR (300 MHz, DMSO) δ: 7.84 (d, 1H); 7.65 (d, 1H); 7.34 (s, 1H); 6.84 (s, 1H); 4.04 (m, 2H); 3.51 (m, 2H); 3.25 (m, 2H); 2.50 (s, 3H); 2.30 (m, 2H); 2.22 (t, 2H); 1.44 (m, 4H); 1.17 (t, 3H).

In operating analogously to Preparation VI but by replacing the brominated ethyl ester by an iodinated t-butyl ester, the following compounds are obtained:

PREPARATION LXVIII

[2-[[(2-chlorophenyl)sulphonyl]cyclopropylamino]ethoxy]acetic acid, 1,1-dimethylethyl ester (yellow oil, yield=52%)
$^1$H NMR (250 MHz, DMSO) δ: 8.00 (d, 1H); 7.68 (d, 2H); 7.57 (m, 1H); 3.98 (s, 2H); 3.69 (t, 2H); 3.52 (t, 2H); 2.50 (m, 1H); 1.43 (s, 9H); 0.56 (m, 2H); 0.45 (m, 2H).

PREPARATION LXIX

[2-[cyclopropyl[(2,3-dichlorophenyl)sulphonyl]amino]ethoxy]acetic acid, 1,1-dimethylethyl ester (colourless oil, yield=78%)
$^1$H NMR (250 MHz, DMSO) δ: 8.00 (m, 2H); 7.60 (t, 1H); 4.08 (s, 2H); 3.69 (t, 2H); 3.56 (t, 2H); 2.56 (m, 1H); 1.42 (s, 9H); 0.60 (m, 2H); 0.50 (m, 2H).

PREPARATION LXX

[2-[cyclopropyl[(2,6-dichlorophenyl)sulphonyl]amino]ethoxy]acetic acid, 1,1-dimethylethyl ester (ecru solid, yield=40%)
M.Pt.=76° C.

PREPARATION LXXI

[2-[[(2,4-dichloro-3-methylphenyl)sulphonyl](2-phenylethyl)amino]-ethoxy]acetic acid, 1,1-dimethylethyl ester (colourless oil, yield=77%)

$^1$H NMR (250 MHz, DMSO) δ: 7.86 (m, 1H); 7.60 (m, 1H); 7.17 (m, 6H); 3.94 (s, 2H); 3.56 (m, 6H); 2.80 (m, 2H); 2.44 (d, 3H); 1.42 (s, 9H).

In operating analogously to Preparation VIII, the following compounds are obtained:

PREPARATION LXXII

5-[[(2-chlorophenyl)sulphonyl]cyclopropylamino]pentanoic acid (white solid, yield=86%)
M.Pt.=104° C.

PREPARATION LXXIII

5-[cyclopropyl[(2,3-dichlorophenyl)sulphonyl]amino]pentanoic acid (ecru solid, yield=79%)
M.Pt.=115° C.

PREPARATION LXXIV

5-[cyclopropyl[(2,6-dichlorophenyl)sulphonyl]amino]pentanoic acid (yellow solid, yield=53%)
M.Pt.=146° C.

PREPARATION LXXV

5-[[(2,6-dichlorophenyl)sulphonyl](1-methylethyl)-amino]pentanoic acid (oil, yield=36%)
$^1$H NMR (300 MHz, DMSO) δ: 12.0 (broad s, 1H); 7.67 (d, 2H); 7.56 (t, 1H); 3.98 (m, 1H); 3.97 (t, 2H); 2.17 (t, 2H); 1.48 (m, 4H); 1.06 (d, 6H).

PREPARATION LXXVI

5-[(2-amino-2-oxoethyl)[(2,4-dichloro-3-methylphenyl)sulphonyl]-amino]pentanoic acid (white solid, yield=63%)
M.Pt.=160° C.

PREPARATION LXXVII

5-[(3-amino-3-oxopropyl)[(2,4-dichlorophenyl)sulphonyl]-amino]pentanoic acid (white solid, yield=93%)
M.Pt.=161° C.

PREPARATION LXXVIII

[2-[[(2-chlorophenyl)sulphonyl]cyclopropylamino]ethoxy]acetic acid

A solution of 210 mg (0.5 mM) of the ester obtained according to the preparation LXVIII is prepared in 10 ml of dichloromethane, and 3 ml of trifluoroacetic acid are added. This reaction mixture is kept under agitation for 16 hours, at ambient temperature. The reaction medium is then concentrated under reduced pressure, taken up by 30 ml of toluene and once again concentrated under reduced pressure. The residue crystallised during drying. The expected product is thus obtained as a white solid (yield=99%).

M.Pt.=115° C.

In operating analogously to Preparation LXXVIII, the following compounds are obtained:

PREPARATION LXXIX

[2-[cyclopropyl[(2,3-dichlorophenyl)sulphonyl]amino]ethoxy]acetic acid (yellow solid, yield=99%)
M.Pt.=96° C.

PREPARATION LXXX

[2-[cyclopropyl[(2,6-dichlorophenyl)sulphonyl]amino]ethoxy]acetic acid (white solid, yield=88%)
M.Pt.=98° C.

PREPARATION LXXXI

[2-[[(2,4-dichloro-3-methylphenyl)sulphonyl](2-phenylethyl)amino]ethoxy]acetic acid (yellow oil, yield=77%)
$^1$H NMR (300 MHz, DMSO) δ: 12.0 (broad s, 1H); 7.87 (d, 1H); 7.60 (d, 1H); 7.15 (m, 5H); 3.91 (s, 2H); 3.56 (m, 6H); 2.81 (t, 2H); 2.43 (s, 3H).

PREPARATION LXXXII

N-[(2,6-dichlorophenyl)sulphonyl]-N-methyl-β-alanine

A solution of 480 mg (2 mM) of the compound obtained according to preparation XX is prepared in 7 ml of dimethylformamide and 120 mg (4 mM) 80% sodium hydride in oil are added. The mixture is agitated 2 min at ambient temperature and 306 mg (2 mM) of 3-bromopropanoic acid are then added. The reaction medium is kept under agitation for 1 hour at ambient temperature, and then 20 hours at 70° C. After cooling, the mixture is hydrolysed over 50 ml of iced water. This aqueous phase is extracted with ethyl acetate, and then acidified to pH 2 with the aid of N hydrochloric acid and extracted with ethyl acetate. This latter organic phase is washed with water and then dried over sodium sulphate, and then concentrated under reduced pressure. The expected acid is thus obtained as a white amorphous solid (yield=70%).

M.Pt.=115° C.

In operating analogously to Preparation LXXXII, the following compounds are obtained:

PREPARATION LXXXIII

N-[(2,3-dichlorophenyl)sulphonyl]-N-methyl-β-alanine (white solid, yield=70%)
M.Pt.=115° C.

PREPARATION LXXXIV

N-cyclopropyl-N-[(2,6-dichlorophenyl)sulphonyl]-β-alanine (ecru solid, yield=55%)
M.Pt.=190° C.

PREPARATION LXXXV

N-[(2,3-dichlorophenyl)sulphonyl]-N-(1-methylethyl)-β-alanine (ecru solid, yield=47%)
M.Pt.=115° C.

PREPARATION LXXXVI

N-[(2,6-dichlorophenyl)sulphonyl]-N-(1-methylethyl)-β-alanine (white solid, yield=53%)
M.Pt.=138° C.

PREPARATION LXXXVII

N-[(2,3-dichlorophenyl)sulphonyl]-N-(2,2,2-trifluoroethyl)-β-alanine (ecru solid, yield=92%)
M.Pt.=125° C.

PREPARATION LXXXVIII

N-[(2,6-dichlorophenyl)sulphonyl]-N-(2,2,2-trifluoroethyl)-β-alanine (white solid, yield=77%)
M.Pt.=100° C.

In operating analogously to Preparation V, the following compound is obtained:

PREPARATION LXXXIX

N-methyl-2-(trifluoromethyl)benzenesulphonamide (white solid, yield=99%)
M.Pt.=107° C.

PREPARATION XC 2,4-dichloro-3-methylbenzenesulphonamide

A solution of 5 g (16.8 mM) of 2,4-dichloro-N-(1,1-dimethylethyl)-3-methylbenzenesulphonamide is prepared in 100 ml of dichloromethane and 50 ml of trifluoroacetic acid are added. The reaction mixture is agitated at ambient temperature for 20 hours. 20 ml of 10N hydrochloric acid are then added and agitation is maintained for 4 hours at ambient temperature. The mixture is then concentrated under reduced pressure. The solid residue is purified by chromatography on silica gel in eluting by means of a mixture of toluene-ethyl acetate (9/1; v/v). 3.74 g of the desired product are thus obtained (yield=92%).
M.Pt.=210° C.

In operating analogously to Preparation VI, the following compounds are obtained:

PREPARATION XCI (2E)-4-[methyl[[2-(trifluoromethyl)phenyl]sulphonyl]amino]-2-butenoic acid, 1,1-dimethylethyl ester (yellow oil, yield=44%)
$^1$H NMR (250 MHz, DMSO) δ: 8.04 (m, 2H); 7.90 (m, 2H); 6.66 (dt, 1H); 5.88 (dt, 1H); 4.07 (dd, 2H); 2.84 (s, 3H); 1.44 (s, 9H).

PREPARATION XCII (2E)-4-[[(2,4-dichloro-3-methylphenyl)sulphonyl]amino]-2-butenoic acid, 1,1-dimethylethyl ester (yellow oil, yield=20%)
$^1$H NMR (300 MHz, DMSO) δ: 8.33 (s, 1H); 7.81 (d, 1H); 7.63 (d, 1H); 6.49 (dt, 1H); 5.69 (dt, 1H); 3.70 (dd, 2H); 2.48 (s, 3H); 1.38 (s, 9H).

In operating analogously to Preparation LXXVIII, the following compounds are obtained:

PREPARATION XCIII (2E)-4-[[(2,4-dichloro-3-methylphenyl)sulphonyl]amino]-2-butenoic acid (white solid, yield=99%)
M.Pt.=154° C.

PREPARATION XCIV

4-[methyl[[2-(trifluoromethyl)phenyl]sulphonyl]amino]-2-butenoic acid (white solid, yield=99%)
M.Pt.=184° C.

In operating analogously to Preparation VIII, the following compounds are obtained:

PREPARATION XCV

2-[4-[[[5-[[(2-chlorophenyl)sulphonyl]cyclopropylamino]-1-oxopentyl]methylamino]methyl]phenyl]-4,5-dihydro-1H-imidazole-1-carboxylic acid, 1,1-dimethylethyl ester (amorphous solid, yield=84%)
M.Pt.=50° C.

PREPARATION XCVI

2-[4-[[[5-[cyclopropyl[(2,3-dichlorophenyl)sulphonyl]amino]-1-oxopentyl]methylamino]methyl]phenyl]-4,5-dihydro-1H-imidazole-1-carboxylic acid, 1,1-dimethylethyl ester (colourless oil, yield=65%)
$^1$H NMR (300 MHz, DMSO) δ: 7.97 (m, 2H); 7.40 (m, 1H); 7.25 (m, 2H); 7.18 (m, 2H); 4.55 (d, 2H); 3.84 (m, 4H); 3.40 (m, 2H); 2.85 (d, 3H); 2.46 (m, 3H); 1.60 (m, 4H); 1.17 (s, 9H); 0.59 (m, 2H); 0.42 (m, 2H).

PREPARATION XCVII

2-[4-[[[5-[cyclopropyl[(2,6-dichlorophenyl)sulphonyl]amino]-1-oxopentyl]methylamino]methyl]phenyl]-4,5-dihydro-1H-imidazole-1-carboxylic acid, 1,1-dimethylethyl ester (amorphous solid, yield=59%)
M.Pt.=50° C.

PREPARATION XCVIII

2-[4-[[[5-[[(2,6-dichlorophenyl)sulphonyl](1-methylethyl)amino]-1-oxopentyl]methylamino]methyl]phenyl]-4,5-dihydro-1H-imidazole-1-carboxylic acid, 1,1-dimethylethyl ester (white solid, yield=69%)
M.Pt.=50° C.

PREPARATION IC

2-[4-[[[5-[(2-amino-2-oxoethyl)[(2,4-dichloro-3-methylphenyl)-sulphonyl]amino]-1-oxopentyl]methylamino]methyl]phenyl]-4,5-dihydro-1H-imidazole-1-carboxylic acid, 1,1-dimethylethyl ester (white solid, yield=69%)
M.Pt.=70° C.

PREPARATION C

2-[4-[[[5-[(3-amino-3-oxopropyl)[(2,4-dichloro-3-methylphenyl)-sulphonyl]amino]-1-oxopentyl]methylamino]methyl]phenyl]-4,5-dihydro-1H-imidazole-1-carboxylic acid, 1,1-dimethylethyl ester (white solid, yield=76%)
M.Pt.=80° C.

PREPARATION CI

2-[4-[[[3-[[(2,3-dichlorophenyl)sulphonyl](1-methylethyl)amino]-1-oxopropyl]methylamino]methyl]phenyl]-4,5-dihydro-1H-imidazole-1-carboxylic acid, 1,1-dimethylethyl ester (white solid, yield=55%)
M.Pt.=60° C.

PREPARATION CII

2-[4-[[[3-[[(2,6-dichlorophenyl)sulphonyl](1-methylethyl)amino]-1-oxopropyl]methylamino]methyl]phenyl]-4,5-dihydro-1H-imidazole-1-carboxylic acid, 1,1-dimethylethyl ester (white solid, yield=54%)
M.Pt.=55° C.

PREPARATION CIII

2-[4-[[[[2-[[(2-chlorophenyl)sulphonyl]cyclopropylamino]-ethoxy]acetyl]methylamino]methyl]phenyl]-4,5-dihydro-1H-imidazole-1-carboxylic acid, 1,1-dimethylethyl ester (amorphous solid, yield=96%)
M.Pt.=50° C.

PREPARATION CIV

2-[4-[[[[2-[cyclopropyl[(2,3-dichlorophenyl)sulphonyl]amino]ethoxy]-acetyl]methylamino]methyl]phenyl]-4,5-dihydro-1H-imidazole-1-carboxylic acid, 1,1-dimethylethyl ester (white solid, yield=56%)
M.Pt.=62° C.

PREPARATION CV

2-[4-[[[[2-[cyclopropyl[(2,6-dichlorophenyl)sulphonyl]amino]ethoxy]-acetyl]methylamino]-methyl]phenyl]-4,5-dihydro-1H-imidazole-1-carboxylic acid, 1,1-dimethylethyl ester (amorphous solid, yield=64%)
M.Pt.=55° C.

PREPARATION CVI

2-[4-[[[[2-[[(2,4-dichloro-3-methylphenyl)sulphonyl](2-phenylethyl)-amino]ethoxy]acetyl]methylamino]methyl]phenyl]-4,5-dihydro-1H imidazole-1-carboxylic acid, 1,1-dimethylethyl ester (colourless oil, yield=63%)
$^1$H NMR (250 MHz, DMSO) δ: 7.87 (m, 1H); 7.60 (m, 1H); 7.30 (m, 3H); 7.20 (m, 6H); 4.52 (s, 2H); 4.19 (d, 2H); 3.84 (m, 4H); 3.60 (m, 6H); 2.83 (s, 3H); 2.77 (t, 2H); 2.48 (d, 3H); 1.17 (s, 9H).

PREPARATION CVII

2-[4-[[[3-[[(2,6-dichlorophenyl)sulphonyl]methylamino]-1-oxopropyl]methylamino]methyl]phenyl]-4,5-dihydro-1H-imidazole-1-carboxylic acid, 1,1-dimethylethyl ester (white solid, yield=60%)
M.Pt.=55° C.

PREPARATION CVIII

2-[4-[[[3-[cyclopropyl[(2,3-dichlorophenyl)sulphonyl]amino]-1-oxopropyl]methylamino]methyl]phenyl]-4,5-dihydro-1H-imidazole-1-carboxylic acid, 1,1-dimethylethyl ester (white solid, yield=64%)
M.Pt.=60° C.

PREPARATION CIX

2-[4-[[[3-[cyclopropyl[(2,6-dichlorophenyl)sulphonyl]amino]-1-oxopropyl]methylamino]methyl]phenyl]-4,5-dihydro-1H-imidazole-1-carboxylic acid, 1,1-dimethylethyl ester (white solid, yield=63%)
M.Pt.=64° C.

PREPARATION CX

2-[4-[[[3-[[(2,3-dichlorophenyl)sulphonyl](2,2,2-trifluoroethyl)-amino]-1-oxopropyl]methylamino]methyl]phenyl]-4,5-dihydro-1H-imidazole-1-carboxylic acid, 1,1-dimethylethyl ester (white solid, yield=33%)
M.Pt.=55° C.

PREPARATION CXI

2-[4-[[[3-[[(2,6-dichlorophenyl)sulphonyl](2,2,2-trifluoroethyl)-amino]-1-oxopropyl]methylamino]methyl]phenyl]-4,5-dihydro-1H-imidazole-1-carboxylic acid, 1,1-dimethylethyl ester (white solid, yield=36%)
M.Pt.=50° C.

PREPARATION CXII 4,5-dihydro-2-[4-[[methyl[(2E)-4-[methyl[[2-(trifluoromethyl)phenyl]sulphonyl]amino]-1-oxo-2-butenyl]amino]methyl]phenyl]-1H-imidazole-1-carboxylic acid, 1,1-dimethylethyl ester (colourless oil, yield=62%)
$^1$H NMR (250 MHz, DMSO) δ: 8.04 (m, 2H); 7.88 (m, 2H); 7.43 (m, 2H); 7.17 (m, 2H); 6.60 (m, 2H); 4.62 (d, 2H); 4.05 (dd, 2H); 3.83 (m, 4H); 2.86 (m, 6H); 1.17 (m, 9H).

PREPARATION CXIII

2-[4-[[[(2E)-4-[[(2,4-dichloro-3-methylphenyl)sulphonyl]amino]-1-oxo-2-butenyl]methylamino]methyl]phenyl]-4,5-dihydro-1H-imidazole-1-carboxylic acid, 1,1-dimethylethyl ester (colourless oil, yield=50%)
$^1$H NMR (300 MHz, DMSO) δ: 8.31 (s, 1H); 7.82 (t, 1H); 7.62 (dd, 1H); 7.44 (dd, 2H); 7.22 (dd, 2H); 6.50 (m, 2H); 4.55 (d, 2H); 3.84 (m, 4H); 3.70 (m, 2H); 2.82 (d, 3H); 2.47 (m, 3H); 1.18 (s, 9H).

In operating analogously to Example 1, the following compounds are obtained:

EXAMPLE 15

5-[[(2-chlorophenyl)sulphonyl]cyclopropylamino]-N-[[4-(4,5-dihydro-1H-imidazol-2-yl)phenyl]methyl]-N-methyl-pentanamide, trifluoroacetate (white solid, yield=84%)
M.Pt.=55° C.

EXAMPLE 16

5-[cyclopropyl[(2,3-dichlorophenyl)sulphonyl]amino]-N-[[4-(4,5-dihydro-1H-imidazol-2-yl)phenyl]methyl]-N-methyl-pentanamide, trifluoroacetate (ecru solid, yield=99%)
M.Pt.=70° C.

EXAMPLE 17

5-[cyclopropyl[(2,6-dichlorophenyl)sulphonyl]amino]-N-[[4-(4,5-dihydro-1H-imidazol-2-yl)phenyl]methyl]-N-methyl-pentanamide, trifluoreoacetate (white solid, yield=86%)
M.Pt.=60° C.

EXAMPLE 18

5-[[(2,6-dichlorophenyl)sulphonyl](1-methylethyl)amino]-N-[[4-(4,5-dihydro-1H-imidazol-2-yl)phenyl]methyl]-N-methyl-pentanamide, trifluoroacetate (white solid, yield=98%)
M.Pt.=60° C.

EXAMPLE 19

5-[(2-amino-2-oxoethyl)[(2,4-dichloro-3-methylphenyl)sulphonyl]-amino]-N-[[4-(4,5-dihydro-1H-imidazol-2-yl)phenyl]methyl]-N-methyl-pentanamide, trifluoroacetate (white solid, yield=99%)
M.Pt.=90° C.

EXAMPLE 20

5-[(3-amino-3-oxopropyl)[(2,4-dichloro-3-methylphenyl)sulphonyl]-amino]-N-[[4-(4,5-dihydro-1H-imidazol-2-yl)phenyl]methyl]-N-methyl-pentanamide, trifluoroacetate (white solid, yield=95%)
M.Pt.=85° C.

EXAMPLE 21

3-[[(2,3-dichlorophenyl)sulphonyl](1-methylethyl)amino]-N-[[4-(4,5-dihydro-1H-imidazol-2-yl)phenyl]methyl]-N-methyl-propanamide, trifluoroacetate (white solid, yield=73%)
M.Pt.=92° C.

EXAMPLE 22

3-[[(2,6-dichlorophenyl)sulphonyl](1-methylethyl)amino]-N-[[4-(4,5-dihydro-1H-imidazol-2-yl)phenyl]methyl]-N-methyl-propanamide, trifluoroacetate (white solid, yield=73%)
M.Pt.=75° C.

EXAMPLE 23

2-[2-[[(2-chlorophenyl)sulphonyl]cyclopropylamino]ethoxy]-N-[[4-(4,5-dihydro-1H-imidazol-2-yl)phenyl]methyl]-N-methyl-acetamide, trifluoroacetate (white solid, yield=71%)
M.Pt.=52° C.

EXAMPLE 24

2-[2-[cyclopropyl[(2,3-dichlorophenyl)sulphonyl]amino]ethoxy]-N-[[4-(4,5-dihydro-1H-imidazol-2-yl)phenyl]methyl]-N-methyl-acetamide, trifluoroacetate (white solid, yield=97%)
M.Pt.=65° C.

EXAMPLE 25

2-[2-[cyclopropyl[(2,6-dichlorophenyl)sulphonyl]amino]ethoxy]-N-[[4-(4,5-dihydro-1H-imidazol-2-yl)phenyl]methyl]-N-methyl-acetamide, trifluoroacetate (white solid, yield=99%)
M.Pt.=60° C.

EXAMPLE 26

2-[2-[[(2,4-dichloro-3-methylphenyl)sulphonyl](2-phenylethyl)-amino]ethoxy]-N-[[4-(4,5-dihydro-1H-imidazol-2-yl)phenyl]methyl]-N-methyl-acetamide, trifluoroacetate (white solid, yield=81%)
M.Pt.=85° C.

EXAMPLE 27

3-[[(2,6-dichlorophenyl)sulphonyl]methylamino]-N-[[4-(4,5-dihydro-1H-imidazol-2-yl)phenyl]methyl]-N-methyl-propanamide, trifluoroacetate (white solid, yield=73%)
M.Pt.=75° C.

EXAMPLE 28

3-[cyclopropyl[(2,3-dichlorophenyl)sulphonyl]amino]-N-[[4-(4,5-dihydro-1H-imidazol-2-yl)phenyl]methyl]-N-methyl-propanamide, trifluoroacetate (white solid, yield=86%)
M.Pt.=80° C.

EXAMPLE 29

3-[cyclopropyl[(2,6-dichlorophenyl)sulphonyl]amino]-N-[[4-(4,5-dihydro-1H-imidazol-2-yl)phenyl]methyl]-N-methyl-propanamide, trifluoroacetate (white solid, yield=84%)
M.Pt.=65° C.

EXAMPLE 30

3-[(2,2,2-trifluoroethyl)[(2,3-dichlorophenyl)sulphonyl]amino]-N-[[4-(4,5-dihydro-1H-imidazol-2-yl)phenyl]methyl]-N-methyl-propanamide, trifluoroacetate (white solid, yield=90%)
M.Pt.=88° C.

EXAMPLE 31

3-[(2,2,2-trifluoroethyl)[(2,6-dichlorophenyl)sulphonyl]amino]-N-[[4-(4,5-dihydro-1H-imidazol-2-yl)phenyl]methyl]-N-methyl-propanamide, trifluoroacetate (white solid, yield=80%)
M.Pt.=80° C.

EXAMPLE 32

N-[[4-(4,5-dihydro-1H-imidazol-2yl)phenyl]methyl]-N-methyl-4-[methyl[[2-(trifluoromethyl)phenyl]sulphonyl]amino]-(2E)-2-butenamide, trifluoroacetate (white solid, yield=99%)
M.Pt.=50° C.

EXAMPLE 33

4-[[(2,4-dichloro-3-methylphenyl)sulphonyl]amino]-N-[[4-(4,5-dihydro-1H-imidazol-2-yl)phenyl]methyl]-N-methyl-(2E)-2-butenamide, trifluoroacetate (white solid, yield=62%)
M.Pt.=99° C.

PREPARATION CXIV

[(4-cyanophenyl)methyl]methylcarbamic acid, 1,1-dimethylethyl ester

A solution of 1.94 g (13 mM) of [(4-cyanophenyl)methyl]methanamine is prepared in 100 ml of dichloromethane and 1.78 g (14.6 mM) of 4-dimethylaminopyridine, and then 3.19 g (14.6 mM) of di-t-butyl dicarbonate, are added. The reaction mixture is agitated at ambient temperature for 2 hours. The organic phase is washed with water and then with a solution of citric acid, and then with water, and then dried over magnesium sulphate and concentrated under reduced pressure. The crude product is purified by chromatography on silica gel in eluting with a mixture of toluene/isopropanol (9/1, v/v). 2.91 g of the desired product are thus obtained as a colourless oil (yield=82%).

$^1$H NMR (250 MHz, DMSO) δ: 7.82 (d, 2H); 7.39 (d, 2H); 4.45 (s, 2H); 2.79 (s, 3H); 1.38 (s, 9H).

PREPARATION CXV

[[4-(4,5-dihydro-5,5-dimethyl-1H-imidazol-2-yl)phenyl]methyl]methylcarbamic acid, 1,1-dimethylethyl ester In operating analogously to Preparation II, starting with the compound obtained according to Preparation CXIV and 1,2-diamino-2-methylpropane, the expected product is obtained as a colourless oil with a yield of 82%.

$^1$H NMR (300 MHz, DMSO) δ: 7.78 (d, 2H); 7.25 (d, 2H); 4.39 (s, 2H); 3.36 (s, 2H); 2.76 (s, 3H); 1.39 (s, 9H); 1.23 (s, 6H).

PREPARATION CXVI 4-(4,5-dihydro-5,5-dimethyl-1H-imidazol-2-yl)-N-methyl-benzenemethanamine, dihydrochloride A solution of 1.585 g (5 mM) of the compound obtained according to preparation CXV is prepared in 80 ml of ethyl acetate and 24 ml of a solution of hydrogen chloride in ethyl acetate are added slowly. The mixture is agitated at ambient temperature for 20 hours. The precipitate is separated off by filtration and then washed with ethyl acetate and then ethyl ether, and then dried in an anhydrous medium. 1.33 g of the desired product are thus obtained (yield 92%).

$^1$H NMR (250 MHz, DMSO) δ: 7.73 (d, 2H); 7.33 (d, 2H); 3.65 (s, 2H); 3.35 (s, 2H); 2.24 (s, 3H); 1.22 (s, 6H).

In operating analogously to Preparation VIII, starting with the compound obtained according to preparation CXVI, the following compound is obtained:

EXAMPLE 34

5-[[(2,4-dichloro-3-methylphenyl)sulphonyl]methylamino]-N-[[4-(5,5-dimethyl-4,5-dihydro-1H-imidazol-2-yl)phenyl]methyl]-N-methylpentanamide (white solid, yield=38%)
M.Pt.=104° C.

EXAMPLE 35

5-[[(2,4-dichloro-3-methylphenyl)sulphonyl]methylamino]-N-[[4-(5,5-dimethyl-4,5-dihydro-1H-imidazol-2-yl)phenyl]methyl]-N-methylpentanamide, hydrochloride A solution of 62.6 mg (0.113 mM) of the compound obtained according to Example 34 is prepared in 10 ml of methanol and 225 μl of an N solution of hydrochloric acid are added. Mixing is carried out under agitation for 5 min and then concentration is carried out under reduced pressure. The residue is taken up in 5 ml of pure water and lyophilised. 48 mg of the expected compound are thus obtained as a white solid.

(yield=72%)
M.Pt.=104° C.

In operating analogously to Preparation V, the following compounds are obtained:

PREPARATION CXVII 2,4-dichloro-3,N-dimethyl-N-(2-hydroxyethyl)benzenesulphonamide (non-isolated).

PREPARATION CXVIII 2,3-dichloro-N-(2-hydroxy-1-methylethyl)-N-methylbenzenesulphonamide (colourless oil, yield=71%)
$^1$H NMR (300 MHz, DMSO) δ: 8.05 (d, 1H); 8.01 (d, 1H); 7.55 (t, 1H); 4.76 (t, 1H); 3.79 (m, 1H); 3.40 (m, 2H); 2.81 (s, 3H); 1.04 (d, 3H).

PREPARATION CXIX 2,3-dichloro-N-(2-hydroxyethyl)-N-methylbenzenesulphonamide (colourless oil, yield=99%)
$^1$H NMR (300 MHz, DMSO) δ: 7.93 (m, 2H); 7.55 (t, 1H); 3.49 (m, 2H); 3.27 (t, 2H); 2.90 (s, 3H).

PREPARATION CXX 2,6-dichloro-N-(2-hydroxyethyl)-N-methylbenzenesulphonamide (yellow oil, yield=99%)
$^1$H NMR (300 MHz, DMSO) δ: 7.67 (d, 2H); 7.57 (m, 1H); 4.79 (t, 1H); 3.54 (q, 2H); 3.29 (t, 2H); 2.92 (s, 3H).

PREPARATION CXXI 2-chloro-N-(2-hydroxyethyl)-N-methylbenzenesulphonamide (oil, yield=99%)
$^1$H NMR (300 MHz, DMSO) δ: 7.95 (d, 1H); 7.66 (m, 2H); 7.60 (m, 1H); 4.79 (t, 1H); 3.53 (q, 2H); 3.25 (t, 2H); 2.88 (s, 3H).

PREPARATION CXXII

[2-[[(2,4-dichloro-3-methylphenyl)sulphonyl]methylamino]-ethoxy]acetic acid, 1,1-dimethylethyl ester A solution of 100 mg (0.335 mM) of compound obtained according to the preparation CXVII is prepared in 4 ml of toluene and 30 mg (0.111 mM) of tetrabutylammonium chloride, and then 4 ml of a 35% solution of sodium hydroxide, are added. The reaction medium is cooled to 10° C. and 98 mg (0.5 mM) of t-butyl bromoacetate are then added. The mixture is agitated at ambient temperature for 30 min, and then hydrolysed over iced water. The mixture obtained is extracted with toluene and the organic phase obtained is dried over magnesium sulphate and concentrated under reduced pressure. The expected product is thus obtained as a colourless oil (yield=87%).

$^1$H NMR (300 MHz, DMSO) δ: 7.84 (d, 1H); 7.63 (d, 1H); 3.93 (s, 2H); 3.59 (t, 2H); 3.39 (t, 2H); 2.91 (s, 3H); 2.49 (s, 3H); 1.41 (s, 9H).

In operating analogously to Preparation CXXII, the following compounds are obtained:

PREPARATION CXXIII

[2-[[(2,3-dichlorophenyl)sulphonyl]methylamino]propoxy]acetic acid, 1,1-dimethylethyl ester (colourless oil, yield=88%)
$^1$H NMR (250 MHz, DMSO) δ: 8.05 (d, 1H); 8.02 (d, 1H); 7.92 (t, 1H); 4.01 (m, 1H); 3.82 (s, 2H); 3.47 (m, 2H); 2.85 (s, 3H); 1.42 (s, 9H); 1.03 (d, 3H).

PREPARATION CXXIV

[2-[[(2,3-dichlorophenyl)sulphonyl]methylamino]ethoxy]acetic acid, 1,1-dimethylethyl ester (colourless oil, yield=96%)
$^1$H NMR (300 MHz, DMSO) δ: 7.94 (m, 2H); 7.56 (t, 1H); 3.93 (s, 2H); 3.60 (t, 2H); 3.40 (t, 2H); 2.94 (s, 3H); 1.42 (s, 9H).

PREPARATION CXXV

[2-[[(2,6-dichlorophenyl)sulphonyl]methylamino]ethoxy]acetic acid, 1,1-dimethylethyl ester (yellow oil, yield=99%).
$^1$H NMR (250 MHz, DMSO) δ: 7.67 (d, 2H); 7.55 (m, 1H); 3.93 (s, 2H); 3.62 (t, 2H); 3.43 (d, 2H); 2.94 (s, 3H); 1.41 (s, 9H).

PREPARATION CXXVI

[2-[[(2-chlorophenyl)sulphonyl]methylamino]ethoxy]acetic acid, 1,1-dimethylethyl ester (oil, yield=99%).
$^1$H NMR (300 MHz, DMSO) δ: 7.98 (d, 1H); 7.67 (m, 2H); 7.54 (m, 1H); 3.94 (s, 2H); 3.60 (t, 2H); 3.39 (t, 2H); 2.85 (s, 3H); 1.42 (s, 9H).

In operating analogously to Preparation VII, the following compounds are obtained:

PREPARATION CXXVII

[2-[[(2,4-dichloro-3-methylphenyl)sulphonyl]methylamino]ethoxy]-acetic acid (colourless oil, yield=100%)
$^1$H NMR (300 MHz, DMSO) δ: 12.5 (broad s, 1H); 7.86 (d, 1H); 7.64 (d, 1H); 4.02 (s, 2H); 3.61 (t, 2H); 3.40 (t, 2H); 2.91 (s, 3H); 2.51 (s, 3H).

PREPARATION CXXVIII

[2-[[(2,3-dichlorophenyl)sulphonyl]methylamino]propoxy]acetic acid (colourless oil, yield=81%).
$^1$H NMR (300 MHz, DMSO) δ: 12.6 (broad s, 1H); 8.06 (d, 1H); 7.92 (d, 1H); 7.53 (t, 1H); 3.98 (m, 1H); 3.82 (s, 2H); 3.50 (m, 2H); 2.85 (s, 3H); 1.05 (d, 3H).

In operating analogously to Preparation LXXVIII, the following compounds are obtained:

PREPARATION CXXIX

[2-[[(2,3-dichlorophenyl)sulphonyl]methylamino]ethoxy]acetic acid (white ecru solid, yield=100%).
M.Pt.=80° C.

PREPARATION CXXX

[2-[[(2,6-dichlorophenyl)sulphonyl]methylamino]ethoxy]acetic acid (yellow oil, yield=100%).
$^1$H NMR (250 MHz, DMSO) δ: 12.6 (broad s, 1H); 7.67 (d, 2H); 7.55 (m, 3H); 3.97 (s, 2H); 3.63 (t, 2H); 3.44 (t, 2H); 2.94 (s, 3H).

PREPARATION CXXXI

[2-[[(2-chlorophenyl)sulphonyl]methylamino]ethoxy]acetic acid (colourless oil, yield=99%).
$^1$H NMR (300 MHz, DMSO) δ: 12.5 (broad s, 1H); 7.95 (d, 1H); 7.66 (m, 2H); 7.55 (m, 1H); 3.97 (s, 2H); 3.61 (t, 2H); 3.39 (t, 2H); 2.90 (s, 3H).

PREPARATION CXXXII

Methyl[[4-(1,4,5,6-tetrahydro-2-pyrimidinyl)phenyl]methyl]carbamic acid, 1,1-dimethylethyl ester In operating analogously to Preparation CXV, starting with 1,3-propanediamine, the expected product is obtained as a colourless oil with a yield of 30%.
$^1$H NMR (250 MHz, DMSO) δ: 7.75 (d, 2H); 7.37 (d, 2H); 4.44 (s, 2H); 3.47 (t, 4H); 2.79 (s, 3H); 1.90 (m, 2H); 1.40 (s, 9H).

PREPARATION CXXXIII

N-methyl-4-(1,4,5,6-tetrahydro-2-pyrimidinyl)-benzenemethanamine, dihydrochloride In operating analogously to Preparation CXVI, the expected product is obtained as a yellow oil (yield=100%).
$^1$H NMR (250 MHz, DMSO) δ: 10.23 (s, 2H); 9.73 (broad s, 2H); 7.83 (m, 4H); 4.20 (t, 2H); 3.50 (s, 4H); 2.51 (m, 3H); 1.95 (m, 2H).

PREPARATION CXXXIV

[[4-(4,5-dihydro-1-methyl-1H-imidazol-2-yl)phenyl]methyl]methylcarbamic acid, 1,1-dimethylethyl ester In operating analogously to Preparation CXV, starting with 1,2-propanediamine, the expected product is obtained as a yellow oil (yield=74%).
$^1$H NMR (250 MHz, DMSO) δ: 7.49 (d, 2H); 7.26 (d, 2H); 4.4 (s, 2H); 3.68 (t, 2H); 3.34 (t, 2H); 2.78 (s, 3H); 2.70 (s, 3H); 1.40 (s, 9H).

PREPARATION CXXXV

N-methyl-4-(4,5-dihydro-1-methyl-1H-imidazol-2-yl)benzenemethanamine, dihydrochloride In operating analogously to Preparation CXVI, the expected product is obtained as a beige oil (yield=100%).
$^1$H NMR (250 MHz, DMSO) δ: 10.44 (s, 1H); 9.13 (s, 2H); 7.74 (m, 4H); 4.26 (s, 2H); 4.08 (m, 2H); 3.92 (m, 2H); 3.05 (s, 3H); 2.61 (s, 3H).

PREPARATION CXXXVI 4-cyano-2-fluoro-N-methylbenzenemethanamine 1 ml of a 16.5% solution of methanamine in ethanol is cooled by an ice bath and a solution of 120 mg (0.56 mM) of 4-(bromomethyl)-3-fluoro-benzonitrile in 1 ml of dichloromethane is added dropwise. The reaction medium is then agitated for 4 hours at ambient temperature and is then concentrated under reduced pressure. The residue is taken up with ethyl acetate and washed with a solution of sodium bicarbonate. The organic phase is dried over magnesium sulphate and then concentrated under reduced pressure. The crude product is purified by chromatography on silica gel in eluting with the aid of a mixture of dichloromethane/ methanol (98/0.05; v/v). The expected amine is thus obtained as a colourless oil (yield=49%).

$^1$H NMR (300 MHz, DMSO) δ: 7.78 (d, 1H); 7.64 (m, 2H); 3.73 (s, 2H); 2.33 (s, 1H); 2.26 (s, 3H).

In operating analogously to Preparations I to IV, the following compounds are obtained successively:

PREPARATION CXXXVII

[(2-fluoro-4-cyanophenyl)methyl]methylcarbamic acid, phenylmethyl ester (yellow oil, yield=99%).
$^1$H NMR (300 MHz, DMSO) δ: 7.84 (d, 1H); 7.67 (m, 1H); 7.36 (m, 8H); 5.16 (d, 2H); 4.57 (s, 2H); 2.91 (s, 3H).

PREPARATION CXXXVIII

[[2-fluoro-4-(4,5-dihydro-1H-imidazol-2-yl)phenyl] methyl]methylcarbamic acid, phenylmethyl ester (white solid, yield=70%).
M.Pt.=90° C.

PREPARATION CXXXIX

2-[3-fluoro-4-[[methyl[(phenylmethoxy)carbonyl] amino]-methyl]phenyl]-4,5-dihydro-1H-imidazole-1-carboxylic acid, 1,1-dimethylethyl ester (white solid, yield=99%).
M.Pt.=131° C.

PREPARATION CXL

2-[3-fluoro-4-[(methylamino)methyl]phenyl]-4,5-dihydro-1H-imidazole-1-carboxylic acid, 1,1-dimethylethyl ester (yellow oil, yield=81%).
$^1$H NMR (300 MHz, DMSO) δ: 7.44 (t, 1H); 7.23 (m, 3H); 3.84 (m, 4H); 3.69 (s, 2H); 2.25 (s, 3H); 1.21 (s, 9H).

In operating analogously to Preparation VIII, the following compounds are obtained:

PREPARATION CXLI

2-[4-[[[[2-[[(2,4-dichloro-3-methylphenyl)sulphonyl]methylamino]-ethoxy]acetyl]methylamino]methyl]phenyl]-4,5-dihydro-1H-imidazole-1-carboxylic acid, 1,1-dimethylethyl ester (colourless oil, yield=81%).
$^1$H NMR (250 MHz, DMSO) δ: 7.87 (t, 1H); 7.62 (m, 1H); 7.44 (m, 2H); 7.24 (d, 2H); 4.51 (s, 2H); 4.19 (d, 2H); 3.83 (m, 4H); 3.62 (m, 2H); 3.43 (m, 2H); 2.85 (m, 6H); 1.18 (s, 9H).

PREPARATION CXLII

2-[4-[[[[2-[[(2,3-dichlorophenyl)sulphonyl]methylamino]propoxy]-acetyl]methylamino]methyl]phenyl]-4,5-dihydro-1H-imidazole-1-carboxylic acid, 1,1-dimethylethyl ester (colourless oil, yield=52%).
$^1$H NMR (250 MHz, DMSO) δ: 8.08 (m, 1H); 7.89 (m, 1H); 7.50 (m, 3H); 7.30 (m, 2H); 4.49 (d, 2H); 4.05 (d, 2H); 3.98 (m, 1H); 3.84 (m, 4H); 3.49 (m, 2H); 2.83 (m, 6H); 1.18 (s, 1H); 1.04 (t, 3H).

PREPARATION CXLIII

2-[4-[[[[2-[[(2,3-dichlorophenyl)sulphonyl]methylamino]ethoxy]-acetyl]methylamino]methyl]phenyl]-4,5-dihydro-1H-imidazole-1-carboxylic acid, 1,1-dimethylethyl ester (colourless oil, yield=73%).
$^1$H NMR (300 MHz, DMSO) δ: 7.95 (m, 2H); 7.50 (m, 3H); 7.24 (d, 2H); 4.52 (s, 2H); 4.18 (d, 2H); 3.83 (m, 4H); 3.64 (m, 2H); 3.46 (m, 2H); 2.91 (m, 6H); 1.18 (s, 9H).

PREPARATION CXLIV

2-[4-[[[[2-[[(2,6-dichlorophenyl)sulphonyl]methylamino]ethoxy]-acetyl]methylamino]methyl]phenyl]-4,5-dihydro-1H-imidazole-1-carboxylic acid, 1,1-dimethylethyl ester (colourless oil, yield=58%).
$^1$H NMR (300 MHz, DMSO) δ: 7.67 (m, 2H); 7.55 (m, 1H); 7.45 (m, 2H); 7.25 (d, 2H); 4.51 (s, 2H); 4.18 (d, 2H); 3.83 (m, 4H); 3.66 (m, 2H); 3.45 (m, 2H); 2.84 (m, 6H); 1.18 (s, 9H).

EXAMPLE 36

2-[2-[[(2,3-dichlorophenyl)sulphonyl]methylamino] ethoxy]-N-methyl-N-[[4-(1,4,5,6-tetrahydro-2-pyrimidinyl)phenyl]methyl]acetamide (colourless oil, yield=25%).
$^1$H NMR (300 MHz, DMSO) δ: 7.95 (m, 2H); 7.50 (m, 3H); 7.24 (d, 2H); 4.52 (s, 2H); 4.18 (d, 2H); 3.83 (m, 4H); 3.64 (m, 2H); 3.46 (m, 2H); 2.91 (m, 6H); 1.18 (s, 9H).

EXAMPLE 37

2-[2-[[(2,4-dichloro-3-methylphenyl)sulphonyl]methylamino]ethoxy]-N-[[4-(4,5-dihydro-1-methyl-1H-imidazol-2-yl)phenyl]methyl]-N-methyl-acetamide (yellow oil, yield=25%).
$^1$H NMR (300 MHz, DMSO) δ: 7.84 (t, 1H); 7.63 (m, 1H); 7.49 (m, 2H); 7.28 (m, 2H); 4.53 (s, 2H); 4.20 (d, 2H); 3.65 (m, 4H); 3.42 (m, 4H); 2.78 (m, 9H); 2.51 (s, 3H).

EXAMPLE 38

2-[2-[[(2,3-dichlorophenyl)sulphonyl]methylamino] ethoxy]-N-[[4-(4,5-dihydro-1-methyl-1H-imidazol-2-yl)phenyl]methyl]-N-methyl-acetamide (oil, yield=20%).
$^1$H NMR (250 MHz, DMSO) δ: 7.98 (m, 2H); 7.55 (m, 3H); 7.34 (m, 2H); 4.54 (s, 2H); 4.20 (d, 2H); 3.60 (m, 8H); 2.80 (m, 9H).

PREPARATION CXLV

2-[4-[[[[2-[[(2-chlorophenyl)sulphonyl]methylamino]ethoxy]acetyl]methylamino]methyl]phenyl]-4,5-dihydro-1H-imidazole-1-carboxylic acid, 1,1-dimethylethyl ester (colourless oil, yield=46%).
$^1$H NMR (300 MHz, DMSO) δ: 7.97 (t, 1H); 7.65 (m, 2H); 7.56 (m, 1H); 7.47 (m, 2H); 7.24 (d, 2H); 4.52 (s, 2H); 4.20 (d, 2H); 3.83 (m, 4H); 3.63 (m, 2H); 3.40 (m, 2H); 2.84 (m, 6H); 1.18 (s, 9H).

PREPARATION CXLVI

2-[4-[[[[2-[[(2,3-dichlorophenyl)sulphonyl]methylamino]ethoxy]-acetyl]methylamino]methyl]-3-fluorophenyl]-4,5-dihydro-1H-imidazole-1-carboxylic acid, 1,1-dimethylethyl ester (colourless oil, yield=46%).
$^1$H NMR (250 MHz, DMSO) δ: 7.94 (m, 2H); 7.55 (dd, 1H); 7.26 (m, 3H); 4.56 (s, 2H); 4.20 (d, 2H); 3.85 (m, 4H); 3.61 (m, 2H); 3.45 (m, 2H); 2.85 (m, 6H); 1.20 (s, 9H).

In operating analogously to Example 1, the following compounds are obtained:

EXAMPLE 39

2-[2-[[(2,4-dichloro-3-methylphenyl)sulphonyl]methylamino]ethoxy]-N-[[4-(4,5-dihydro-1H-imidazol-2-yl)phenyl]methyl]-N-methyl-acetamide, trifluoroacetate (white solid, yield=98%).
M.Pt.=75° C.

EXAMPLE 40

2-[2-[[(2,3-dichlorophenyl)sulphonyl]methylamino]ethoxy]-N-[[4-(4,5-dihydro-1H-imidazol-2-yl)phenyl]methyl]-N-methyl-acetamide, trifluoroacetate (white solid, yield=96%).
M.Pt.=60° C.

EXAMPLE 41

2-[2-[[(2,6-dichlorophenyl)sulphonyl]methylamino]ethoxy]-N-[[4-(4,5-dihydro-1H-imidazol-2-yl)phenyl]methyl]-N-methyl-acetamide, trifluoroacetate (white solid, yield=96%).
M.Pt.=60° C.

EXAMPLE 42

2-[2-[[(2-chlorophenyl)sulphonyl]methylamino]ethoxy]-N-[[4-(4,5-dihydro-1H-imidazol-2-yl)phenyl]methyl]-N-methyl-acetamide, trifluoroacetate (white solid, yield=99%).
M.Pt.=60° C.

EXAMPLE 43

2-[2-[[(2,3-dichlorophenyl)sulphonyl]methylamino]ethoxy]-N-[[2-fluoro-4-(4,5-dihydro-1H-imidazol-2-yl)phenyl]methyl]-N-methyl-acetamide, trifluoroacetate (white solid, yield=87%).
M.Pt.=80° C.

In operating analogously to Preparation CXVI starting with the compound obtained according to Preparation CXLII, the following compound is obtained:

EXAMPLE 44

2-[2-[[(2,3-dichlorophenyl)sulphonyl]methylamino]propoxy]-N-[[4-(4,5-dihydro-1H-imidazol-2-yl)phenyl]methyl]-N-methyl-acetamide, hydrochloride (white solid, yield=85%).
M.Pt.=104° C.

EXAMPLE 45

2-[2-[[(2,3-dichlorophenyl)sulphonyl]methylamino]ethoxy]-N-methyl-N-[[4-(1,4,5,6-tetrahydro-2-pyrimidinyl)phenyl]methyl]acetamide, trifluoroacetate A solution of 40 mg (0.075 mM) of the compound obtained according to Example 36 is prepared in 10 ml of methanol and 5.9 μl of trifluoroacetic acid are added. The mixture is agitated 15 min at ambient temperature and then concentrated under reduced pressure. The residue is taken up in 3 ml of pure water and the solution obtained is filtered. The filtrate is lyophilised. 35 mg of the expected compound are thus obtained as a white powder (yield=73%).
$^1$H NMR (250 MHz, DMSO) δ: 10.05 (broad s, 2H); 7.98 (m, 2H); 7.73 (m, 2H); 7.56 (m, 4H); 4.59 (s, 2H); 4.20 (d, 2H); 3.65 (m, 2H); 3.46 (m, 6H); 2.87 (m, 6H); 1.98 (m, 2H).

EXAMPLE 46

2-[2-[[(2,4-dichloro-3-methylphenyl)sulphonyl]methylamino]ethoxy]-N-[[4-(4,5-dihydro-1-methyl-1H-imidazol-2-yl)phenyl]methyl]-N-methyl-acetamide, hydrochloride 90 mg (0.166 mM) of the compound obtained according to Example 37 are dissolved in 3 ml of methanol and 1 ml of a saturated solution of hydrogen chloride in ethyl ether is added. The mixture is kept under agitation at ambient temperature for 1 hour. 10 ml of ethyl ether are added and the mixture is then concentrated under reduced pressure. The residue is taken up in 6 ml of pure water. The solution obtained is filtered and then lyophilised. 95 mg of the desired product are thus obtained as a white crystallised solid (yield=98%).
M.Pt.=60° C.

EXAMPLE 47

2-[2-[[(2,3-dichlorophenyl)sulphonyl]methylamino]ethoxy]-N-[[4-(4,5-dihydro-1-methyl-1H-imidazol-2-yl)phenyl]methyl]-N-methyl-acetamide, hydrochloride In operating analogously to Example 46, starting with the compound obtained according to Example 38, the expected compound is obtained as a colourless oil
(yield=53%).

¹H NMR (250 MHz, DMSO) δ: 10.20 (s, 1H); 7.98 (m, 2H); 7.65 (m, 2H); 7.53 (m, 3H); 4.60 (s, 2H); 4.20 (d, 2H); 3.95 (m, 4H); 3.70 (m, 4H); 3.06 (s, 3H); 2.90 (m, 6H).

PREPARATION CXLVII (2-hydroxyethyl)methylcarbamic acid, 1,1-dimethylethyl ester In operating analogously to Preparation CXIV, starting with 2-(methylamino)ethanol, the expected compound is obtained as a colourless oil (yield=87%).

¹H NMR (300 MHz, DMSO) δ: 4.65 (t, 1H); 3.45 (q, 2H); 3.19 (t, 2H); 2.81 (s, 3H); 1.38 (s, 9H).

PREPARATION CXLVIII

[2-[[(1,1-dimethylethoxy)carbonyl]methylamino] ethoxy]acetic acid, 1,1-dimethylethyl ester In operating analogously to Preparation CXXII, starting with the compound obtained according to preparation CXLVII, the expected product is obtained as a yellow oil (yield=99%).

¹H NMR (250 MHz, DMSO) δ: 3.96 (s, 2H); 3.52 (t, 2H); 3.31 (t, 2H); 2.81 (s, 3H); 1.42 (s, 9H); 1.38 (s, 9H).

PREPARATION CIL

[2-(methylamino)ethoxy]acetic acid, trifluoroacetate

In operating analogously to Preparation LXXVIII, starting with the compound obtained according to Preparation CXLVIII, the expected product is obtained as a yellow oil (yield=99%).

¹H NMR (250 MHz, DMSO) δ: 8.50 (broad s, 1H); 4.09 (s, 2H); 3.70 (m, 2H); 3.11 (m, 2H); 2.60 (m, 3H).

PREPARATION CL

[2-[methyl[(phenylmethoxy)carbonyl]amino]ethoxy] acetic acid

A solution of 25 g (0.101 mM) of the compound obtained according to Preparation CIL is prepared in 400 ml of dichloromethane. 35.2 ml (0.25 mM) of triethylamine and then, dropwise, 15.5 ml of benzyl chloroformate, are added at 0° C. The reaction mixture is agitated for 5 hours at ambient temperature. The reaction mixture is hydrolysed over 200 ml of iced water and 50 ml of N hydrochloric acid. The separated organic phase is washed with water and then dried over magnesium sulphate and concentrated under reduced pressure. The crude oily product is purified by chromatography on silica gel in eluting with a mixture of toluene/isopropanol/aquous ammonia (9/1/0.1; v/v/v). 13.7 g of the desired product are thus obtained as a colourless oil (yield=51%).

¹H NMR (250 MHz, DMSO) δ: 7.33 (m, 5H); 5.06 (s, 2H); 4.10 (s, 2H); 3.58 (t, 2H); 3.49 (m, 2H); 2.90 (d, 3H).

PREPARATION CLI

2-[4-(2,8-dimethyl-3,9-dioxo-11-phenyl-5,10-dioxa-2,8-diazaundec-1-yl)phenyl]-4,5-dihydro-1H-imidazole-1-carboxylic acid, 1,1-dimethylethyl ester In operating analogously to Preparation VIII, starting with the acid obtained according to the Preparation CL, the expected product is obtained as a yellow oil (yield=62%).

¹H NMR (250 MHz, DMSO) δ: 7.42-7.22 (m, 9H); 5.05 (s, 2H); 4.51 (s, 2H); 4.21 (s, 2H); 3.84 (m, 4H); 3.58 (m, 2H); 3.45 (m, 2H); 2.88 (m, 6H); 1.17 (s, 9H).

PREPARATION CLII 4,5-dihydro-2-[4-[[methyl[[2-(methylamino)ethoxy] acetyl]amino]methyl]phenyl]-1H-imidazole-1-carboxylic acid, 1,1-dimethylethyl ester In operating analogously to Preparation IV, starting with the compound obtained according to Preparation CLI, the expected product is obtained as a yellow oil (yield=91%).

¹H NMR (250 MHz, DMSO) δ: 7.41 (d, 2H); 7.26 (d, 2H); 4.53 (d, 2H); 4.20 (d, 2H); 3.84 (m, 4H); 3.50 (m, 2H); 2.86 (s, 3H); 2.63 (m, 2H); 2.26 (d, 3H); 1.18 (s, 9H).

In operating analogously to Preparation V, starting with the compound obtained according to Preparation CLII, the following compounds are obtained:

PREPARATION CLIII 4,5-dihydro-2-[4-[[methyl[[2-[methyl[[2-(trifluoromethyl)phenyl]-sulphonyl]amino]ethoxy]acetyl] amino]methyl]phenyl]-1H-imidazole-1-carboxylic acid, 1,1-dimethylethyl ester ¹H NMR (300 MHz, DMSO) δ: 8.02 (m, 2H); 7.87 (m, 2H); 7.44 (m, 2H); 7.23 (d, 2H); 4.53 (s, 2H); 4.23 (d, 2H); 3.83 (m, 4H); 3.65 (m, 2H); 3.48 (m, 2H); 2.88 (m, 6H); 1.17 (s, 9H).

PREPARATION CLIV 4,5-dihydro-2-[4-[[[[2-[[(4-methoxy-2,6-dimethylphenyl)sulphonyl]-methylamino]ethoxy]acetyl] methylamino]methyl]phenyl]-1H-imidazole-1-carboxylic acid, 1,1-dimethylethyl ester (colourless oil, yield=74%).

¹H NMR (300 MHz, DMSO) δ: 7.42 (m, 2H); 7.22 (d, 2H); 6.80 (d, 2H); 4.50 (s, 2H); 4.15 (d, 2H); 3.84 (m, 4H); 3.79 (s, 3H); 3.57 (m, 2H); 3.22 (m, 2H); 2.76 (m, 6H); 2.53 (s, 6H); 1.17 (s, 9H).

PREPARATION CLV

2-[[[[2-[[(2,4-dichlorophenyl)sulphonyl]methylamino]ethoxy]acetyl]methylamino]methyl]phenyl]-4,5-dihydro-1H-imidazole-1-carboxylic acid, 1,1-dimethylethyl ester (colourless oil, yield=70%).

¹H NMR (250 MHz, DMSO) δ: 7.89 (m, 2H); 7.60 (m, 1H); 7.43 (m, 2H); 7.23 (d, 2H); 4.51 (s, 2H); 4.20 (d, 2H); 3.84 (m, 4H); 3.60 (m, 2H); 3.42 (m, 2H); 2.83 (m, 6H); 1.18 (s, 9H).

PREPARATION CLVI

2-[4-[[[[2-[[(2,4-dichloro-5-methylphenyl)sulphonyl]methylamino]ethoxy]acetyl]methylamino]methyl]phenyl]-4,5-dihydro-1H-imidazole-1-carboxylic acid, 1,1-dimethylethyl ester (colourless oil, yield=43%).
$^1$H NMR (300 MHz, DMSO) δ: 7.94 (m, 1H); 7.82 (m, 1H); 7.42 (m, 2H); 7.23 (d, 2H); 4.52 (s, 2H); 4.20 (d, 2H); 3.83 (m, 4H); 3.60 (m, 2H); 3.42 (m, 2H); 2.85 (m, 6H); 2.38 (s, 3H); 1.18 (s, 9H).

PREPARATION CLVII 4,5-dihydro-2-[4-[[methyl[[2-[methyl[(2-nitrophenyl)sulphonyl]amino]ethoxy]acetyl]amino]methyl]phenyl]-1H-imidazole-1-carboxylic acid, 1,1-dimethylethyl ester (white foam, yield=50%).
M.Pt.=60° C.

PREPARATION CLVIII

2-[4-[[[[2-[[[2,6-dichloro-4-(trifluoromethyl)phenyl]sulphonyl]methylamino]ethoxy]acetyl]methylamino]methyl]phenyl]-4,5-dihydro-1H-imidazole-1-carboxylic acid, 1,1-dimethylethyl ester (colourless oil, yield=55%).
$^1$H NMR (300 MHz, DMSO) δ: 8.08 (d, 2H); 7.42 (m, 2H); 7.22 (d, 2H); 4.50 (s, 2H); 4.18 (d, 2H); 3.83 (m, 4H); 3.64 (m, 2H); 3.50 (m, 2H); 2.80 (m, 6H); 1.18 (s, 9H).

PREPARATION CLIX

2-[4-[[[[2-[[(2-chloro-3-methylphenyl)sulphonyl]methylamino]-ethoxy]acetyl]methylamino]methyl]phenyl]-4,5-dihydro-1H imidazole-1-carboxylic acid, 1,1-dimethylethyl ester (white solid, yield=63%).
M.Pt.=50° C.

PREPARATION CLX

2-[4-[[[[2-[[(2-cyanophenyl)sulphonyl]methylamino]ethoxy]-acetyl]methylamino]methyl]phenyl]-4,5-dihydro-1H-imidazole-1-carboxylic acid, 1,1-dimethylethyl ester (white solid, yield=56%).
M.Pt.=60° C.

PREPARATION CLXI 4,5-dihydro-2-[4-[[methyl[[2-[methyl[(2,3,4-trichlorophenyl)-sulphonyl]amino]ethoxy]acetyl]amino]methyl]phenyl]-1H-imidazole-1-carboxylic acid, 1,1-dimethylethyl ester (white solid, yield=59%).
M.Pt.=60° C.

PREPARATION CLXII

2-[4-[[[[2-[[(3-chloro-2-methylphenyl)sulphonyl]methylamino]-ethoxy]acetyl]methylamino]methyl]phenyl]-4,5-dihydro-1H-imidazole-1-carboxylic acid, 1,1-dimethylethyl ester (colourless oil, yield=57%).
$^1$H NMR (250 MHz, DMSO) δ: 7.78 (m, 2H); 7.41 (m, 3H); 7.23 (d, 2H); 4.52 (s, 2H); 4.20 (d, 2H); 3.82 (m, 4H); 3.59 (m, 2H); 3.39 (m, 2H); 2.83 (m, 6H); 2.59 (d, 3H); 1.18 (s, 9H).

PREPARATION CLXIII

2-[4-[[[[2-[[(2-chloro-4-cyanophenyl)sulphonyl]methylamino]-ethoxy]acetyl]methylamino]methyl]phenyl]-4,5-dihydro-1H-imidazole-1-carboxylic acid, 1,1-dimethylethyl ester (white solid, yield=51%).
M.Pt.=60° C.

PREPARATION CLXIV 4,5-dihydro-2-[4-[[methyl[[2-[methyl[[2-nitro-4-(trifluoromethyl)-phenyl]sulphonyl]amino]ethoxy]acetyl]amino]methyl]phenyl]-1H-imidazole-1-carboxylic acid, 1,1-dimethylethyl ester (colourless oil, yield=47%)
$^1$H NMR (300 MHz, DMSO) δ: 8.59 (s, 1H); 8.27 (m, 2H); 7.42 (m, 2H); 7.23 (d, 2H); 4.51 (s, 2H); 4.20 (d, 2H); 3.83 (m, 4H); 3.64 (m, 2H); 3.47 (m, 2H); 2.90 (m, 6H); 1.18 (s, 9H).

PREPARATION CLXV

2-[4-[[[[2-[[(2,6-difluorophenyl)sulphonyl]methylamino]-ethoxy]acetyl]methylamino]methyl]phenyl]-4,5-dihydro-1H-imidazole-1-carboxylic acid, 1,1-dimethylethyl ester (colourless oil, yield=49%).
$^1$H NMR (250 MHz, DMSO) δ: 7.74 (m, 1H); 7.43 (m, 2H); 7.27 (m, 4H); 4.51 (s, 2H); 4.16 (d, 2H); 3.82 (m, 4H); 3.60 (m, 2H); 3.56 (m, 2H); 2.82 (m, 6H); 1.18 (s, 9H).

PREPARATION CLXVI 4,5-dihydro-2-[4-[[methyl[[2-[methyl[[4-(trifluoromethoxy)phenyl]-sulphonyl]amino]ethoxy]acetyl]amino]methyl]phenyl]-1H-imidazole-1-carboxylic acid, 1,1-dimethylethyl ester (colourless oil, yield=63%).
$^1$H NMR (250 MHz, DMSO) δ: 7.93 (m, 2H); 7.60 (d, 2H); 7.42 (m, 2H); 7.23 (d, 2H); 4.51 (s, 2H); 4.19 (d, 2H); 3.84 (m, 4H); 3.59 (m, 2H); 3.22 (m, 2H); 2.78 (m, 6H); 1.18 (s, 9H).

PREPARATION CLXVII

2-[4-[[[[2-[[(2,5-dichlorothien-3-yl)sulphonyl]methylamino]-ethoxy]acetyl]methylamino]methyl]phenyl]-4,5-dihydro-1H-imidazole-1-carboxylic acid, 1,1-dimethylethyl ester (colourless oil, yield=30%).
$^1$H NMR (250 MHz, DMSO) δ: 7.41 (m, 3H); 7.23 (d, 2H); 4.52 (s, 2H); 4.21 (d, 2H); 3.84 (m, 4H); 3.62 (m, 2H); 3.37 (m, 2H); 2.84 (m, 6H); 1.18 (s, 9H).

PREPARATION CLXVIII 4,5-dihydro-2-[4-[[methyl[[2-[methyl[(3-methylphenyl)sulphonyl]amino]ethoxy]acetyl]amino]methyl]phenyl]-1H-imidazole-1-carboxylic acid, 1,1-dimethylethyl ester (colourless oil, yield=33%).
$^1$H NMR (300 MHz, DMSO) δ: 7.60 (m, 2H); 7.56 (m, 2H); 7.50 (m, 2H); 7.22 (d, 2H); 4.52 (s, 2H); 4.20 (d, 2H); 3.84 (m, 4H); 3.57 (m, 2H); 3.17 (m, 2H); 2.76 (m, 6H); 2.40 (s, 3H); 1.18 (s, 9H).

PREPARATION CLXIX 4,5-dihydro-2-[4-[[methyl[[2-[methyl(1-naphthalenylsulphonyl)amino]ethoxy]acetyl]amino]methyl]phenyl]-1H-imidazole-1-carboxylic acid, 1,1-dimethylethyl ester (colourless oil, yield=33%).
$^1$H NMR (300 MHz, DMSO) δ: 8.60 (m, 1H); 8.20 (m, 1H); 8.08 (m, 2H); 7.68 (m, 3H); 7.46 (m, 2H); 7.23 (d, 2H); 4.50 (d, 2H); 4.13 (d, 2H); 3.84 (m, 4H); 3.59 (m, 2H); 3.41 (m, 2H); 2.86 (m, 6H); 1.17 (s, 9H).

PREPARATION CLXX 4,5-dihydro-2-[4-[[methyl[[2-[methyl[[3-(trifluoromethyl)phenyl]-sulphonyl]amino]ethoxy]acetyl]amino]methyl]phenyl]-1H-imidazole-1-carboxylic acid, 1,1-dimethylethyl ester (colourless oil, yield=66%).
$^1$H NMR (300 MHz, DMSO) δ: 8.12 (m, 3H); 7.85 (m, 1H); 7.44 (m, 2H); 7.23 (d, 2H); 4.50 (s, 2H); 4.15 (d, 2H); 3.82 (m, 4H); 3.60 (m, 2H); 3.26 (m, 2H); 2.81 (m, 6H); 1.18 (s, 9H).

PREPARATION CLXXI

2-[4-[[[[2-[[(4-chloro-3-methylphenyl)sulphonyl]methylamino]-ethoxy]acetyl]methylamino]methyl]phenyl]-4,5-dihydro-1H-imidazole-1-carboxylic acid, 1,1-dimethylethyl ester (white solid, yield=59%).
M.Pt.=60° C.

PREPARATION CLXXII

2-[4-[[[[2-[[(2,4-difluorophenyl)sulphonyl]methylamino]ethoxy]-acetyl]methylamino]methyl]phenyl]-4,5-dihydro-1H-imidazole-1-carboxylic acid, 1,1-dimethylethyl ester (colourless oil, yield=64%).
$^1$H NMR (250 MHz, DMSO) δ: 7.87 (m, 1H); 7.43 (m, 3H); 7.20 (m, 3H); 4.51 (s, 2H); 4.17 (d, 2H); 3.84 (m, 4H); 3.61 (m, 2H); 3.34 (m, 2H); 2.84 (m, 6H); 1.18 (s, 9H).

PREPARATION CLXXIII

2-[4-[[[[2-[[(3-chlorophenyl)sulphonyl]methylamino]ethoxy]acetyl]methylamino]methyl]phenyl]-4,5-dihydro-1H-imidazole-1-carboxylic acid, 1,1-dimethylethyl ester (colourless oil, yield=51%).
$^1$H NMR (300 MHz, DMSO) δ: 7.78 (m, 3H); 7.66 (m, 1H); 7.45 (m, 2H); 7.23 (d, 2H); 4.51 (s, 2H); 4.19 (d, 2H); 3.82 (m, 4H); 3.52 (m, 2H); 3.37 (m, 2H); 2.78 (m, 6H); 1.18(s, 9H).

In operating analogously to Example 1, the following compounds are obtained:

EXAMPLE 48

N-[[4-(4,5-dihydro-1H-imidazol-2-yl)phenyl]methyl]-N-methyl-2-[2-[methyl[[2-(trifluoromethyl)phenyl]sulphonyl]amino]ethoxy]-acetamide, trifluoroacetate (fine white solid, yield=96%).
M.Pt.=60° C.

EXAMPLE 49

N-[[4-(4,5-dihydro-1H-imidazol-2-yl)phenyl]methyl]-2-[2-[[(4-methoxy-2,6-dimethylphenyl)sulphonyl]methylamino]ethoxy]-N-methyl-acetamide, trifluoroacetate (pasty solid, yield=99%).
$^1$H NMR (250 MHz, DMSO) δ: 10.48 (broad s, 2H); 7.89 (d, 2H); 7.48 (d, 2H); 6.79 (s, 2H); 4.59 (s, 2H); 4.15 (d, 2H); 4.01 (s, 4H); 3.79 (s, 3H); 3.59 (m, 2H); 3.24 (m, 2H); 2.71 (m, 6H); 2.53 (s, 6H).

EXAMPLE 50

2-[2-[[(2,4-dichlorophenyl)sulphonyl]methylamino]ethoxy]-N-[[4-(4,5-dihydro-1H-imidazol-2-yl)phenyl]methyl]-N-methyl-acetamide, trifluoroacetate (white solid, yield=99%).
M.Pt.=60° C.

EXAMPLE 51

2-[2-[[(2,4-dichloro-5-methylphenyl)sulphonyl]methylamino]-ethoxy]-N-[[4-(4,5-dihydro-1H-imidazol-2-yl)phenyl]methyl]-N-methyl-acetamide, trifluoroacetate (pasty solid, yield=99%).
$^1$H NMR (250 MHz, DMSO) δ: 10.5 (d, 2H); 7.87 (m, 4H); 7.50 (d, 2H); 4.60 (s, 2H); 4.10 (d, 2H); 4.01 (s, 4H); 3.62 (m, 2H); 3.45 (m, 2H); 2.85 (m, 6H); 2.38 (s, 3H).

EXAMPLE 52

N-[[4-(4,5-dihydro-1H-imidazol-2-yl)phenyl]methyl]-N-methyl-2-[2-[methyl[(2-nitrophenyl)sulphonyl]amino]ethoxy]acetamide, trifluoroacetate (yellow paste, yield=99%).
$^1$H NMR (300 MHz, DMSO) δ: 10.49 (s, 2H); 7.89 (m, 6H); 7.49 (d, 2H); 4.61 (s, 2H); 4.22 (d, 2H); 4.01 (s, 4H); 3.66 (m, 2H); 3.41 (m, 2H); 2.90 (m, 6H).

EXAMPLE 53

2-[2-[[[2,6-dichloro-4-(trifluoromethyl)phenyl]sulphonyl]-methylamino]ethoxy]-N-[[4-(4,5-dihydro-1H-imidazol-2-yl)phenyl]methyl]-N-methyl-acetamide, trifluoroacetate (white solid, yield=99%).
M.Pt.=60° C.

EXAMPLE 54

2-[2-[[(2-chloro-3-methylphenyl)sulphonyl]methylamino]ethoxy]-N-[[4-(4,5-dihydro-1H-imidazol-2-yl)phenyl]methyl]-N-methyl-acetamide, trifluoroacetate (white solid, yield=67%).
M.Pt.=63° C.

EXAMPLE 55

2-[2-[[(2-cyanophenyl)sulphonyl]methylamino]ethoxy]-N-[[4-(4,5-dihydro-1H-imidazol-2-yl)phenyl]methyl]-N-methyl-acetamide, trifluoroacetate (white solid, yield=94%).
M.Pt.=60° C.

EXAMPLE 56

N-[[4-(4,5-dihydro-1H-imidazol-2-yl)phenyl]methyl]-N-methyl-2-[2-[methyl[(2,3,4-trichlorophenyl)sulphonyl]amino]ethoxy]acetamide, trifluoroacetate (white solid, yield=99%).
M.Pt.=70° C.

EXAMPLE 57

2-[2-[[(3-chloro-2-methylphenyl)sulphonyl]methylamino]ethoxy]-N-[[4-(4,5-dihydro-1H-imidazol-2-yl)phenyl]methyl]-N-methyl-acetamide, trifluoroacetate (fine white solid, yield=74%).
M.Pt.=60° C.

EXAMPLE 58

2-[2-[[(2-chloro-4-cyanophenyl)sulphonyl]methylamino]ethoxy]-N-[[4-(4,5-dihydro-1H-imidazol-2-yl)phenyl]methyl]-N-methyl-acetamide, trifluoroacetate (white solid, yield=97%).
M.Pt.=64° C.

EXAMPLE 59

N-[[4-(4,5-dihydro-1H-imidazol-2-yl)phenyl]methyl]-N-methyl-2-[2-[methyl[[2-nitro-4-(trifluoromethyl)phenyl]sulphonyl]amino]-ethoxy]acetamide, trifluoroacetate (white solid, yield=85%).
$^1$H NMR (250 MHz, DMSO) δ: 10.47 (s, 2H); 8.59 (s, 1H); 8.23 (m, 2H); 7.92 (m, 2H); 7.48 (d, 2H); 4.60 (s, 2H); 4.20 (d, 2H); 4.01 (s, 4H); 3.65 (m, 2H); 3.47 (m, 2H); 2.85 (m, 6H).

EXAMPLE 60

2-[2-[[(2,6-difluorophenyl)sulphonyl]methylamino]ethoxy]-N-[[4-(4,5-dihydro-1H-imidazol-2-yl)phenyl]methyl]-N-methyl-acetamide, trifluoroacetate (foam, yield=99%).
$^1$H NMR (250 MHz, DMSO) δ: 10.47 (s, 2H); 7.92 (m, 2H); 7.76 (m, 1H); 7.47 (d, 2H); 7.27 (t, 2H); 4.60 (s, 2H); 4.20 (d, 2H); 4.01 (s, 4H); 3.65 (m, 2H); 3.37 (m, 2H); 2.89 (m, 6H).

EXAMPLE 61

N-[[4-(4,5-dihydro-1H-imidazol-2-yl)phenyl]methyl]-N-methyl-2-[2-[methyl[[4-(trifluoromethoxy)phenyl]sulphonyl]amino]-ethoxy]acetamide, trifluoroacetate (colourless oil, yield=67%).
$^1$H NMR (250 MHz, DMSO) δ: 10.51 (s, 2H); 7.91 (t, 4H); 7.59 (d, 2H); 7.48 (d, 2H); 4.60 (s, 2H); 4.20 (d, 2H); 4.01 (s, 4H); 3.61 (m, 2H); 3.21 (m, 2H); 2.75 (m, 6H).

EXAMPLE 62

2-[2-[[(2,5-dichlorothien-3-yl)sulphonyl]methylamino]ethoxy]-N-[[4-(4,5-dihydro-1H-imidazol-2-yl)phenyl]methyl]-N-methyl-acetamide, trifluoroacetate (white solid, yield=99%).
M.Pt.=60° C.

EXAMPLE 63

N-[[4-(4,5-dihydro-1H-imidazol-2-yl)phenyl]methyl]-N-methyl-2-[2-[methyl[(3-methylphenyl)sulphonyl]amino]ethoxy]acetamide, trifluoroacetate (colourless oil, yield=68%).
$^1$H NMR (250 MHz, DMSO) δ: 10.48 (s, 2H); 7.88 (m, 2H); 7.61 (m, 2H); 7.51 (m, 4H); 4.63 (s, 2H); 4.20 (d, 2H); 4.01 (s, 4H); 3.62 (m, 2H); 3.09 (m, 2H); 2.76 (m, 6H); 2.40 (s, 3H).

EXAMPLE 64

N-[[4-(4,5-dihydro-1H-imidazol-2-yl)phenyl]methyl]-N-methyl-2-[2-[methyl(1-naphthalenylsulphonyl)amino]ethoxy]acetamide, trifluoroacetate (white solid, yield=99%).
M.Pt.=66° C.

EXAMPLE 65

N-[[4-(4,5-dihydro-1H-imidazol-2-yl)phenyl]methyl]-N-methyl-2-[2-[methyl[[3-(trifluoromethyl)phenyl]sulphonyl]amino]-ethoxy]acetamide, trifluoroacetate (white solid, yield=99%).
M.Pt.=60° C.

EXAMPLE 66

2-[2-[[(4-chloro-3-methylphenyl)sulphonyl]methylamino]ethoxy]-N-[[4-(4,5-dihydro-1H-imidazol-2-yl)phenyl]methyl]-N-methylacetamide, trifluoroacetate (white solid, yield=59%).
M.Pt.=60° C.

EXAMPLE 67

2-[2-[[(2,4-difluorophenyl)sulphonyl]methylamino]ethoxy]-N-[[4-(4,5-dihydro-1H-imidazol-2-yl)phenyl]methyl]-N-methyl-acetamide, trifluoroacetate (colourless oil, yield=99%).
$^1$H NMR (250 MHz, DMSO) δ: 10.51 (s, 2H); 7.88 (m, 3H); 7.53 (m, 3H); 7.29 (m, 1H); 4.60 (s, 2H); 4.20 (d, 2H); 4.01 (s, 4H); 3.60 (m, 2H); 3.26 (m, 2H); 2.85 (m, 6H).

EXAMPLE 68

2-[2-[[(3-chlorophenyl)sulphonyl]methylamino]ethoxy]-N-[[4-(4,5-dihydro-1H-imidazol-2-yl)phenyl]methyl]-N-methyl-acetamide, trifluoroacetate (white solid, yield=99%).
M.Pt.=60° C.

PREPARATION CLXXIV 5-bromo-N-[(4-cyanophenyl)methyl]-N-methylpentanamide

A solution of 30.14 g (0.206 M) of 4-[(methylamino)methyl]benzonitrile is prepared in 500 ml of dichloromethane and 22.9 g (0.227 M) of triethylamine are added. The mixture is cooled with the aid of an ice bath and a solution of 41.1 g (0.206 M) of 5-bromopentanoyl chloride in 200 ml of dichloromethane is added dropwise. The reaction mixture is kept under agitation at ambient temperature for 5 hours and then hydrolysed over 300 ml of cold 1N hydrochloric acid. The organic phase is separated, washed with water, and then with a solution of sodium bicarbonate, and then with water and dried over magnesium sulphate. After concentration under reduced pressure, the expected product is obtained as a yellow oil (yield=97%).
$^1$H NMR (300 MHz, DMSO) δ: 7.80 (d, 2H); 7.39 (d, 2H); 4.62 (d, 2H); 3.50 (m, 2H); 2.81 and 2.50 (s, 3H); 2.41 (m, 2H); 1.80 (m, 2H); 1.64 (m, 2H).

PREPARATION CLXXV

N-[(4-cyanophenyl)methyl]-N-methyl-5-[methyl(phenylmethyl)-amino]pentanamide

A solution of 62.2 g (0.201 M) of the compound obtained according to preparation CLXXIV is prepared in 500 ml of acetonitrile and 24.4 g (0.201 M) of N-methyl-benzenemethanamine, and then 27.8 g (0.201 M) of potassium carbonate, are added at ambient temperature. The reaction mixture is agitated at 50° C. for 8 hours, and then for one night at ambient temperature. The solvent is then removed under reduced pressure and the residue of evaporation is taken up by 300 ml of dichloromethane. This organic phase is washed twice with water, and then dried over magnesium sulphate and concentrated under reduced pressure. The crude product is purified by chromatography on silica gel in eluting with the aid of a mixture of dichloromethane/methanol (95/5; v/v). 51.7 g of the expected compound are thus obtained as a yellow oil (yield=74%).
$^1$H NMR (250 MHz, DMSO) δ: 7.78 (m, 2H); 7.35 (m, 2H); 7.26 (m, 5H); 4.60 (d, 2H); 3.40 (d, 2H); 2.75 (d, 3H); 2.32 (m, 4H); 2.05 (d, 3H); 1.50 (m, 4H).

PREPARATION CLXXVI

[5-[[(4-cyanophenyl)methyl]methylamino]-5-oxopentyl]methylcarbamic acid, phenylmethyl ester 51.67 g (0.148 M) of the compound obtained according to preparation CLXXV are dissolved in 400 ml of dichloromethane and a solution of 42 ml (0.296 M) of benzyl chloroformate in 200 ml of dichloromethane is added progressively. The reaction mixture is kept under agitation for 16 hours at ambient temperature, and then hydrolysed over 300 ml of cold 0.5 N hydrochloric acid. The organic phase is separated and then washed with water to neutrality, dried over magnesium sulphate and concentrated under reduced pressure. This crude product is purified by chromatography on silica gel in eluting with a mixture of toluene/isopropanol (95/5; v/v). 51.6 g of the desired product are thus obtained as a yellow oil (yield=89%).
$^1$H NMR (250 MHz, DMSO) δ: 7.79 (m, 2H); 7.36 (m, 7H); 5.04 (d, 2H); 4.60 (d, 2H); 3.22 (m, 2H); 2.84 (m, 6H); 2.35 (m, 2H); 1.47 (m, 4H).

In operating analogously to Preparations II to IV, starting with the compound obtained according to Preparation CLXXVI, the following compounds are obtained:

PREPARATION CLXXVII

[5-[[[4-(4,5-dihydro-1H-imidazol-2-yl)phenyl]methyl]methylamino]-5-oxopentyl]methylcarbamic acid, 1,1-dimethylethyl ester (yellow oil, yield=94%).
$^1$H NMR (250 MHz, DMSO) δ: 7.78 (m, 2H); 7.30 (m, 5H); 7.22 (d, 2H); 6.83 (broad s, 1H); 5.04 (d, 2H); 4.50 (d, 2H); 3.64 (m, 4H); 3.26 (m, 2H); 2.82 (m, 6H); 2.38 (m, 2H); 1.48 (m, 4H).

PREPARATION CLXXVIII 4,5-dihydro-2-[4-[[methyl[5-[methyl[(phenylmethoxy)carbonyl]-amino]-1-oxopentyl]amino]methyl]phenyl]-1H-imidazole-1-carboxylic acid, 1,1-dimethylethyl ester (colourless oil, yield=95%).

PREPARATION CLXXIX 4,5-dihydro-2-[4-[[methyl[5-(methylamino)-1-oxo-pentyl]amino]methyl]phenyl]-1H-imidazole-1-carboxylic acid, 1,1-dimethylethyl ester (yellow oil, yield=90%).
$^1$H NMR (250 MHz, DMSO) δ: 7.43 (m, 2H); 7.20 (m, 2H); 4.56 (d, 2H); 3.84 (m, 4H); 2.87 (d, 3H); 2.42 (m, 4H); 2.29 (d, 3H); 1.49 (m, 4H); 1.18 (s, 9H).

In operating analogously to Preparation V, the following compounds are obtained:

PREPARATION CLXXX 4,5-dihydro-2-[4-[[methyl[5-[methyl[[2-(trifluoromethyl)phenyl]-sulphonyl]amino]-1-oxopentyl]amino]methyl]phenyl]-1H-imidazole-1-carboxylic acid, 1,1-dimethylethyl ester (colourless oil, yield=41%).
$^1$H NMR (250 MHz, DMSO) δ: 7.91 (m, 4H); 7.43 (dd, 2H); 7.21 (dd, 2H); 4.56 (d, 2H); 3.85 (m, 4H); 3.21 (m, 2H); 2.84 (m, 6H); 2.36 (m, 2H); 1.55 (m, 4H); 1.14 (s, 9H).

PREPARATION CLXXXI

2-[4-[[[5-[[(2,4-dichloro-5-methylphenyl)sulphonyl]methylamino]-1-oxopentyl]methylamino]methyl]phenyl]-4,5-dihydro-1H-imidazole-1-carboxylic acid, 1,1-dimethylethyl ester (white foam, yield=53%).
$^1$H NMR (250 MHz, DMSO) δ: 7.92 (d, 1H); 7.83 (d, 1H); 7.43 (dd, 2H); 7.20 (dd, 2H); 4.54 (d, 2H); 3.85 (m, 4H); 3.17 (m, 2H); 2.85 (m, 6H); 2.39 (s, 3H); 2.35 (m, 2H); 1.52 (m, 4H); 1.17 (s, 9H).

PREPARATION CLXXXII 4,5-dihydro-2-[4-[[methyl[5-[methyl[(3-methylphenyl)sulphonyl]-amino]-1-oxopentyl]amino]methyl]phenyl]-1H-imidazole-1-carboxylic acid, 1,1-dimethylethyl ester (colourless oil, yield=51%).
$^1$H NMR (250 MHz, DMSO) δ: 7.52 (m, 3H); 7.42 (dd, 2H); 7.21 dd, 2H); 4.56 (d, 2H); 3.85 (m, 4H); 2.90 (m, 2H); 2.83 (d, 3H); 2.62 (d, 3H); 2.40 (s, 2H); 2.35 (m, 2H); 1.52 (m, 4H); 1.18 (s, 9H).

PREPARATION CLXXXIII 4,5-dihydro-2-[4-[[[5-[[(4-methoxy-2,6-dimethylphenyl)sulphonyl]-methylamino]-1-oxopentyl]methylamino]methyl]phenyl]-1H-imidazole-1-carboxylic acid, 1,1-dimethylethyl ester (colourless oil, yield=20%).
$^1$H NMR (250 MHz, DMSO) δ: 7.42 (m, 2H); 7.19 (m, 2H); 6.80 (m, 2H); 4.53 (d, 2H); 3.85 (m, 4H); 3.78 (s, 3H); 3.02 (m, 2H); 2.82 (d, 3H); 2.58 (m, 2H); 2.26 (m, 2H); 1.49 (m, 4H); 1.17 (s, 9H).

PREPARATION CLXXXIV 4,5-dihydro-2-[4-[[methyl[5-[methyl[(2,3,4-trichlorophenyl)sulphonyl]amino]-1-oxopentyl]amino]methyl]phenyl]-1H-imidazole-1-carboxylic acid, 1,1-dimethylethyl ester (white solid, yield=62%)
M.Pt.=60° C.

PREPARATION CLXXXV 4,5-dihydro-2-[4-[[methyl[5-[methyl[(2-nitrophenyl)sulphonyl]-amino]-1-oxopentyl]amino]methyl]phenyl]-1H-imidazole-1-carboxylic acid, 1,1-dimethylethyl ester (white solid, yield=39%).
M.Pt.=60° C.

PREPARATION CLXXXVI

2-[4-[[[5-[[(2,4-dichlorophenyl)sulphonyl]methylamino]-1-oxopentyl]methylamino]methyl]phenyl]-4,5-dihydro-1H-imidazole-1-carboxylic acid, 1,1-dimethylethyl ester (colourless oil, yield=46%).
$^1$H NMR (250 MHz, DMSO) δ: 7.94 (m, 2H); 7.63 (m, 1H); 7.43 (dd, 2H); 7.20 (dd, 2H); 4.55 (d, 2H); 3.84 (m, 4H); 3.17 (m, 2H); 2.83 (m, 6H); 2.37 (m, 2H); 1.49 (m, 4H); 1.17 (s, 9H).

PREPARATION CLXXXVII

2-[4-[[[5-[[(2-chloro-3-methylphenyl)sulphonyl]methylamino]-1-oxopentyl]methylamino]methyl]phenyl]-4,5-dihydro-1H-imidazole-1-carboxylic acid, 1,1-dimethylethyl ester (colourless oil, yield=65%).
$^1$H NMR (250 MHz, DMSO) δ: 7.82 (m, 1H); 7.64 (m, 1H); 7.43 (m, 3H); 7.20 (dd, 2H); 4.54 (d, 2H); 3.86 (m, 4H); 3.18 (m, 2H); 2.84 (m, 6H); 2.48 (s, 3H); 2.35 (m, 2H); 1.51 (m, 4H); 1.18 (s, 9H).

In operating analogously to Example 1, the following compounds are obtained:

EXAMPLE 69

N-[[4-(4,5-dihydro-1H-imidazol-2-yl)phenyl]methyl]-N-methyl-5-[methyl[[2-(trifluoromethyl)phenyl]sulphonyl]amino]pentanamide, trifluoroacetate (amorphous solid, yield=99%).
$^1$H NMR (300 MHz, DMSO) δ: 10.50 (d, 2H); 8.02 (m, 1H); 7.92 (m, 5H); 7.46 (d, 2H); 4.66 (d, 2H); 4.01 (s, 4H); 3.22 (, 2H); 2.90 (m, 6H); 2.40 (m, 2H); 1.55 (m, 4H).

EXAMPLE 70

5-[[(2,4-dichloro-5-methylphenyl)sulphonyl]methylamino]-N-[[4-(4,5-dihydro-1H-imidazol-2-yl)phenyl]methyl]-N-methylpentanamide, trifluoroacetate (white solid, yield=99%).
M.Pt.=50° C.

EXAMPLE 71

N-[[4-(4,5-dihydro-1H-imidazol-2-yl)phenyl]methyl-N-methyl-5-[methyl[(3-methylphenyl)sulphonyl]amino]pentanamide, trifluoroacetate (white solid, yield=99%).
$^1$H NMR (300 MHz, DMSO) δ: 10.48 (d, 2H); 7.90 (dd, 2H); 7.52 (m, 6H); 4.66 (d, 2H); 4.01 (s, 4H); 2.93 (m, 5H); 2.62 (d, 3H); 2.41 (m, 5H); 1.53 (m, 4H).

EXAMPLE 72

N-[[4-(4,5-dihydro-1H-imidazol-2-yl)phenyl]methyl]-5-[[(4-methoxy-2,6-dimethylphenyl)sulphonyl]methylamino]-N-methyl-pentanamide, trifluoroacetate (white solid, yield=66%).
M.Pt.=60° C.

EXAMPLE 73

N-[[4-(4,5-dihydro-1H-imidazol-2-yl)phenyl]methyl-N-methyl-5-[methyl[(2,3,4-trichlorophenyl)sulphonyl]amino]pentanamide, trifluoroacetate (white solid, yield=84%).
M.Pt.=70° C.

EXAMPLE 74

N-[[4-(4,5-dihydro-1H-imidazol-2-yl)phenyl]methyl-N-methyl-5-[methyl[(2-nitrophenyl)sulphonyl]amino]pentanamide, trifluoroacetate (white solid, yield=79%).
M.Pt.=60° C.

EXAMPLE 75

5-[[(2,4-dichlorophenyl)sulphonyl]methylamino]-N-[[4-(4,5-dihydro-1H-imidazol-2-yl)phenyl]methyl]-N-methyl-pentanamide, trifluoroacetate (white solid, yield=99%).
M.Pt.=60° C.

EXAMPLE 76

5-[[(2-chloro-3-methylphenyl)sulphonyl]methylamino]-N-[[4-(4,5-dihydro-1H-imidazol-2-yl)phenyl]methyl]-N-methyl-pentanamide, trifluoroacetate (white solid, yield=93%).
M.Pt.=72° C.

PREPARATION CLXXXVIII

N-[(4-cyanophenyl)methyl]-5-[[(2,4-dichloro-3-methylphenyl)sulphonyl]methylamino]-N-methyl-pentanamide In operating analogously to Preparation VIII, starting with 4-[(methylamino)methyl]benzonitrile, the expected compound is obtained as a colourless oil (yield=84%).

$^1$H NMR (250 MHz, DMSO) δ: 7.83 (m, 3H); 7.65 (m, 1H); 7.39 (d, 2H); 4.60 (d, 2H); 3.22 (m, 2H); 2.85 (m, 6H); 2.50 (s, 3H); 2.38 (m, 2H); 1.53 (m, 4H).

EXAMPLE 77

N-[[4-[amino(hydroxyimino)methyl]phenyl]methyl]-5-[[(2,4-dichloro-3-methyl)phenyl]sulphonyl]methylamino]-N-methylpentanamide A solution of 2.51 g (5.2 mM) of the compound obtained according to preparation CLXXXVIII is prepared in 56 ml of dimethylsulphoxide and 1.90 g (27 mM) of hydroxylamine hydrochloride and 7.5 ml (54 mM) of triethylamine are added progressively, at ambient temperature. The mixture is kept under agitation at ambient temperature for 30 hours and then poured onto 250 ml of iced water. The mixture is extracted with ethyl acetate (twice) and the combined organic phases are washed with water and then dried over magnesium sulphate and concentrated under reduced pressure. 2.47 g of the expected product are thus obtained as white crystals (yield=92%).
M.Pt.=74° C.

PREPARATION CLXXXIX

N-[[4-[[(acetyloxy)imino]aminomethyl]phenyl]methyl]-5-[[(2,4-dichloro-3-methylphenyl)sulphonyl]methylamino]-N-methylpentanamide A solution of 1 g (1.95 mM) of the compound obtained according to Example 77 is prepared in 50 ml of dichloromethane and 0.59 g (5.82 mM) of acetic anhydride are added. The reaction mixture is agitated at ambient temperature for 20 hours and then concentrated under reduced pressure. The residue is taken up in 100 ml of ethyl acetate and the solution obtained is agitated for 15 min with a 5% aqueous solution of sodium carbonate. The aqueous phase is removed and the organic phase is washed with water, and then dried over magnesium sulphate and concentrated under reduced pressure. 1 g of the desired product is thus obtained as a colourless oil (yield=92%).
$^1$H NMR (250 MHz, DMSO) δ: 7.82 (t, 1H); 7.65 (m, 3H); 7.26 (d, 2H); 6.76 (broad s, 2H); 4.56 (d, 2H); 3.20 (m, 2H); 2.80 (m, 6H); 2.50 (s, 3H); 2.36 (m, 2H); 2.12 (s, 3H); 1.52 (m, 4H).

EXAMPLE 78

N-[[4-(aminoiminomethyl)phenyl]methyl]-5-[[(2,4-dichloro-3-methylphenyl)sulphonyl]methylamino]-N-methyl-pentanamide, trifluoroacetate 1 g (1.79 mM) of the compound obtained according to preparation CLXXXIX is dissolved in 50 ml of methanol and 200 mg of 5% palladium on carbon are added. The mixture is agitated under a hydrogen atmosphere, at atmospheric pressure and at ambient temperature, for 6 hours. The mixture is then filtered and the filtrate is concentrated under reduced pressure. The crude product is taken up in the hot with 10 ml of dioxan. The product which crystallised by cooling of the solution is separated off by filtration and dried under vacuum. The compound obtained is then purified by chromatography on silica gel RP 18 in using a mixture of acetonitrile/water/trifluoroacetic acid (50/49/1; v/v/v) as mobile phase. The pure fractions are concentrated under reduced pressure, taken up with ethanol, concentrated once again under reduced pressure and then taken up in solution in water and lyophilised. The expected product is thus obtained with a yield of 20%.

$^1$H NMR (300 MHz, DMSO) δ: 9.28 (m, 2H); 9.10 (m, 2H); 7.79 (m, 3H); 7.64 (m, 1H); 7.42 (d, 2H); 4.63 (d, 2H); 3.20 (m, 2H); 2.85 (m, 6H); 2.30 (m, 2H); 1.51 (m, 4H).

EXAMPLE 79

N-[[4-(4,5-dihydro-1H-imidazol-2-yl)phenyl]methyl]-2-[2-[[(4-methoxy-2,6-dimethylphenyl)sulphonyl]methylamino]ethoxy]-N-methyl-acetamide, fumarate A solution of 1 g of the compound obtained according to Example 49 is prepared in 20 ml of methanol and 2 g of basic IRA 400 resin are added. The mixture is agitated for 10 min and the resin is then separated off by filtration and the filtrate is concentrated under reduced pressure. 0.68 g of oil are thus obtained which is taken up in 2 ml of methanol. 157 mg of fumaric acid are then added and the mixture is agitated to dissolution. 20 ml of ethyl ether are then added. An oil is formed which is separated. This oil is taken up in 10 ml of water, the solution obtained is filtered and then lyophilised. 0.78 g of the expected compound are thus obtained as a fine white solid (yield=76%).
M.Pt.=88° C.

EXAMPLE 80

N-[[4-(4,5-dihydro-1-methyl-1H-imidazol-2-yl)phenyl]methyl]-N-methyl-4-[methyl[[2-(trifluoromethyl)phenyl]sulphonyl]amino]-(2E)-2-butenamide In operating analogously to Preparation VIII, starting with the acid obtained according to Preparation XCIV and the amine obtained according to Preparation CXVI, the expected product is obtained as a colourless oil (yield=48%).

$^1$H NMR (300 MHz, DMSO) δ: 8.04 (m, 2H); 7.90 (m, 2H); 7.52 (t, 2H); 7.23 (m, 2H); 6.60 (m, 2H); 4.66 and 4.59 (2s, 2H); 4.09 (d, 1H); 4.02 (m, 1H); 3.70 (t, 2H); 3.36 (t, 2H); 3.06 and 3.03 (2s, 3H); 2.99 and 2.72 (2s, 3H); 2.68 (s, 3H).

EXAMPLE 81

N-[[4-(4,5-dihydro-1-methyl-1H-imidazol-2-yl)phenyl]methyl]-N-methyl-4-[methyl[[2-(trifluoromethyl)phenyl]sulphonyl]amino]-(2E)-2-butenamide, fumarate In operating analogously to Example 79, starting with the compound obtained according to Example 80, the expected product is obtained as a white solid
(yield=89%).
M.Pt.=76-78° C.

PREPARATION XCC

2-[4-[[[(2E)-4-[[(2,3-dichlorophenyl)sulphonyl]methylamino]-1-oxo-2-butenyl]methylamino]methyl]-3-fluorophenyl]-4,5-dihydro-1H-imidazole-1-carboxylic acid, 1,1-dimethylethyl ester In operating analogously to Preparation VIII, starting with the acid obtained according to Preparation XXXVII and the amine obtained according to Preparation CXL, the expected product is obtained as a yellow oil (yield=47%).

$^1$H NMR (300 MHz, DMSO) δ: 7.99 (m, 2H); 7.58 (m, 1H); 7.26 (m, 3H); 6.59 (m, 2H); 4.65 (d, 2H); 4.03 (m, 2H); 3.85 (m, 4H); 3.17 and 2.86 (2s, 3H); 3.00 (s, 3H); 1.20 (s, 9H).

EXAMPLE 82

4-[[(2,3-dichlorophenyl)sulphonyl]methylamino]-N-[[4-(4,5-dihydro-1H-imidazol-2-yl)-2-fluorophenyl]methyl]-N-methyl-(2E)-2-butenamide, trifluoroacetate In operating analogously to Example 1, starting with the compound obtained according to Preparation XCC, the expected product is obtained as a white ecru solid (yield=79%).
M.Pt.=80° C.

PREPARATION XCCI

2-[4-[[[(2E)-4-[[(2-chlorophenyl)sulphonyl]methylamino]-1-oxo-2-butenyl]methylamino]methyl]-3-fluorophenyl]-4,5-dihydro-1H imidazole-1-carboxylic acid, 1,1-dimethylethyl ester In operating analogously to Preparation XCC, starting with the acid obtained according to Preparation XXXIII, the expected product is obtained as a colourless oil (yield=69%).

$^1$H NMR (250 MHz, DMSO) δ: 8.00 (m, 1H); 7.66 (m, 2H); 7.56 (m, 1H); 7.26 (m, 3H); 6.59 (m, 2H); 4.65 (d, 2H); 4.05 (d, 1H); 3.98 (d, 1H); 3.86 (m, 4H); 3.00 and 2.72 (2s, 3H); 2.83 (d, 3H); 1.20 (s, 9H).

EXAMPLE 83

4-[[(2-chlorophenyl)sulphonyl]methylamino]-N-[[4-(4,5-dihydro-1H-imidazol-2-yl)-2-fluorophenyl]methyl]-N-methyl-(2E)-2-butenamide, trifluoroacetate In operating analogously to Example 1, starting with the compound obtained according to Preparation XCCI, the expected product is obtained as a white ecru solid (yield=62%).
M.Pt.=75° C.

PREPARATION XCCII 4-methoxy-N,2,6-trimethylbenzenesulphonamide

In operating analogously to Preparation V, starting with 4-methoxy-2,6-dimethylbenzenesulphonyl chloride, the expected compound is obtained as a white solid (yield=96%).
M.Pt.=131° C.

PREPARATION XCCIII

3-[[(4-methoxy-2,6-dimethylphenyl)sulphonyl]methylamino]-propanoic acid, ethyl ester In operating analogously to Preparation VI, starting with the compound obtained according to Preparation XCCII and ethyl 3-bromopropanoate, the expected product is obtained as a yellow oil (yield=97%).

$^1$H NMR (250 MHz, CDCl$_3$) δ: 6.63 (s, 2H); 4.09 (q, 2H); 3.81 (s, 3H); 3.45 (t, 2H); 2.74 (s, 3H); 2.62 (m, 2H); 2.60 (s, 6H); 1.23 (t, 3H).

PREPARATION XCCIV

3-[[(4-methoxy-2,6-dimethylphenyl)sulphonyl]methylamino]-propanoic acid

In operating analogously to Preparation VII, starting with the compound obtained according to Preparation XCCIII, the expected acid is obtained as a white solid (yield=97%). M.Pt.=103° C.

PREPARATION XCCV 4,5-dihydro-2-[4-[[[3-[[(4-methoxy-2,6-dimethylphenyl)sulphonyl]methylamino]-1-oxopropyl]methylamino]methyl]phenyl]-1H-imidazole-1-carboxylic acid, 1,1-dimethylethyl ester In operating analogously to Preparation VIII, starting with the acid obtained according to Preparation XCCIV and the amine obtained according to Preparation IV, the expected product is obtained as a colourless oil (yield=61%).
$^1$H NMR (250 MHz, CDCl$_3$) δ: 7.52 (m, 2H); 7.27 (m, 2H); 6.66 (d, 2H); 4.57 (d, 2H); 4.00 (m, 4H); 3.85 (d, 3H); 3.60 (m, 2H); 2.90 (d, 3H); 2.78 (d, 3H); 2.77 (m, 2H); 2.62 (d, 6H); 1.28 (d, 9H).

EXAMPLE 84

N-[[4-(4,5-dihydro-1H-imidazol-2-yl)phenyl]methyl]-3-[[(4-methoxy-2,6-dimethylphenyl)sulphonyl] methylamino]-N-methyl-propanamide, trifluoroacetate In operating analogously to Example 1, starting with the compound obtained according to Preparation XCCV, the expected product is obtained as a white solid (yield=99%). M.Pt.=59° C.

In operating analogously to Preparations CXXXVI, I, II, III and IV, starting with 4-(bromomethyl)-3-chlorobenzonitrile, the following 5 compounds are obtained respectively:

PREPARATION XCCVI 4-cyano-2-chloro-N-methylbenzenemethanamine (Colourless oil, yield=89%).
$^1$H NMR (300 MHz, DMSO) δ: 7.99 (d, 1H); 7.83 (dd, 1H); 7.71 (d, 1H); 3.76 (s, 2H); 2.29 (s, 3H).

PREPARATION XCCVII

[(2-chloro-4-cyanophenyl)methyl]methylcarbamic acid, phenylmethyl ester (Colourless oil, yield=99%).
$^1$H NMR (250 MHz, DMSO) δ: 8.00 (s, 1H); 7.80 (m, 1H); 7.25 (m, 6H); 5.10 (d, 2H); 4.59 (s, 2H); 2.94 (s, 3H).

PREPARATION XCCVIII

[[2-chloro-4-(4,5-dihydro-1H-imidazol-2-yl)phenyl]methyl]methylcarbamic acid, phenylmethyl ester (Colourless oil, yield=99%).

PREPARATION ICC

2-[3-chloro-4-[[methyl[(phenylmethoxy)carbonyl] amino]-methyl]phenyl]-4,5-dihydro-1H-imidazole-1-carboxylic acid, 1,1-dimethylethyl ester (Yellow oil, yield=94%).
$^1$H NMR (250 MHz, DMSO) δ: 7.51 (d, 1H); 7.41 (m, 7H); 5.10 (d, 2H); 4.57 (s, 2H); 3.85 (m, 4H); 2.89 (s, 3H); 1.14 (s, 9H).

PREPARATION CC

2-[3-chloro-4-[(methylamino)methyl]phenyl]-4,5-dihydro-1H-imidazole-1-carboxylic acid, 1,1-dimethylethyl ester (Colourless oil, yield=11%).
$^1$H NMR (250 MHz, DMSO) δ: 7.51 (d, 1H); 7.43 (d, 1H); 7.40 (dd, 1H); 3.85 (m, 4H); 3.74 (s, 2H); 2.31 (s, 3H); 1.19 (s, 9H).

In operating analogously to Preparations VI and VII, starting with the sulphonamide obtained according to Preparation XCCII and ethyl 5-bromopentanoate, the following compounds are obtained:

PREPARATION CCI

5-[[(4-methoxy-2,6-dimethylphenyl)sulphonyl]methylamino]-pentanoic acid, ethyl ester (Colourless oil, yield=58%).
$^1$H NMR (300 MHz, CDCl$_3$) δ: 6.63 (s, 2H); 4.11 (q, 2H); 3.81 (s, 3H); 3.10 (t, 2H); 2.70 (s, 3H); 2.61 (s, 6H); 2.24 (t, 2H); 1.55 (m, 4H); 1.25 (t, 3H).

PREPARATION CCII

5-[[(4-methoxy-2,6-dimethylphenyl)sulphonyl]methylamino]-pentanoic acid (White pasty solid, yield=99%).
M.Pt.=80-84° C.

PREPARATION CCIII

2-[3-chloro-4-[[[5-[[(4-methoxy-2,6-dimethylphenyl)sulphonyl]-methylamino]-1-oxopentyl]methylamino]methyl]phenyl]-4,5-dihydro-1H-imidazole-1-carboxylic acid, 1,1-dimethylethyl ester In operating analogously to Preparation VIII, starting with the acid obtained according to Preparation CCII and the amine obtained according to Preparation CC, the expected product is obtained as an oil which is treated without further purification.

EXAMPLE 85

N-[[2-chloro-4-(4,5-dihydro-1H-imidazol-2-yl)phenyl]methyl]-5-[[(4-methoxy-2,6-dimethylphenyl) sulphonyl]methylamino]-N-methylpentanamide 234 mg (3.7 mM) of the compound obtained according to preparation CCIII are added to a mixture of 1.5 ml of trifluoroacetic acid in 2.5 ml of DCM. This reaction mixture is agitated for one hour at ambient temperature and this mixture is then concentrated under reduced pressure. The residue is then purified by chromatography on silica gel in eluting with the aid of a mixture of DC/methanol/aquous ammonia (120/10/0.02). 186 mg of the expected product are thus obtained as a colourless oil (yield: 94%).

$^1$H NMR (300 MHz, DMSO) δ: 7.90 (d, 1H); 7.75 (dd, 1H); 7.18 (broad s, 1H); 7.15 (t, 1H); 6.79 (d, 2H); 4.60 (d, 2H); 3.79 (s, 3H); 3.61 (s, 4H); 3.01 (t, 2H); 2.94 and 2.82 (2s, 3H); 2.63 and 2.59 (2s, 3H); 2.51 (s, 6H); 2.37 and 2.17 (2t, 2H); 1.48 (m, 4H).

EXAMPLE 86

N-[[2-chloro-4-(4,5-dihydro-1H-imidazol-2-yl)phenyl]methyl]-5-[[(4-methoxy-2,6-dimethylphenyl)sulphonyl]methylamino]-N-methylpentanamide, fumarate In operating analogously to Example 79, starting with the compound obtained according to Example 85, the expected salt is obtained as a white solid (yield=98%).

M.Pt.=60° C.

PREPARATION CCIV

2-[2-[methyl[[2-(trifluoromethyl)phenyl]sulphonyl]amino]-ethoxy]acetic acid, 1,1-dimethylethyl ester In operating analogously to Preparation VI, starting with the compound obtained according to Preparation LXXXIX and t-butyl (2-iodoethoxy)acetate, the expected product is obtained as a colourless oil (yield=72%).

$^1$H NMR (250 MHz, DMSO) δ: 8.02 (m, 2H); 7.88 (m, 2H); 3.97 (s, 2H); 3.63 (t, 2H); 3.45 (t, 2H); 2.95 (s, 3H); 1.40 (s, 9H).

PREPARATION CCV

2-[2-[methyl[[2-(trifluoromethyl)phenyl]sulphonyl]amino]-ethoxy]acetic acid

In operating analogously to Preparation VII, starting with the compound obtained according to Preparation CCIV, the expected product is obtained as a colourless oil (yield=94%).

$^1$H NMR (250 MHz, DMSO) δ: 8.03 (m, 2H); 7.86 (m, 2H); 4.01 (s, 2H); 3.65 (t, 2H); 3.45 (t, 2H); 2.95 (s, 3H).

EXAMPLE 87

N-[[4-(4,5-dihydro-1-methyl-1H-imidazol-2-yl)phenyl]methyl]-N-methyl-2-[2-[methyl[[2-(trifluoromethyl)phenyl]sulphonyl]amino]-ethoxy]acetamide In operating analogously to Preparation VIII, starting with the acid obtained according to Preparation CCV and the amine obtained according to Preparation CXVI, the expected product is obtained as a yellow oil (yield=62%).

$^1$H NMR (300 MHz, DMSO) δ: 8.04 (m, 2H); 7.87 (m, 2H); 7.50 (m, 2H); 7.23 (d, 2H); 4.54 (s, 2H); 4.25 (d, 2H); 3.67 (m, 4H); 3.40 (m, 4H); 2.95 (d, 3H); 2.93 (d, 3H); 2.80 (s, 3H).

EXAMPLE 88

N-[[4-(4,5-dihydro-1-methyl-1H-imidazol-2-yl)phenyl]methyl]-N-methyl-2-[2-[methyl[[2-(trifluoromethyl)phenyl]sulphonyl]amino]-ethoxy]acetamide, fumarate In operating analogously to Example 79, starting with the compound obtained according to Example 87, the expected product is obtained as a white solid (yield=100%).

M.Pt.=62° C.

PREPARATION CCVI

2-[3-chloro-4-[[[[2-[[(2-chlorophenyl)sulphonyl]methylamino]-ethoxy]acetyl]methylamino]-methyl]phenyl]-4,5-dihydro-1H-imidazole-1-carboxylic acid, 1,1-dimethylethyl ester In operating analogously to Preparation VIII, starting with the acid obtained according to Preparation CXXXI and the amine obtained according to Preparation CC, the expected product is obtained as a colourless oil (yield=41%).

$^1$H NMR (250 MHz, DMSO) δ: 7.99 (m, 1H); 7.62 (m, 2H); 7.52 (m, 3H); 7.23 (m, 1H); 4.58 (s, 2H); 4.28 and 4.12 (2s, 2H); 3.85 (s, 4H); 3.58 (m, 2H); 3.42 (m, 2H); 2.91 and 2.86 (2s, 3H); 2.90 and 2.83 (2s, 3H); 1.20 (s, 9H).

EXAMPLE 89

N-[[2-chloro-4-(4,5-dihydro-1H-imidazol-2-yl)phenyl]methyl]-2-[2-[[(2-chlorophenyl)sulphonyl]methylamino]ethoxy]-N-methylacetamide, trifluoroacetate In operating analogously to Example 1, starting with the product obtained according to Preparation CCVI, the expected product is obtained as a pink solid (yield=99%).

$^1$H NMR (250 MHz, DMSO) δ: 8.08 (m, 1H); 7.99 (m, 2H); 7.68 (m, 2H); 7.57 (m, 1H); 7.53 (d, 1H); 4.67 (d, 2H); 4.32 and 4.12 (2s, 2H); 4.02 (s, 4H); 3.67 and 3.54 (2t, 2H); 3.46 and 3.26 (2t, 2H); 2.98 (s, 3H); 2.90 (s, 3H).

PREPARATION CCVII 4-methoxy-2,6,N-trimethyl-N-(2-hydroxyethyl)benzenesulphonamide In operating analogously to Preparation V, starting with 2,6-dimethyl-4-methoxybenzenesulphonyl chloride and 2-(N-methylamino)ethanol, the expected sulphonamide is obtained as a colourless oil (yield=95%).

$^1$H NMR (300 MHz, DMSO) δ: 6.80 (s, 2H); 4.70 (t, 1H); 3.80 (s, 3H); 3.47 (t, 2H); 3.09 (t, 2H); 2.69 (s, 3H); 2.53 (s, 6H).

In operating analogously to Preparations CXXII and LXXVIII, starting with the compound obtained according to Preparation CCVII, the 2 following compounds are obtained:

PREPARATION CCVIII

[2-[[(4-methoxy-2,6-dimethylphenyl)sulphonyl]methylamino]-ethoxy]acetic acid, 1,1-dimethylethyl ester (Colourless oil; yield=94%)
$^1$H NMR (250 MHz, DMSO) δ: 6.80 (s, 2H); 3.89 (s, 2H); 3.79 (s, 3H); 3.55 (t, 2H); 3.21 (t, 2H); 2.70 (s, 3H); 2.50 (s, 6H); 1.41 (s, 9H).

PREPARATION CCIX

[2-[[(4-methoxy-2,6-dimethylphenyl)sulphonyl]methylamino]-ethoxy]acetic acid (White solid; yield=68%)
M.Pt.=85° C.

PREPARATION CCX

2-[3-chloro-4-[[[[2-[[(4-methoxy-2,6-dimethylphenyl)sulphonyl]-methylamino]ethoxy]acetyl]methylamino]methyl]phenyl]-4,5-dihydro-1H-imidazole-1-carboxylic acid, 1,1-dimethylethyl ester In operating analogously to Preparation VIII, starting with the compounds obtained according to Preparations CCIX and CC, the expected product is obtained as a colourless oil (yield=57%).
$^1$H NMR (300 MHz, DMSO) δ: 7.55 (d, 1H); 7.41 (dd, 1H); 7.21 (m, 1H); 6.80 (d, 2H); 4.57 (s, 2H); 4.22 and 4.08 (2s, 2H); 3.85 (m, 4H); 3.80 (d, 3H); 3.59 and 3.52 (2t, 2H); 3.27 and 3.16 (2t, 2H); 2.88 and 2.79 (2s, 3H); 2.71 and 2.66 (2s, 3H); 2.53 (s, 6H); 1.20 (s, 9H).

EXAMPLE 90

N-[[2-chloro-4-(4,5-dihydro-1H-imidazol-2-yl)phenyl]methyl]-2-[2-[[(4-methoxy-2,6-dimethylphenyl)sulphonyl]methylamino]ethoxy]-N-methyl-acetamide, trifluoroacetate In operating analogously to Example 1, starting with the compound obtained according to preparation CCX, the expected product is obtained as a pink solid
(yield=94%).
M.Pt.=65° C.

PREPARATION CCXI

[(4-cyanophenyl)methyl][methyl]carbamic acid, 1,1-dimethylethyl ester

In operating analogously to Preparation III, starting with [(4-cyanophenyl)methyl]methanamine, the expected product is obtained as a yellow oil (yield=92%).
$^1$H NMR (300 MHz, DMSO) δ: 7.83 (d, 2H); 7.40 (d, 2H); 4.46 (s, 2H); 2.79 (s, 3H); 1.38 (m, 9H).

PREPARATION CCXII

[[4-[4,5-dihydro-1-(1-methylethyl)-1H-imidazol-2-yl]phenyl]methyl]-methylcarbamic acid, 1,1-dimethylethyl ester In operating analogously to Preparation II, starting with the compound obtained according to Preparation CCXI and N-(1-methylethyl)ethylenediamine, the expected product is obtained as a thick yellow oil (yield=99%).
$^1$H NMR (300 MHz, DMSO) δ: 7.47 (d, 2H); 7.30 (d, 2H); 4.41 (s, 2H); 3.75 (m, 3H); 3.48 (t, 2H); 2.79 (s, 3H); 1.38 (s, 9H); 1.03 (d, 6H).

PREPARATION CCXIII 1-(1-methylethyl)-2-[4-(methylaminomethyl)phenyl]-4,5-dihydro-1H-imidazole In operating analogously to Example 1, starting with the compound obtained according to Preparation CCXII, the expected product is obtained as a yellow paste (yield=99%).
$^1$H NMR (250 MHz, DMSO) δ: 10.5 (s, 1H); 9.15 (broad s, 2H); 7.70 (s, 4H); 4.27 (t, 2H); 4.01 (m, 4H); 3.85 (m, 1H); 2.61 (t, 3H); 1.25 (d, 6H).

EXAMPLE 91

N-[[4-(4,5-dihydro-1-(1-methylethyl)-1H-imidazol-2-yl)phenyl]-methyl]-2-[2-[[(4-methoxy-2,6-dimethylphenyl)sulphonyl]methylamino]ethoxy]-N-methyl-acetamide In operating analogously to Preparation VIII, starting with the acid obtained according to Preparation CCIX and the amine obtained according to Preparation CCXIII, the expected product is obtained as a colourless oil (yield=36%).
$^1$H NMR (250 MHz, DMSO) δ: 7.40 (m, 2H); 7.24 (m, 2H); 6.80 (s, 2H); 4.51 (s, 2H); 4.18 and 4.12 (2s, 2H); 3.80 (s, 3H); 3.66 (m, 5H); 3.30 (m, 4H); 2.80 and 2.77 (2s, 3H); 2.70 and 2.66 (2s, 3H); 2.53 (s, 6H); 0.96 (d, 6H).

EXAMPLE 92

N-[[4-(4,5-dihydro-1-(1-methylethyl)-1H-imidazol-2-yl)phenyl]-methyl]-2-[2-[[(4-methoxy-2,6-dimethylphenyl)sulphonyl]-methylamino]ethoxy]-N-methyl-acetamide, fumarate In operating analogously to Example 79, starting with the compound obtained according to Example 91, the expected product is obtained as a cream solid
(yield=99%).
M.Pt.=106° C.

In operating analogously to Preparations CCXI to CCXIII, the following 3 compounds are obtained:

PREPARATION CCXIV

[(2-chloro-4-cyanophenyl)methyl]methylcarbamic acid, 1,1-dimethylethyl ester (White solid; yield=72%).
M.Pt.=86-87° C.

PREPARATION CCXV

[[2-chloro-4-(4,5-dihydro-1-methyl-1H-imidazol-2-yl)phenyl]methyl]-methylcarbamic acid, 1,1-dimethylethyl ester (Yellow oil; yield=66%).
$^1$H NMR (300 MHz, DMSO) δ: 7.56 (s, 1H); 7.51 (d, 1H); 7.22 (d, 1H); 4.49 (s, 2H); 3.73 (t, 2H); 3.38 (t, 2H); 2.84 (s, 3H); 2.71 (s, 3H); 1.40 (d, 9H).

PREPARATION CCXVI 1-methyl-2-[3-chloro-4-(methylaminomethyl)phenyl]-4,5-dihydro-1H-imidazole (Beige solid; yield=92%)
M.Pt.=94-98° C.

EXAMPLE 93

N-[[2-chloro-4-(4,5-dihydro-1-methyl-1H-imidazol-2-yl)phenyl]-methyl]-2-[2-[[(4-methoxy-2,6-dimethylphenyl)sulphonyl]methylamino]ethoxy]-N-methylacetamide In operating analogously to Preparation VIII, starting with the compounds obtained according to Preparations CCIX and CCXVI, the expected product is obtained as a white paste (yield=53%).
$^1$H NMR (300 MHz, DMSO) δ: 7.60 (s, 1H); 7.50 (m, 1H); 7.25 (d, 1H); 6.80 (d, 2H); 4.57 (s, 2H); 4.27 and 4.08 (2s, 2H); 3.78 (s, 3H); 3.70 (t, 2H); 3.60 (t, 2H); 3.40 (t, 2H); 3.25 (t, 2H); 2.92 and 2.81 (2s, 3H); 2.74 (s, 3H); 2.71 and 2.64 (2s, 3H); 2.51 (d, 6H).

EXAMPLE 94

N-[[2-chloro-4-(4,5-dihydro-1-methyl-1H-imidazol-2-yl)phenyl]-methyl]-2-[2-[[(4-methoxy-2,6-dimethylphenyl)sulphonyl]methylamino]ethoxy]-N-methylacetamide, fumarate In operating analogously to Example 79, starting with the compound obtained according to Example 93, the expected product is obtained as a white solid
(yield=99%).
M.Pt.=65-68° C.

EXAMPLE 95

N-[[2-chloro-4-(4,5-dihydro-1-methyl-1H-imidazol-2-yl)phenyl]-methyl]-N-methyl-2-[2-[methyl[[2-(trifluoromethyl)phenyl]-sulphonyl]amino]ethoxy]acetamide In operating analogously to Preparation VIII, starting with the compounds obtained according to Preparations CCV and CCXVI, the expected product is obtained as a white oil (yield=41%).
$^1$H NMR (300 MHz, DMSO) δ: 8.01 (m, 2H); 7.86 (m, 2H); 7.64 (s, 1H); 7.49 (m, 1H); 7.30 (m, 1H); 4.60 (s, 2H); 4.33 and 4.16 (2s, 2H); 3.70 (m, 4H); 3.49 (m, 4H); 2.97 and 2.89 (2s, 3H); 2.96 and 2.84 (2s, 3H); 2.79 and 2.76 (2s, 3H).

EXAMPLE 96

N-[[2-chloro-4-(4,5-dihydro-1-methyl-1H-imidazol-2-yl)phenyl]-methyl]-N-methyl-2-[2-[methyl[[2-(trifluoromethyl)phenyl]-sulphonyl]amino]ethoxy]acetamide, fumarate In operating analogously to Example 79, starting with the compound obtained according to Example 95, the expected product is obtained as a white solid
(yield=99%).
M.Pt.=55° C.

In operating analogously to Preparations CCVII to CCIX, the following 3 compounds are obtained:

PREPARATION CCXVII 2-cyano-N-methyl-N-(2-hydroxyethyl)benzenesulphonamide (white oil, yield=90%).
$^1$H NMR (300 MHz, DMSO) δ: 7.93 (d, 1H); 7.88 (d, 1H); 7.85 (m, 2H); 4.80 (s, 1H); 3.50 (q, 2H); 3.24 (t, 2H); 2.87 (s, 3H).

PREPARATION CCXVIII

[2-[[(2-cyanophenyl)sulphonyl]methylamino]ethoxy]acetic acid, 1,1-dimethylethyl ester (Yellow oil; yield=87%)
$^1$H NMR (300 MHz, DMSO) δ: 8.13 (d, 1H); 8.02 (d, 1H); 7.90 (m, 2H); 3.90 (s, 2H); 3.59 (t, 2H); 3.37 (t, 2H); 2.90 (s, 3H); 1.41 (s, 9H).

PREPARATION CCXIX

[2-[[(2-cyanophenyl)sulphonyl]methylamino]ethoxy]acetic acid (White solid; yield=99%)
$^1$H NMR (300 MHz, DMSO) δ: 8.13 (d, 1H); 8.02 (d, 1H); 7.80 (m, 2H); 3.93 (s, 2H); 3.60 (t, 2H); 3.77 (t, 2H); 2.90 (s, 3H).

EXAMPLE 97

2-[2-[[(2-cyanophenyl)sulphonyl]methylamino]ethoxy]-N-[[4-(4,5-dihydro-1-methyl-1H-imidazol-2-yl)phenyl]methyl]-N-methylacetamide In operating analogously to Preparation VIII, starting with the compounds obtained according to Preparations CXVI and CCXIX, the expected product is obtained as a yellow oil (yield=57%).
$^1$H NMR (300 MHz, DMSO) δ: 8.11 (m, 2H); 7.88 (m, 2H); 7.50 (m, 2H); 7.28 (m, 2H); 4.51 (s, 2H); 4.20 and 4.13 (2s, 2H); 3.60 (m, 4H); 3.40 (m, 4H); 2.90 and 2.87 (2s, 3H); 2.85 and 2.78 (2s, 3H); 2.70 (s, 3H).

EXAMPLE 98

2-[2-[[(2-cyanophenyl)sulphonyl]methylamino]ethoxy]-N-[[4-(4,5-dihydro-1-methyl-1H-imidazol-2-yl)phenyl]methyl]-N-methylacetamide, fumarate In operating analogously to Example 79, starting with the compound obtained according to Example 97, the expected product is obtained as a white solid
(yield=90%).
M.Pt.=59° C.

In operating analogously to Preparations CCVII to CCIX, the following 3 compounds are obtained:

PREPARATION CCXX 2-chloro-4-methoxy-N-methyl-N-(2-hydroxyethyl) benzenesulphonamide (Colourless oil, yield=99%)
$^1$H NMR (250 MHz, DMSO) δ: 7.90 (d, 1H); 7.24 (d, 1H); 7.06 (dd, 1H); 4.76 (t, 1H); 3.86 (s, 3H); 3.52 (q, 2H); 3.19 (t, 2H); 2.84 (s, 3H).

PREPARATION CCXXI

[2-[[(2-chloro-4-methoxyphenyl)sulphonyl]methylamino]-ethoxy]acetic acid, 1,1-dimethylethyl ester (Colourless oil; yield=96%)
$^1$H NMR (300 MHz, DMSO) δ: 7.90 (d, 1H); 7.24 (d, 1H); 7.06 (dd, 1H); 4.03 (s, 2H); 3.86 (s, 3H); 3.58 (t, 2H); 3.34 (t, 2H); 2.85 (s, 3H); 1.42 (s, 9H).

PREPARATION CCXXII

[2-[[(2-chloro-4-methoxyphenyl)sulphonyl]methylamino]ethoxy]-acetic acid (Colourless oil; yield=99%)
$^1$H NMR (300 MHz, DMSO) δ: 7.91 (d, 1H); 7.24 (d, 1H); 7.07 (dd, 1H); 3.99 (s, 2H); 3.86 (s, 3H); 3.60 (t, 2H); 3.34 (t, 2H); 2.84 (s, 3H).

In operating analogously to Examples 97 and 98, starting with the acid obtained according to Preparation CCXXII, the 2 following compounds are obtained:

EXAMPLE 99

2-[2-[[(2-chloro-4-methoxyphenyl)sulphonyl]methylamino]ethoxy]-N-[[4-(4,5-dihydro-1-methyl-1H-imidazol-2-yl)phenyl]methyl]-N-methyl-acetamide (Colourless oil; yield=27%)
$^1$H NMR (300 MHz, DMSO) δ: 7.91 (d, 1H); 7.48 (m, 2H); 7.24 (m, 3H); 7.10 (dd, 1H); 4.52 (s, 2H); 4.23 and 4.18 (2s, 2H); 3.85 (s, 3H); 3.68 (m, 4H); 3.39 (m, 4H); 2.87 and 2.81 (2s, 3H); 2.84 and 2.80 (2s, 3H); 2.69 (s, 3H).

EXAMPLE 100

2-[2-[[(2-chloro-4-methoxyphenyl)sulphonyl]methylamino]ethoxy]-N-[[4-(4,5-dihydro-1-methyl-1H-imidazol-2-yl)phenyl]methyl]-N-methyl-acetamide, fumarate (White solid; yield=87%)
M.Pt.=50° C.

PREPARATION CCXXIII

N-(2-cyanoethyl)-N-methyl-2-(trifluoromethyl)benzenesulphonamide

In operating analogously to Preparation V, starting with 2-(trifluoromethyl)benzenesulphonyl chloride and 3-(methylamino)propionitrile, the expected product is obtained as a yellow oil (yield=98%).
$^1$H NMR (250 MHz, DMSO) δ: 8.02 (m, 2H); 7.90 (m, 2H); 3.55 (t, 2H); 2.29 (s, 3H); 2.86 (t, 2H).

PREPARATION CCXXIV

3-[methyl[[(2-(trifluoromethyl)phenyl]sulphonyl]amino]propanoic acid 140 mg (0.48 mM) of the compound obtained according to Preparation CCXIII is mixed with 3 ml of 10N hydrochloric acid and this mixture is agitated under smooth reflux for 3 hours. The reaction mixture is then cooled, diluted with water, partially neutralised to pH 2 with sodium hydroxide, and then extracted with 25 ml of ethyl acetate. The organic phase is dried over magnesium sulphate and then concentrated under reduced pressure. The expected acid is thus obtained as a colourless oil (yield=64%).
$^1$H NMR (250 MHz, DMSO) δ: 8.01 (m, 2H); 7.91 (m, 2H); 3.46 (t, 2H); 2.89 (s, 3H); 2.50 (t, 2H).

In operating analogously to Preparation VIII and Example 1, starting with the acid obtained according to Preparation CCXXIV, the 2 following compounds are obtained:

PREPARATION CCXXV 4,5-dihydro-2-[4-[[methyl[3-[methyl[[2-(trifluoromethyl)phenyl]-sulphonyl]amino]-1-oxopropyl]amino]methyl]phenyl]-1H-imidazole-1-carboxylic acid, 1,1-dimethylethyl ester (White solid; yield=74%).
M.Pt.=50° C.

EXAMPLE 101

N-[[4-(4,5-dihydro-1H-imidazol-2-yl)phenyl]methyl-N-methyl-3-[methyl[[2-(trifluoromethyl)phenyl]sulphonyl]amino]propanamide, trifluoroacetate (White solid, yield=81%).
M.Pt.=56° C.

PREPARATION CCXXVI

N-[(4-cyanophenyl)methyl]-N-methyl-2-[2-[methyl[[2-(trifluoromethyl)phenyl]sulphonyl]amino]ethoxy]acetamide In operating analogously to Preparation VIII, starting with the acid obtained according to Preparation CCV and 4-(methylaminomethyl)benzonitrile, the expected product is obtained as a yellow oil (yield=62%).
$^1$H NMR (250 MHz, DMSO) δ: 8.04 (m, 2H); 7.87 (m, 4H); 7.43 (d, 2H); 4.59 (s, 2H); 4.28 and 4.17 (2s, 2H); 3.67 (m, 2H); 3.46 and 3.40 (2t, 2H); 2.95 and 2.90 (2s, 3H); 2.89 and 2.78 (2s, 3H).

EXAMPLE 102

N-[[4-(1-ethyl-4,5-dihydro-1H-imidazol-2-yl)phenyl]methyl]-N-methyl-2-[2-[methyl[[2-(trifluoromethyl)phenyl]sulphonyl]-amino]ethoxy]acetamide In operating analogously to Preparation II, starting with the compound obtained according to Preparation CCXXVI and N-ethylethylenediamine, the expected product is obtained as a colourless oil (yield=19%).
$^1$H NMR (250 MHz, DMSO) δ: 8.01 (m, 2H); 7.87 (m, 2H); 7.45 (m, 2H); 7.28 (d, 2H); 4.53 (s, 2H); 4.27 and 4.20

(2s, 2H); 3.70 (m, 4H); 3.40 (m, 4H); 3.01 (q, 2H); 2.98 and 2.95 (2s, 3H); 2.93 and 2.79 (2s, 3H); 0.99 (t, 3H).

EXAMPLE 103

N-[[4-[1-(1-methylethyl)-4,5-dihydro-1H-imidazol-2-yl]phenyl]-methyl]-N-methyl-2-[2-[methyl[[2-(trifluoromethyl)phenyl]-sulphonyl]amino]ethoxy]acetamide In operating analogously to Example 102, starting with N-(1-methylethyl)ethylenediamine, the expected product is obtained as an oil (yield=54%).
$^1$H NMR (250 MHz, DMSO) δ: 8.04 (m, 2H); 7.89 (m, 2H); 7.45 (m, 2H); 7.28 (d, 2H); 4.53 (s, 2H); 4.27 and 4.20 (2s, 2H); 3.67 (m, 5H); 3.48 (m, 2H); 3.30 (m, 2H); 2.95 and 2.93 (2s, 3H); 2.88 and 2.80 (2s, 3H); 0.99 (d, 6H).

PREPARATION CCXXVII

N-[(4-cyanophenyl)methyl]-N-methyl-2-[2-[methyl[(4-methoxy-2,6-dimethylphenyl)sulphonyl]amino]ethoxy]acetamide In operating analogously to Preparation CCXXVI, starting with the acid obtained according to Preparation CCIX, the expected product is obtained as a colourless oil (yield=95%).
$^1$H NMR (250 MHz, DMSO) δ: 7.81 (d, 2H); 7.37 (d, 2H); 6.80 (d, 2H); 4.57 (s, 2H); 4.20 and 4.10 (2s, 2H); 3.79 (s, 3H); 3.45 (m, 2H); 3.24 and 3.15 (2t, 2H); 2.85 and 2.76 (2s, 3H); 2.71 and 2.65 (2s, 3H); 2.53 (s, 6H).

PREPARATION CCXXVIII

N-[[4-(aminothioxomethyl)phenyl]methyl]-N-methyl-2-[2-[methyl-[(4-methoxy-2,6-dimethylphenyl)sulphonyl]amino]ethoxy]acetamide A solution of 1.655 g (5 mM) of the compound obtained according to Preparation CCXXVII is prepared in 50 ml of pyridine and 2.09 ml (25 mM) of triethylamine are added. Gaseous hydrogen sulphide is then introduced into this solution and is bubbled in for 10 minutes. The solution which is yellow at the start takes a green colour. The reaction mixture is then agitated for 6 hours at ambient temperature and then diluted with 200 ml of ethyl acetate. The solution obtained is concentrated under reduced pressure. The residue is taken up in 200 ml of toluene and the solution is dried over magnesium sulphate and concentrated under reduced pressure. 1.5 g of the desired product are thus obtained as a yellow paste (yield=84%).
$^1$H NMR (300 MHz, DMSO) δ: 9.82 (m large, 1H); 9.45 (m large, 1H); 7.87 (m, 2H); 7.20 (m, 2H); 6.79 (d, 2H); 4.51 (s, 2H); 4.18 and 4.12 (2s, 2H); 3.78 (s, 3H); 3.56 (m, 2H); 3.24 (m, 2H); 2.82 and 2.76 (2s, 3H); 2.71 and 2.68 (s, 3H); 2.53 (s, 6H).

PREPARATION CCXXIX

N-[[4-[imino(methylthio)methyl]phenyl]methyl]-N-methyl-2-[2-[methyl[(4-methoxy-2,6-dimethylphenyl)sulphonyl]-amino]ethoxy]acetamide 1.5 g (3.04 mM) of the compound obtained according to Preparation CCXXVIII are dissolved in 5 ml of acetone and 3 ml of methyl iodide are added. The mixture is heated under reflux for 1 hour and then concentrated under reduced pressure. The residue is taken up in 50 ml of DCM and the solution is washed with a solution of sodium bicarbonate. The organic phase is dried and then concentrated under reduced pressure. The expected product is thus obtained, and is used without other purification (yield=98%).
$^1$H NMR (300 MHz, DMSO) δ: 10.25 (m, 1H); 7.78 (m, 2H); 7.27 (m, 2H); 6.79 (d, 2H); 4.53 (s, 2H); 4.18 and 4.12 (2s, 2H); 3.79 (s, 3H); 3.54 (m, 2H); 3.24 and 3.18 (2t, 2H); 2.85 and 2.77 (2s, 3H); 2.71 and 2.67 (2s, 3H) 2.58 (s, 6H); 2.40 (s, 3H).

EXAMPLE 104

N-[[4-(1H-2,4-triazol-5-yl)phenyl]methyl]-N-methyl-2-[2-[methyl-[(4-methoxy-2,6-dimethylphenyl)sulphonyl]amino]ethoxy]acetamide A solution of 1.5 g (2.96 mM) of the compound obtained according to preparation CCXXIX is prepared in 16.5 ml of ethanol, and 324 mg (5.4 mM) of formylhydrazine, 279 mg (2.63 mM) of triethylamine and 35 μl of sulphuric acid then are added. The reaction mixture is heated under reflux for 2 hours and then concentrated under reduced pressure. The residue is taken up in solution in DCM, washed twice with water, dried over magnesium sulphate and concentrated under reduced pressure. The residue is purified first of all on a silica column in eluting with the aid of a mixture of toluene/isopropanol (9/1; v/v), and then secondly by reverse phase chromatography on RP18 grafted silica, in eluting with a mixture of acetonitrile/water (4/6; v/v). The pure product is obtained by lyophilisation of the pure fractions. 340 mg of the desired product are thus obtained as a green flaky solid (yield=23%).
M.Pt.=60° C.

PREPARATION CCXXX

N-methyl-2,4-dinitrobenzenesulphonamide

In operating analogously to Preparation V, starting with 2,4-dinitrobenzenesulphonyl chloride, the expected product is obtained as a yellow solid
(yield=76%).
M.Pt.=155° C.

PREPARATION CCXXXI

4-[[(2,4-dinitrophenyl)sulphonyl]methylamino]-2-butenoic acid, 1,1-dimethylethyl ester In operating analogously to Preparation VI, starting with the compound obtained according to Preparation CCXXX and the t-butyl ester of 4-bromo-2-butenoic acid, the expected product is obtained as a yellow solid (yield=82%).
$^1$H NMR (300 MHz, CDCl$_3$) δ: 8.50 (dd, 1H); 8.48 (m, 1H); 8.25 (d, 1H); 6.69 (dt, 1H); 5.92 (dt, 1H); 4.04 (dd, 2H); 2.93 (s, 3H); 1.48 (s, 9H),

PREPARATION CCXXXII

4-[[(2,4-dinitrophenyl)sulphonyl]methylamino]-2-butenoic acid

In operating analogously to Preparation LXXVIII, starting with the ester obtained according to Preparation CCXXXI, the expected product is obtained as a pale yellow solid (yield=99%).
M.Pt.=174° C.

PREPARATION CCXXXIII

2-[4-[[[(2E)-4-[[(2,4-dinitrophenyl)sulphonyl]methylamino]-1-oxo-2-butenyl]methylamino]methyl]phenyl]-4,5-dihydro-1H-imidazole-1-carboxylic acid, 1,1-dimethylethyl ester In operating analogously to Preparation VIII, starting with the acid obtained according to Preparation CCXXXII and the amine obtained according to Preparation IV, the expected product is obtained as a yellow solid (yield=88%).

M.Pt.=78° C.

PREPARATION CCXXXIV 4,5-dihydro-2-[4-[[methyl[(2E)-4-(methylamino)-1-oxo-2-butenyl]-amino]methyl]phenyl]-1H-imidazole-1-carboxylic acid, 1,1-dimethylethyl ester 1 g (1.62 mM) of the compound obtained according to Preparation CCXXXIII are dissolved in 18 ml of DCM and 672 mg (4.9 mM) of potassium carbonate and 167 μl (1.62 mM) of thiophenol are added. The mixture is agitated for 1.5 hours at ambient temperature, and diluted with 25 ml of DCM. This organic phase is washed 3 times with water, dried over magnesium sulphate and concentrated under reduced pressure. The residue is purified by chromatography on silica gel in eluting with the aid of a mixture of DCM/methanol (9/1; v/v). 560 mg of the desired product are thus obtained as a yellow oil (yield=89%).

$^1$H NMR (250 MHz, CDCl$_3$) δ: 7.49 (dd, 2H); 7.22 (dd, 2H); 6.96 (m, 1H); 6.47 (dd, 1H); 4.65 (d, 2H); 3.97 (m, 4H); 3.40 (m, 2H); 2.98 and 2.96 (2s, 3H); 2.49 and 2.42 (2s, 3H); 1.29 and 1.25 (2s, 9H).

In operating analogously to Preparation V, starting with the amine obtained according to Preparation CCXCCIV and various benzenesulphonyl chlorides, the following compounds are obtained:

PREPARATION CCXXXV

2-[4-[[[(2E)-4-[[(2-chloro-4-fluorophenyl)sulphonyl]methylamino]-1-oxo-2-butenyl]methylamino]methyl]phenyl]-4,5-dihydro-1H-imidazole-1-carboxylic acid, 1,1-dimethylethyl ester (Colourless oil, yield=59%)

$^1$H NMR (250 MHz, CDCl$_3$) δ: 8.13 (m, 1H); 7.50 (m, 2H); 7.25 (m, 4H); 6.79 (m, 1H); 6.51 (dd, 1H); 4.66 and 4.59 (2s, 2H); 4.10 and 4.01 (2d, 2H); 4.00 (m, 4H); 2.99 and 2.95 (2s, 3H); 2.86 and 2.75 (2s, 3H); 1.30 (d, 9H).

PREPARATION CCXXXVI

2-[4-[[[(2E)-4-[[[2,6-dichloro-4-(trifluoromethyl)phenyl]sulphonyl]-methylamino]-1-oxo-2-butenyl]methylamino]methyl]phenyl]-4,5-dihydro-1H-imidazole-1-carboxylic acid, 1,1-dimethylethyl ester (Colourless oil; yield=73%).

$^1$H NMR (250 MHz, CDCl$_3$) δ: 7.70 (d, 2H); 7.50 (m, 2H); 7.24 (m, 2H); 6.84 (m, 1H); 6.55 (dd, 1H); 4.66 and 4.59 (2s, 2H); 4.18 and 4.07 (2d, 2H); 4.00 (m, 4H); 3.00 and 2.96 (2s, 3H); 2.97 and 2.84 (2s, 3H); 1.27 (d, 9H).

PREPARATION CCXXXVII

2-[4-[[[(2E)-4-[[(2,6-difluorophenyl)sulphonyl]methylamino]-1-oxo-2-butenyl]methylamino]methyl]phenyl]-4,5-dihydro-1H-imidazole-1-carboxylic acid, 1,1-dimethylethyl ester (Colourless oil; yield=61%).

$^1$H NMR (250 MHz, CDCl$_3$) δ: 7.52 (m, 3H); 7.27 (m, 2H); 7.02 (m, 2H); 6.85 (m, 1H); 6.53 (dd, 1H); 4.66 and 4.59 (2s, 2H); 4.09 and 4.01 (2d, 2H); 3.98 (m, 4H); 2.99 and 2.94 (2s, 3H); 2.95 and 2.82 (2s, 3H); 1.27 (d, 9H).

PREPARATION CCXXXVIII

2-[4-[[[(2E)-4-[[(2-nitrophenyl)sulphonyl]methylamino]-1-oxo-2-butenyl]methylamino]methyl]phenyl]-4,5-dihydro-1H-imidazole-1-carboxylic acid, 1,1-dimethylethyl ester

PREPARATION CCXXXIX

2-[4-[[[(2E)-4-[[(2,4,6-trimethylphenyl)sulphonyl]methylamino]-1-oxo-2-butenyl]methylamino]methyl]phenyl]-4,5-dihydro-1H-imidazole-1-carboxylic acid, 1,1-dimethylethyl ester (White paste; yield=69%).

$^1$H NMR (300 MHz, CDCl$_3$) δ: 7.49 (dd, 2H); 7.25 (dd, 2H); 6.93 (d, 2H); 6.77 (m, 1H); 6.53 (dd, 1H); 4.65 and 4.57 (2s, 2H); 4.06 and 3.85 (2d, 2H); 3.94 (m, 4H); 2.98 and 2.94 (2s, 3H); 2.71 and 2.57 (2s, 3H); 2.61 (s, 6H) 2.29 and 2.28 (2s, 3H); 1.25 (d, 9H).

PREPARATION CCXL

2-[4-[[[(2E)-4-[[(2,5-dichlorophenyl)sulphonyl]methylamino]-1-oxo-2-butenyl]methylamino]methyl]phenyl]-4,5-dihydro-1H-imidazole-1-carboxylic acid, 1,1-dimethylethyl ester (Colourless oil; yield=63%).

$^1$H NMR (300 MHz, CDCl$_3$) δ: 8.05 (m, 1H); 7.46 (m, 4H); 7.27 (d, 1H); 7.17 (d, 1H); 6.81 (m, 1H); 6.50 (dd, 1H); 4.66 and 4.59 (2s, 2H); 4.12 and 4.04 (2d, 2H); 4.01 (m, 4H); 2.99 and 2.95 (2s, 3H); 2.89 and 2.78 (2s, 3H); 1.27 (d, 9H).

PREPARATION CCXLI

2-[4-[[[(2E)-4-[[(2,4-dichlorophenyl)sulphonyl]methylamino]-1-oxo-2-butenyl]methylamino]methyl]phenyl]-4,5-dihydro-1H-imidazole-1-carboxylic acid, 1,1-dimethylethyl ester (Colourless oil; yield=48%).

$^1$H NMR (250 MHz, CDCl$_3$) δ: 8.05 (t, 1H); 7.54 (m, 3H); 7.37 (m, 1H); 7.27 (d, 1H); 7.20 (d, 1H); 6.83 (m, 1H); 6.50 (dd, 1H); 4.66 and 4.56 (2s, 2H); 4.10 and 3.99 (2d, 2H); 3.96 (m, 4H); 2.99 and 2.95 (2s, 3H); 2.86 and 2.75 (2s, 3H); 1.27 (d, 9H).

PREPARATION CCXLII

2-[4-[[[(2E)-4-[[(3-chloro-2-methylphenyl)sulphonyl]methylamino]-1-oxo-2-butenyl]methylamino]methyl]phenyl]-4,5-dihydro-1H-imidazole-1-carboxylic acid, 1,1-dimethylethyl ester (Colourless oil; yield=69%).
$^1$H NMR (250 MHz, CDCl$_3$) δ: 7.84 (t, 1H); 7.50 (m, 3H); 7.26 (m, 3H); 6.82 (m, 1H); 6.54 (dd, 1H); 4.66 and 4.58 (2s, 2H); 3.97 (m, 6H); 3.01 and 2.94 (2s, 3H); 2.82 and 2.70 (2s, 3H); 2.67 and 2.63 (2s, 3H); 1.27 (d, 9H).

PREPARATION CCXLIII

2-[4-[[[(2E)-4-[[(2-cyanophenyl)sulphonyl]methylamino]-1-oxo-2-butenyl]methylamino]methyl]phenyl]-4,5-dihydro-1H-imidazole-1-carboxylic acid, 1,1-dimethylethyl ester (Yellow solid; yield=67%).
M.Pt.=64° C.

PREPARATION CCXLIV

2-[4-[[[(2E)-4-[[(2-chloro-4-methoxyphenyl)sulphonyl]methylamino]-1-oxo-2-butenyl]methylamino]methyl]phenyl]-4,5-dihydro-1H-imidazole-1-carboxylic acid, 1,1-dimethylethyl ester (Yellow solid; yield=78%).
M.Pt.=58° C.

PREPARATION CCXLV

2-[4-[[[(2E)-4-[[(2,4-dichloro-5-methylphenyl)sulphonyl]methylamino]-1-oxo-2-butenyl]methylamino]methyl]phenyl]-4,5-dihydro-1H-imidazole-1-carboxylic acid, 1,1-dimethylethyl ester (White ecru solid; yield=75%).
M.Pt.=70° C.

PREPARATION CCXLVI

2-[4-[[[(2E)-4-[[(2,3,4-trichlorophenyl)sulphonyl]methylamino]-1-oxo-2-butenyl]methylamino]methyl]phenyl]-4,5-dihydro-1H-imidazole-1-carboxylic acid, 1,1-dimethylethyl ester (White ecru solid; yield=78%).
M.Pt.=66° C.

PREPARATION CCXLVII

2-[4-[[[(2E)-4-[[(2-chloro-4-(trifluoromethoxy)phenyl]sulphonyl]-methylamino]-1-oxo-2-butenyl]methylamino]methyl]phenyl]-4,5-dihydro-1H-imidazole-1-carboxylic acid, 1,1-dimethylethyl ester (White solid; yield=81%).
M.Pt.=50° C.

PREPARATION CCXLVIII

2-[4-[[[(2E)-4-[[[4-methoxy-2-(trifluoromethyl)phenyl]sulphonyl]-methylamino]-1-oxo-2-butenyl]methylamino]methyl]phenyl]-4,5-dihydro-1H-imidazole-1-carboxylic, 1,1-dimethylethyl ester (White solid; yield=62%).
M.Pt.=50° C.

PREPARATION CCIL

2-[4-[[[(2E)-4-[[(2,6-dimethyl-4-methoxyphenyl)sulphonyl]methylamino]-1-oxo-2-butenyl]methylamino]methyl]phenyl]-4,5-dihydro-1H-imidazole-1-carboxylic acid, 1,1-dimethylethyl ester (White solid; yield=75%).
M.Pt.=50° C.

In operating analogously to Example 1, starting with the compounds obtained according to Preparations CCXXXV to CCIL, the following products are obtained:

EXAMPLE 105

(2E)-4-[[(2-chloro-4-fluorophenyl)sulphonyl]methylamino]-N-[[4-(4,5-dihydro-1H-imidazol-2-yl)phenyl]methyl]-N-methyl-2-butenamide, trifluoroacetate (Pink paste; yield=99%)
$^1$H NMR (250 MHz, DMSO) δ: 10.48 (s, 2H); 8.09 (m, 1H); 7.91 (m, 2H); 7.78 (m, 1H); 7.49 (m, 3H); 6.61 (m, 2H); 4.76 and 4.66 (2s, 2H); 4.05 (m, 2H); 4.01 (s, 4H); 3.09 and 3.03 (2s, 3H); 2.96 and 2.90 (2s, 3H).

EXAMPLE 106

(2E)-4-[[[2,6-dichloro-4-(trifluoromethyl)phenyl]sulphonyl]methylamino]-N-[[4-(4,5-dihydro-1H-imidazol-2-yl)phenyl]methyl]-N-methyl-2-butenamide, trifluoroacetate (white solid; yield=99%)
M.Pt.=62° C.

EXAMPLE 107

(2E)-4-[[(2,6-difluorophenyl)sulphonyl]methylamino]-N-[[4-(4,5-dihydro-1H-imidazol-2-yl)phenyl]methyl]-N-methyl-2-butenamide, trifluoroacetate (Pink paste; yield=99%)
$^1$H NMR (250 MHz, DMSO) δ: 10.49 (s, 2H); 7.90 (m, 2H); 7.80 (m, 1H); 7.47 (d, 2H); 7.32 (m, 2H); 6.60 (m, 2H); 4.76 and 4.66 (2s, 2H); 4.04 and 3.94 (2d, 2H); 4.01 (s, 4H); 3.03 and 2.90 (2s, 3H); 2.86 and 2.71 (2s, 3H).

EXAMPLE 108

(2E)-4-[[(2-nitrophenyl)sulphonyl]methylamino]-N-[[4-(4,5-dihydro-1H-imidazol-2-yl)phenyl]methyl]-N-methyl-2-butenamide, trifluoroacetate (Pink paste; yield=94%)
$^1$H NMR (250 MHz, DMSO) δ: 10.54 (s, 2H); 7.94 (m, 6H); 7.48 (m, 2H); 6.60 (m, 2H); 4.74 and 4.65 (2s, 2H); 4.08 and 3.99 (2d, 2H); 4.01 (s, 4H) 3.01 and 2.89 (2s, 3H); 2.87 and 2.72 (2s, 3H).

EXAMPLE 109

(2E)-4-[[(2,4,6-trimethylphenyl)sulphonyl]methylamino]-N-[[4-(4,5-dihydro-1H-imidazol-2-yl)phenyl]methyl]-N-methyl-2-butenamide, trifluoroacetate (White solid; yield=78%)
M.Pt.=64° C.

EXAMPLE 110

(2E)-4-[[(2,5-dichlorophenyl)sulphonyl]methylamino]-N-[[4-(4,5-dihydro-1H-imidazol-2-yl)phenyl]methyl]-N-methyl-2-butenamide, trifluoroacetate (White solid; yield=99%)
M.Pt.=65° C.

EXAMPLE 111

(2E)-4-[[(2,4-dichlorophenyl)sulphonyl]methylamino]-N-[[4-(4,5-dihydro-1H-imidazol-2-yl)phenyl]methyl]-N-methyl-2-butenamide, trifluoroacetate (White solid; yield=99%)
M.Pt.=65° C.

EXAMPLE 112

(2E)-4-[[(3-chloro-2-methylphenyl)sulphonyl]methylamino]-N-[[4-(4,5-dihydro-1H-imidazol-2-yl)phenyl]methyl]-N-methyl-2-butenamide, trifluoroacetate (White solid; yield=99%)
M.Pt.=64° C.

EXAMPLE 113

(2E)-4-[[(2-cyanophenyl)sulphonyl]methylamino]-N-[[4-(4,5-dihydro-1H-imidazol-2-yl)phenyl]methyl]-N-methyl-2-butenamide, trifluoroacetate (White solid; yield=99%)
M.Pt.=60° C.

EXAMPLE 114

(2E)-4-[[(2-chloro-4-methoxyphenyl)sulphonyl]methylamino]-N-[[4-(4,5-dihydro-1H-imidazol-2-yl)phenyl]methyl]-N-methyl-2-butenamide, trifluoroacetate (White solid; yield=90%)
M.Pt.=68° C.

EXAMPLE 115

(2E)-4-[[(2,4-dichloro-5-methylphenyl)sulphonyl]methylamino]-N-[[4-(4,5-dihydro-1H-imidazol-2-yl)phenyl]methyl]-N-methyl-2-butenamide, trifluoroacetate (White solid; yield=99%)
M.Pt.=79° C.

EXAMPLE 116

(2E)-4-[[(2,3,4-trichlorophenyl)sulphonyl]methylamino]-N-[[4-(4,5-dihydro-1H-imidazol-2-yl)phenyl]methyl]-N-methyl-2-butenamide, trifluoroacetate (White solid; yield=90%)
M.Pt.=87° C.

EXAMPLE 117

(2E)-4-[[[2-chloro-4-(trifluoromethoxy)phenyl]sulphonyl]-methylamino]-N-[[4-(4,5-dihydro-1H-imidazol-2-yl)phenyl]methyl]-N-methyl-2-butenamide, trifluoroacetate (White solid; yield=99%)
M.Pt.=68° C.

EXAMPLE 118

(2E)-4-[[[4-methoxy-2-(trifluoromethyl)phenyl]sulphonyl]methylamino]-N-[[4-(4,5-dihydro-1H-imidazol-2-yl)phenyl]methyl]-N-methyl-2-butenamide, trifluoroacetate (White solid; yield=99%)
M.Pt.=50° C.

EXAMPLE 119

(2E)-4-[[(4-methoxy-2,6-dimethylphenyl)sulphonyl]methylamino]-N-[[4-(4,5-dihydro-1H-imidazol-2-yl)phenyl]methyl]-N-methyl-2-butenamide, trifluoroacetate (White solid; yield=99%)
M.Pt.=50° C.

In operating analogously to Preparation V, starting with the amine obtained according to Preparation CL)(XIX and various benzenesulphonyl chlorides, the following compounds are obtained:

PREPARATION CCL

2-[4-[[[5-[[(2-chloro-4-methoxyphenyl)sulphonyl]methylamino]-1-oxopentyl]methylamino]methyl]phenyl]-4,5-dihydro-1H-imidazole-1-carboxylic acid, 1,1-dimethylethyl ester (White solid; yield=32%)
M.Pt.=60° C.

PREPARATION CCLI

2-[4-[[[5-[[(4-methoxy-2-methylphenyl)sulphonyl]methylamino]-1-oxopentyl]methylamino]methyl]phenyl]-4,5-dihydro-1H-imidazole-1-carboxylic acid, 1,1-dimethylethyl ester (Colourless oil; yield=24%)
$^1$H NMR (250 MHz, DMSO) δ: 7.73 (t, 1H); 7.42 (m, 2H); 7.20 (m, 2H); 6.93 (m, 2H); 4.56 (d, 2H); 3.86 (s, 4H); 3.81 (s, 3H); 3.04 (m, 2H); 2.88 and 2.80 (2s, 3H); 2.68 and 2.65 (2s, 3H); 2.48 (m, 2H); 1.50 (m, 4H); 1.17 (s, 9H).

PREPARATION CCLII

2-[4-[[[5-[[[2-methyl-4-(trifluoromethoxy)phenyl] sulphonyl]methylamino]-1-oxopentyl]methylamino] methyl]phenyl]-4,5-dihydro-1H-imidazole-1-carboxylic acid, 1,1-dimethylethyl ester (Colourless oil; yield=30%)
$^1$H NMR (300 MHz, DMSO) δ: 7.88 (t, 1H); 7.44 (m, 4H); 7.20 (m, 2H); 4.59 and 4.52 (2s, 2H); 3.83 (m, 4H); 3.14 (m, 2H); 2.89 and 2.81 (2s, 3H); 2.76 and 2.74 (2s, 3H); 2.55 and 2.51 (2s, 3H); 2.50 (m, 2H); 1.52 (m, 4H); 1.17 (s, 9H).

PREPARATION CCLIII

2-[4-[[[5-[[[4-methoxy-2-(trifluoromethyl)phenyl] sulphonyl]methylamino]-1-oxopentyl]methylamino] methyl]phenyl]-4,5-dihydro-1H-imidazole-1-carboxylic acid, 1,1-dimethylethyl ester (Colourless oil; yield=35%)
$^1$H NMR (300 MHz, DMSO) δ: 7.95 (t, 1H); 7.41 (m, 4H); 7.22 (m, 2H); 4.59 and 4.52 (2s, 2H); 3.91 (s, 3H); 3.83 (m, 4H); 3.16 (m, 2H); 2.89 and 2.81 (2s, 3H); 2.78 and 2.76 (2s, 3H); 2.36 (m, 2H); 1.48 (m, 4H); 1.17 (s, 9H).

In operating analogously to Example 1, starting with the compounds obtained according to Preparations CCL to CCLIII, the following products are obtained:

EXAMPLE 120

5-[[(2-chloro-4-methoxyphenyl)sulphonyl]methylamino]-N-[[4-(4,5-dihydro-1H-imidazol-2-yl)phenyl]methyl]-N-methyl-pentanamide, trifluoroacetate (Yellow oil; yield=97%)
$^1$H NMR (300 MHz, DMSO) δ: 10.50 (d, 2H); 7.90 (m, 3H); 7.45 (d, 2H); 7.26 (s, 1H); 7.11 (m, 1H); 4.69 and 4.60 (2s, 2H); 4.00 (s, 4H); 3.86 (s, 3H); 3.14 (m, 2H); 2.95 and 2.82 (2s, 3H); 2.75 and 2.72 (2s, 3H); 2.49 and 2.30 (2m, 2H); 1.52 (m, 4H).

EXAMPLE 121

5-[[(4-methoxy-2-methylphenyl)sulphonyl]methylamino]-N-[[4-(4,5-dihydro-1H-imidazol-2-yl)phenyl]methyl]-N-methyl-pentanamide, trifluoroacetate (Colourless oil; yield=94%)
$^1$H NMR (300 MHz, DMSO) δ: 10.52 (d, 2H); 7.90 (m, 2H); 7.70 (m, 1H); 7.47 (m, 2H); 6.90 (m, 2H); 4.68 and 4.60 (2s, 2H); 4.01 (s, 4H); 3.81 (s, 3H); 3.07 (m, 2H); 2.94 and 2.82 (2s, 3H); 2.68 and 2.64 (2s, 3H); 2.50 (s, 3H); 2.49 and 2.39 (2t, 2H); 1.52 (m, 4H).

EXAMPLE 122

5-[[[2-methyl-4-(trifluoromethoxy)phenyl]sulphonyl]methylamino]-N-[[4-(4,5-dihydro-1H-imidazol-2-yl)phenyl]methyl]-N-methylpentanamide, trifluoroacetate (Red paste; yield=99%)
$^1$H NMR (250 MHz, DMSO) δ: 10.49 (d, 2H); 7.89 (m, 3H); 7.44 (m, 4H); 4.69 and 4.60 (2s, 2H); 4.00 (s, 4H); 3.14 (m, 2H); 2.95 and 2.82 (2s, 3H); 2.76 and 2.73 (2s, 3H); 2.57 and 2.55 (2s, 3H); 2.44 and 2.38 (2m, 2H); 1.50 (m, 4H).

EXAMPLE 123

5-[[[4-methoxy-2-(trifluoromethyl)phenyl]sulphonyl]methylamino]-N-[[4-(4,5-dihydro-1H-imidazol-2-yl)phenyl]methyl]-N-methylpentanamide, trifluoroacetate (Pink paste; yield=99%)
$^1$H NMR (250 MHz, DMSO) δ: 10.50 (d, 2H); 7.90 (m, 3H); 7.40 (m, 4H); 4.69 and 4.60 (2s, 2H); 4.00 (s, 4H); 3.92 (s, 3H); 3.19 (m, 2H); 2.96 and 2.83 (2s, 3H); 2.78 and 2.75 (2s, 3H); 2.49 and 2.45 (2m, 2H); 1.53 (m, 4H).

In operating analogously to Preparation V, starting with the amine obtained according to Preparation CLII and various benzenesulphonyl chlorides, the following compounds are obtained:

PREPARATION CCLIV

2-[4-[[[[2-[[(2-chloro-4-methoxyphenyl)sulphonyl] methylamino]-ethoxy]acetyl]methylamino]methyl] phenyl]-4,5-dihydro-1H-imidazole-1-carboxylic acid, 1,1-dimethylethyl ester (Colourless oil; yield=64%)
$^1$H NMR (300 MHz, DMSO) δ: 7.89 (m, 1H); 7.42 (m, 2H); 7.22 (m, 3H); 7.05 (dd, 1H); 4.52 (s, 2H); 4.22 and 4.18 (2s, 2H); 3.82 (m, 4H); 3.79 (s, 3H); 3.60 (m, 2H); 3.39 (m, 2H); 2.85 and 2.76 (2s, 3H); 2.84 and 2.82 (2s, 3H); 1.18 (s, 9H).

PREPARATION CCLV

2-[4-[[[[2-[[(4-methoxy-2-methylphenyl)sulphonyl] methylamino]-ethoxy]acetyl]methylamino]methyl] phenyl]-4,5-dihydro-1H-imidazole-1-carboxylic acid, 1,1-dimethylethyl ester (Colourless oil; yield=53%)
$^1$H NMR (300 MHz, DMSO) δ: 7.74 (m, 1H); 7.44 (m, 2H); 7.23 (d, 2H); 6.92 (m, 2H); 4.51 (s, 2H); 4.20 and 4.17 (2s, 2H); 3.84 (m, 4H); 3.81 (s, 3H); 3.59 (m, 2H); 3.26 (m, 2H); 2.83 and 2.77 (2s, 3H); 2.78 and 2.75 (2s, 3H) 2.50 (s, 3H); 1.17 (s, 9H).

In operating analogously to Example 1, starting with the preceding compounds, the following compounds are obtained:

EXAMPLE 124

2-[2-[[(2-chloro-4-methoxyphenyl)sulphonyl]methylamino]ethoxy]-N-[[4-(4,5-dihydro-1H-imidazol-2-yl)phenyl]methyl]-N-methylacetamide, trifluoroacetate (White solid, yield=96%).
M.Pt.=60° C.

EXAMPLE 125

2-[2-[[(4-methoxy-2-methylphenyl)sulphonyl]methylamino]ethoxy]-N-[[4-(4,5-dihydro-1H-imidazol-2-yl)phenyl]methyl]-N-methylacetamide, trifluoroacetate (White paste; yield=94%).
$^1$H NMR (300 MHz, DMSO) δ: 10.50 (d, 2H); 7.90 (m, 2H); 7.73 (m, 1H); 7.49 (d, 2H); 6.97 (m, 1H); 6.90 (m, 1H); 4.60 (s, 2H); 4.25 and 4.16 (2s, 2H); 4.00 (s, 4H); 3.81 (s, 3H); 3.56 (m, 2H); 3.30 and 3.20 (2t, 2H); 2.89 and 2.72 (2s, 3H); 2.78 (s, 3H); 2.50 (s, 3H).

TABLE I

| Ex.* | R₁ | R₂ | Y | R₃ R₄ | R₅ | R₆ |
|---|---|---|---|---|---|---|
| 1 | 2,6-dichloro-3-methylphenyl | CH₃ | —(CH₂)₄— | —(CH₂)₂— | H | H |
| 2 | 2,6-dichloro-3-methylphenyl | CH₃ | —(CH₂)₃— | —(CH₂)₂— | H | H |
| 3 | 2,6-dichloro-3-methylphenyl | CH₃ | —(CH₂)₂— | —(CH₂)₂— | H | H |
| 4 | 2,6-dichloro-3-methylphenyl | CH₃ | —CH₂—CH=CH— | —(CH₂)₂— | H | H |
| 5 | 2-chlorophenyl | CH₃ | —(CH₂)₄— | —(CH₂)₂— | H | H |
| 6 | 2-chlorophenyl | CH₃ | —CH₂—CH=CH— | —(CH₂)₂— | H | H |
| 7 | 2,3-dichlorophenyl | CH₃ | —(CH₂)₂— | —(CH₂)₂— | H | H |
| 8 | 2,3-dichlorophenyl | CH₃ | —(CH₂)₃— | —(CH₂)₂— | H | H |
| 9 | 2,3-dichlorophenyl | CH₃ | —(CH₂)₄— | —(CH₂)₂— | H | H |

TABLE I-continued
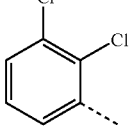
| Ex.* | R₁ | R₂ | Y | R₃ R₄ | R₅ | R₆ |
|---|---|---|---|---|---|---|
| 10 | 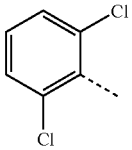 2,3-diCl-phenyl | CH₃ | —CH₂—CH=CH— | —(CH₂)₂— | H | H |
| 11 | 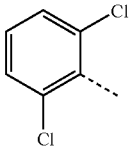 2,6-diCl-phenyl | CH₃ | —(CH₂)₄— | —(CH₂)₂— | H | H |
| 12 | 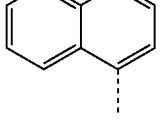 2,6-diCl-phenyl | CH₃ | —CH₂—CH=CH— | —(CH₂)₂— | H | H |
| 13 | naphthyl | CH₃ | —(CH₂)₄— | —(CH₂)₂— | H | H |
| 14 | naphthyl | CH₃ | —CH₂—CH=CH— | —(CH₂)₂— | H | H |
| 15 | 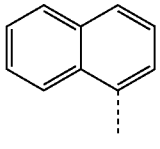 2-Cl-phenyl | cPr | —(CH₂)₄— | —(CH₂)₂— | H | H |
| 16 | 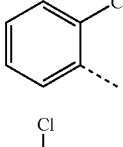 2,3-diCl-phenyl | cPr | —(CH₂)₄— | —(CH₂)₂— | H | H |
| 17 | 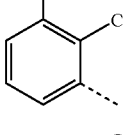 2,6-diCl-phenyl | cPr | —(CH₂)₄— | —(CH₂)₂— | H | H |
| 18 | 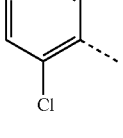 2,6-diCl-phenyl | CH(CH₃)₂ | —(CH₂)₄— | —(CH₂)₂— | H | H |

TABLE I-continued
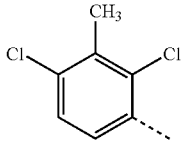
| Ex.* | R₁ | R₂ | Y | R₃ R₄ | R₅ | R₆ |
|---|---|---|---|---|---|---|
| 19 | 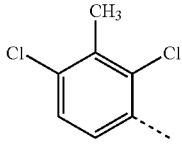 | CH₂CONH₂ | —(CH₂)₄— | —(CH₂)₂— | H | H |
| 20 | 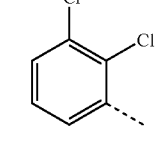 | (CH₂)₂CONH₂ | —(CH₂)₄— | —(CH₂)₂— | H | H |
| 21 | 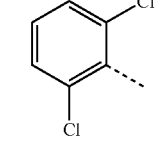 | CH(CH₃)₂ | —(CH₂)₂— | —(CH₂)₂— | H | H |
| 22 | 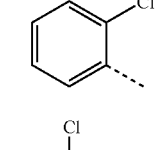 | CH(CH₃)₂ | —(CH₂)₂— | —(CH₂)₂— | H | H |
| 23 | 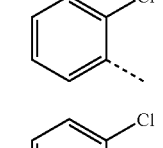 | cPr | —(CH₂)₂—O—CH₂— | —(CH₂)₂— | H | H |
| 24 | 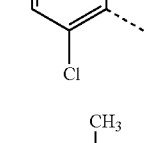 | cPr | —(CH₂)₂—O—CH₂— | —(CH₂)₂— | H | H |
| 25 | 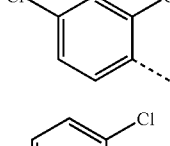 | cPr | —(CH₂)₂—O—CH₂— | —(CH₂)₂— | H | H |
| 26 | 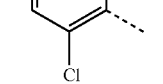 | (CH₂)₂—Ph | —(CH₂)₂—O—CH₂— | —(CH₂)₂— | H | H |
| 27 |  | CH₃ | —(CH₂)₂— | —(CH₂)₂— | H | H |

TABLE I-continued
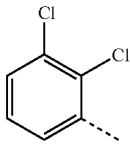
| Ex.* | R₁ | R₂ | Y | R₃ | R₄ | R₅ | R₆ |
|---|---|---|---|---|---|---|---|
| 28 | 2,3-diClPh | cPr | —(CH₂)₂— | —(CH₂)₂— | | H | H |
| 29 | 2,6-diClPh | cPr | —(CH₂)₂— | —(CH₂)₂— | | H | H |
| 30 | 2,3-diClPh | CH₂—CF₃ | —(CH₂)₂— | —(CH₂)₂— | | H | H |
| 31 | 2,6-diClPh | CH₂—CF₃ | —(CH₂)₂— | —(CH₂)₂— | | H | H |
| 32 | 2-CF₃Ph | CH₃ | —CH₂—CH=CH— | —(CH₂)₂— | | H | H |
| 33 | 2,6-diCl-3-MePh | H | —CH₂—CH=CH— | —(CH₂)₂— | | H | H |
| 34 bas | 2,6-diCl-3-MePh | CH₃ | —(CH₂)₄— | —CH₂—C(CH₃)₂— | | H | H |
| 35 | 2,6-diCl-3-MePh | CH₃ | —(CH₂)₄— | —CH₂—C(CH₃)₂— | | H | H |

TABLE I-continued

[Structure: R₁—SO₂—N(R₂)—Y—C(=O)—N(CH₃)—CH₂—(phenyl with R₆)—C(=N—R₃)(N(R₄)(R₅))]

| Ex.* | R₁ | R₂ | Y | R₃ R₄ | R₅ | R₆ |
|---|---|---|---|---|---|---|
| 36 bas | 2,3-dichlorophenyl | CH₃ | —(CH₂)₂—O—CH₂— | —(CH₂)₃— | H | H |
| 37 bas | 2,6-dichloro-3-methylphenyl (CH₃ with 2 Cl) | CH₃ | —(CH₂)₂—O—CH₂— | —(CH₂)₂— | CH₃ | H |
| 38 bas | 2,3-dichlorophenyl | CH₃ | —(CH₂)₂—O—CH₂— | —(CH₂)₂— | CH₃ | H |
| 39 | 2,6-dichloro-3-methylphenyl | CH₃ | —(CH₂)₂—O—CH₂— | —(CH₂)₂— | H | H |
| 40 | 2,3-dichlorophenyl | CH₃ | —(CH₂)₂—O—CH₂— | —(CH₂)₂— | H | H |
| 41 | 2,6-dichlorophenyl | CH₃ | —(CH₂)₂—O—CH₂— | —(CH₂)₂— | H | H |
| 42 | 2-chlorophenyl | CH₃ | —(CH₂)₂—O—CH₂— | —(CH₂)₂— | H | H |
| 43 | 2,3-dichlorophenyl | CH₃ | —(CH₂)₂—O—CH₂— | —(CH₂)₂— | H | 2-F |
| 44 chl | 2,3-dichlorophenyl | CH₃ | —CH(CH₃)—CH₂—O—CH₂— | —(CH₂)₂— | H | H |

TABLE I-continued

[Structure: R₁—SO₂—N(R₂)—Y—C(=O)—N(CH₃)—CH₂—[phenyl with R₆]—C(=N—R₃)—N(R₄)(R₅)]

| Ex.* | R₁ | R₂ | Y | R₃ R₄ | R₅ | R₆ |
|---|---|---|---|---|---|---|
| 45 | 2,3-dichlorophenyl | CH₃ | —(CH₂)₂—O—CH₂— | —(CH₂)₃— | H | H |
| 46 chl | 2,6-dichloro-3-methylphenyl | CH₃ | —(CH₂)₂—O—CH₂— | —(CH₂)₂— | CH₃ | H |
| 47 chl | 2,3-dichlorophenyl | CH₃ | —(CH₂)₂—O—CH₂— | —(CH₂)₂— | CH₃ | H |
| 48 | 2-(CF₃)phenyl | CH₃ | —(CH₂)₂—O—CH₂— | —(CH₂)₂— | H | H |
| 49 | 4-methoxy-3,5-dimethylphenyl | CH₃ | —(CH₂)₂—O—CH₂— | —(CH₂)₂— | H | H |
| 50 | 2,4-dichlorophenyl | CH₃ | —(CH₂)₂—O—CH₂— | —(CH₂)₂— | H | H |
| 51 | 2,5-dichloro-4-methylphenyl | CH₃ | —(CH₂)₂—O—CH₂— | —(CH₂)₂— | H | H |
| 52 | 2-nitrophenyl | CH₃ | —(CH₂)₂—O—CH₂— | —(CH₂)₂— | H | H |
| 53 | 3,5-dichloro-4-(CF₃)phenyl | CH₃ | —(CH₂)₂—O—CH₂— | —(CH₂)₂— | H | H |

TABLE I-continued

| Ex.* | R₁ | R₂ | Y | R₃ R₄ | R₅ | R₆ |
|---|---|---|---|---|---|---|
| 54 | 3-chloro-2-methylphenyl | CH₃ | —(CH₂)₂—O—CH₂— | —(CH₂)₂— | H | H |
| 55 | 2-cyanophenyl | CH₃ | —(CH₂)₂—O—CH₂— | —(CH₂)₂— | H | H |
| 56 | 2,3-dichlorophenyl | CH₃ | —(CH₂)₂—O—CH₂— | —(CH₂)₂— | H | H |
| 57 | 3-chloro-2-methylphenyl | CH₃ | —(CH₂)₂—O—CH₂— | —(CH₂)₂— | H | H |
| 58 | 4-cyano-2-chlorophenyl | CH₃ | —(CH₂)₂—O—CH₂— | —(CH₂)₂— | H | H |
| 59 | 4-trifluoromethyl-2-nitrophenyl | CH₃ | —(CH₂)₂—O—CH₂— | —(CH₂)₂— | H | H |
| 60 | 2,6-difluorophenyl | CH₃ | —(CH₂)₂—O—CH₂— | —(CH₂)₂— | H | H |
| 61 | 4-trifluoromethoxyphenyl | CH₃ | —(CH₂)₂—O—CH₂— | —(CH₂)₂— | H | H |
| 62 | 2,5-dichlorothien-3-yl | CH₃ | —(CH₂)₂—O—CH₂— | —(CH₂)₂— | H | H |
| 63 | 3-methylphenyl | CH₃ | —(CH₂)₂—O—CH₂— | —(CH₂)₂— | H | H |

TABLE I-continued
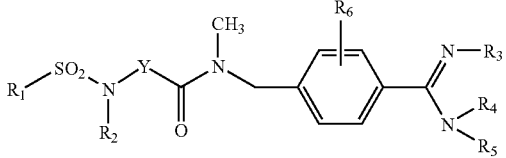
| Ex.* | R₁ | R₂ | Y | R₃ R₄ | R₅ | R₆ |
|---|---|---|---|---|---|---|
| 64 | 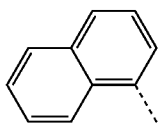 | CH₃ | —(CH₂)₂—O—CH₂— | —(CH₂)₂— | H | H |
| 65 | 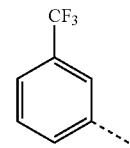 | CH₃ | —(CH₂)₂—O—CH₂— | —(CH₂)₂— | H | H |
| 66 | 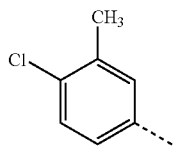 | CH₃ | —(CH₂)₂—O—CH₂— | —(CH₂)₂— | H | H |
| 67 | 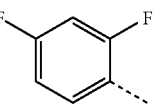 | CH₃ | —(CH₂)₂—O—CH₂— | —(CH₂)₂— | H | H |
| 68 | 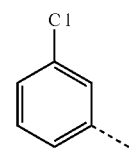 | CH₃ | —(CH₂)₂—O—CH₂— | —(CH₂)₂— | H | H |
| 69 | 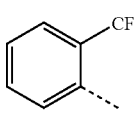 | CH₃ | —(CH₂)₄— | —(CH₂)₂— | H | H |
| 70 | 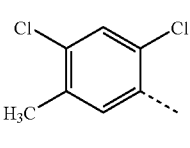 | CH₃ | —(CH₂)₄— | —(CH₂)₂— | H | H |
| 71 | 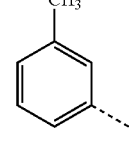 | CH₃ | —(CH₂)₄— | —(CH₂)₂— | H | H |
| 72 | 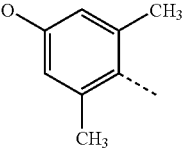 | CH₃ | —(CH₂)₄— | —(CH₂)₂— | H | H |

TABLE I-continued

| Ex.* | R₁ | R₂ | Y | R₃ | R₄ | R₅ | R₆ |
|---|---|---|---|---|---|---|---|
| 73 | 2,3,4-trichlorophenyl | CH₃ | —(CH₂)₄— | —(CH₂)₂— | | H | H |
| 74 | 2-nitrophenyl | CH₃ | —(CH₂)₄— | —(CH₂)₂— | | H | H |
| 75 | 2,4-dichlorophenyl | CH₃ | —(CH₂)₄— | —(CH₂)₂— | | H | H |
| 76 | 2-chloro-3-methylphenyl | CH₃ | —(CH₂)₄— | —(CH₂)₂— | | H | H |
| 77 | 2,6-dichloro-3-methylphenyl | CH₃ | —(CH₂)₄— | OH | H | H | H |
| 78 | 2,6-dichloro-3-methylphenyl | CH₃ | —(CH₂)₄— | H | H | H | H |
| 79 fum | 3,5-dimethyl-4-methoxyphenyl | CH₃ | —(CH₂)₂—O—CH₂— | —(CH₂)₂— | | H | H |
| 80 base | 2-trifluoromethylphenyl | CH₃ | —CH₂—CH=CH— | —(CH₂)₂— | | CH₃ | H |
| 81 fum | 2-trifluoromethylphenyl | CH₃ | —CH₂—CH=CH— | —(CH₂)₂— | | CH₃ | H |

TABLE I-continued

| Ex.* | R₁ | R₂ | Y | R₃ R₄ | R₅ | R₆ |
|---|---|---|---|---|---|---|
| 82 | 2,3-dichlorophenyl | CH₃ | —CH₂—CH=CH— | —(CH₂)₂— | H | 2-F |
| 83 | 2-chlorophenyl | CH₃ | —CH₂—CH=CH— | —(CH₂)₂— | H | 2-F |
| 84 | 4-MeO-3,5-diMe-phenyl | CH₃ | —(CH₂)₂— | —(CH₂)₂— | H | H |
| 85 base | 4-MeO-3,5-diMe-phenyl | CH₃ | —(CH₂)₄— | —(CH₂)₂— | H | 2-Cl |
| 86 fum | 4-MeO-3,5-diMe-phenyl | CH₃ | —(CH₂)₄— | —(CH₂)₂— | H | 2-Cl |
| 87 base | 2-CF₃-phenyl | CH₃ | —(CH₂)₂—O—CH₂— | —(CH₂)₂— | CH₃ | H |
| 88 fum | 2-CF₃-phenyl | CH₃ | —(CH₂)₂—O—CH₂— | —(CH₂)₂— | CH₃ | H |
| 89 | 2-chlorophenyl | CH₃ | —(CH₂)₂—O—CH₂— | —(CH₂)₂— | H | 2-Cl |
| 90 | 4-MeO-3,5-diMe-phenyl | CH₃ | —(CH₂)₂—O—CH₂— | —(CH₂)₂— | H | 2-Cl |

TABLE I-continued

Structure: R₁—SO₂—N(R₂)—Y—C(=O)—N(CH₃)—CH₂—[phenyl with R₆]—C(=N—R₃)—N(R₄)(R₅)

| Ex.* | R₁ | R₂ | Y | R₃ R₄ | R₅ | R₆ |
|---|---|---|---|---|---|---|
| 91 base | 4-MeO-2,6-diMe-phenyl | CH₃ | —(CH₂)₂—O—CH₂— | —(CH₂)₂— | iPr | H |
| 92 fum | 4-MeO-2,6-diMe-phenyl | CH₃ | —(CH₂)₂—O—CH₂— | —(CH₂)₂— | iPr | H |
| 93 base | 4-MeO-2,6-diMe-phenyl | CH₃ | —(CH₂)₂—O—CH₂— | —(CH₂)₂— | CH₃ | 2-Cl |
| 94 fum | 4-MeO-2,6-diMe-phenyl | CH₃ | —(CH₂)₂—O—CH₂— | —(CH₂)₂— | CH₃ | 2-Cl |
| 95 base | 2-CF₃-phenyl | CH₃ | —(CH₂)₂—O—CH₂— | —(CH₂)₂— | CH₃ | 2-Cl |
| 96 fum | 2-CF₃-phenyl | CH₃ | —(CH₂)₂—O—CH₂— | —(CH₂)₂— | CH₃ | 2-Cl |
| 97 base | 2-CN-phenyl | CH₃ | —(CH₂)₂—O—CH₂— | —(CH₂)₂— | CH₃ | H |
| 98 fum | 2-CN-phenyl | CH₃ | —(CH₂)₂—O—CH₂— | —(CH₂)₂— | CH₃ | H |
| 99 base | 4-MeO-2-Cl-phenyl | CH₃ | —(CH₂)₂—O—CH₂— | —(CH₂)₂— | CH₃ | H |
| 100 fum | 4-MeO-2-Cl-phenyl | CH₃ | —(CH₂)₂—O—CH₂— | —(CH₂)₂— | CH₃ | H |

TABLE I-continued

[Structure: R₁—SO₂—N(R₂)—Y—C(=O)—N(CH₃)—CH₂—(phenyl with R₆)—C(=N—R₃)(N(R₄)(R₅))]

| Ex.* | R₁ | R₂ | Y | R₃ R₄ | R₅ | R₆ |
|---|---|---|---|---|---|---|
| 101 | 2-(CF₃)phenyl | CH₃ | —(CH₂)₂— | —(CH₂)₂— | H | H |
| 102 base | 2-(CF₃)phenyl | CH₃ | —(CH₂)₂—O—CH₂— | —(CH₂)₂— | Et | H |
| 103 base | 2-(CF₃)phenyl | CH₃ | —(CH₂)₂—O—CH₂— | —(CH₂)₂— | iPr | H |
| 104 base | 3,5-dimethyl-4-MeO-phenyl | CH₃ | —(CH₂)₂—O—CH₂— | —N=CH— | H | H |
| 105 | 2-Cl-4-F-phenyl | CH₃ | —CH₂—CH=CH— | —(CH₂)₂— | H | H |
| 106 | 3,5-dichloro-4-CF₃-phenyl | CH₃ | —CH₂—CH=CH— | —(CH₂)₂— | H | H |
| 107 | 2,6-difluorophenyl | CH₃ | —CH₂—CH=CH— | —(CH₂)₂— | H | H |
| 108 | 2-NO₂-phenyl | CH₃ | —CH₂—CH=CH— | —(CH₂)₂— | H | H |
| 109 | 2,4,6-trimethylphenyl | CH₃ | —CH₂—CH=CH— | —(CH₂)₂— | H | H |
| 110 | 2,4-dichlorophenyl | CH₃ | —CH₂—CH=CH— | —(CH₂)₂— | H | H |

TABLE I-continued

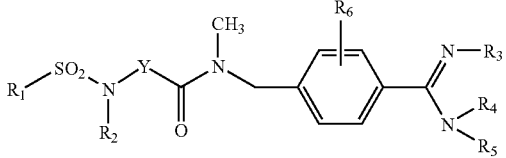

| Ex.* | R₁ | R₂ | Y | R₃ R₄ | R₅ | R₆ |
|---|---|---|---|---|---|---|
| 111 | 2,4-diCl-phenyl | $CH_3$ | —$CH_2$—CH=CH— | —$(CH_2)_2$— | H | H |
| 112 | 3-Cl-2-$CH_3$-phenyl | $CH_3$ | —$CH_2$—CH=CH— | —$(CH_2)_2$— | H | H |
| 113 | 2-CN-phenyl | $CH_3$ | —$CH_2$—CH=CH— | —$(CH_2)_2$— | H | H |
| 114 | 4-MeO-2-Cl-phenyl | $CH_3$ | —$CH_2$—CH=CH— | —$(CH_2)_2$— | H | H |
| 115 | 2,5-diCl-4-$CH_3$-phenyl | $CH_3$ | —$CH_2$—CH=CH— | —$(CH_2)_2$— | H | H |
| 116 | 2,3-diCl-phenyl | $CH_3$ | —$CH_2$—CH=CH— | —$(CH_2)_2$— | H | H |
| 117 | 4-$F_3CO$-2-Cl-phenyl | $CH_3$ | —$CH_2$—CH=CH— | —$(CH_2)_2$— | H | H |
| 118 | 4-MeO-2-$CF_3$-phenyl | $CH_3$ | —$CH_2$—CH=CH— | —$(CH_2)_2$— | H | H |
| 119 | 4-MeO-2,6-di$CH_3$-phenyl | $CH_3$ | —$CH_2$—CH=CH— | —$(CH_2)_2$— | H | H |
| 120 | 4-MeO-2-Cl-phenyl | $CH_3$ | —$(CH_2)_4$— | —$(CH_2)_2$— | H | H |

TABLE I-continued

| Ex.* | R₁ | R₂ | Y | R₃ | R₄ | R₅ | R₆ |
|---|---|---|---|---|---|---|---|
| 121 | MeO-(2-CH₃-phenyl) | CH₃ | —(CH₂)₄— | —(CH₂)₂— | | H | H |
| 122 | F₃CO-(2-CH₃-phenyl) | CH₃ | —(CH₂)₄— | —(CH₂)₂— | | H | H |
| 123 | MeO-(2-CF₃-phenyl) | CH₃ | —(CH₂)₄— | —(CH₂)₂— | | H | H |
| 124 | MeO-(2-Cl-phenyl) | CH₃ | —(CH₂)₂—O—CH₂— | —(CH₂)₂— | | H | H |
| 125 | MeO-(2-CH₃-phenyl) | CH₃ | —(CH₂)₂—O—CH₂— | —(CH₂)₂— | | H | H |

Et denotes Ethyl
cPr denotes Cyclopropyl
iPr denotes isopropyl (1-methylethyl)
Ph denotes Phenyl
*All the compounds described in the table are in salt form with trifluoroacetic acid, with the exception of the compounds marked:
(chl) salt with hydrochloric acid
(bas) non salified
(fum) salt with fumaric acid Biological Activity The compounds of the present invention were evaluated for their analgesic properties in the formalin-induced pain response test in mice (Shibata, M., Ohkubo, T., Takahashi, H. & R. Inoki. Modified formalin test: characteristic biphasic pain response. *Pain,* 38, 347-352). To summarize, formalin (0.92% in saline solution) is injected into the hind paw and the paw licking time, which reflects pain intensity, is recorded from 0 to 5 min ($1^{st}$ phase) and from 15 to 30 min ($2^{nd}$ phase) after injection. The percentage inhibition of the second formalin-induced licking phase for some compounds of the invention is given in the following table:

| Example | Dose (mg/kg) | Administration route | % inhibition of the $2^{nd}$ paw licking phase |
|---|---|---|---|
| 16 | 100 | p.o. | 80 |
| 9 | 100 | p.o. | 60 |
| 19 | 10 | i.p. | 42 |
| 49 | 1 | i.v. | 40 | p.o.: oral route
i.p.: intraperitoneal route
i.v.: intravenous route

These results demonstrate very substantial lowering of pain after administration of the compounds.

Further to the results of the preceding test, the compounds of the invention were subjected to a test intended to display their mode of action and involving the $B_1$ receptor of bradykinin.

This test uses the human umbilical vein and is conducted in acoordance with the following protocol:

Human umbilical cords 15-25 cm long are recovered just after delivery and immediately placed in a flask containing a Krebs solution of composition (in mM): 119 NaCl, 4.7 KCl, 1.18 KH$_2$PO$_4$, 1.17 MgSO$_4$, 25 NaHCO$_3$, 2.5 CaCl$_2$, 5.5 Glucose, 0.026 EDTA then stored at 4° C.

The cord is dissected in the Krebs solution to release the umbilical vein. The vein is cleansed of all adhering tissue and cut into small rings 3-4 mm in width. The endothelium is carefully removed by inserting a fine n° 1 catheter, made slightly abrasive, into the vessel lumen.

To induce the expression of the B$_1$ receptor of bradykinin, the vein segments are left to incubate at 37° C. in a 25 ml chamber for 16 hours in EMEM culture medium oxygenated by a 95% O$_2$+5% CO$_2$ mixture to which antibiotics are added: penicillin 10 000 IU/ml and streptomycin 10 000 IU/ml. The following day, the vein segments are mounted on a stainless steel support connected to an isometric sensor and placed in a 8 ml organ bath thermostatted at 37° C., containing Krebs solution oxygenated with a 95% O$_2$+5% CO$_2$ mixture.

After a rest period of one hour during which the ring segments are rinsed 5 to 6 times with the Krebs solution (maintained at 37° C. throughout all handling procedures and oxygenated with the 95% O$_2$+5% CO$_2$ mixture), the vein is gradually subjected to a 1 g load. When the load is stable, after approximately 45 minutes, the Krebs solution is replaced by a high potassium solution (KPSS: at a temperature of 37° C.) of the same composition, but containing 125 mM KCl and not NaCl.

After a series of rinsings, rest periods and load readjustments, the maximum contraction of each segment is determined by further depolarisation with the KPSS solution.

After a new rest period during which the 1 g load is constantly readjusted, the following compounds are added to the isolated organ bath: Mepyramine (1 μM), Atropine (1 μM), Indometacine (3 μM), LNA (30 μM), Captopril (10 μM), DL-Thiorphan (1 μM) and Nifedipine (0.1 μM).

After 20 minutes, the molecule to be tested or the solvent of the molecule is added to the isolated organ bath. The molecules are examined at 10 μM; if a molecule shows sufficient level of activity, it is examined at lower concentrations (e.g.: 1-0.1-0.01 μM).

After 15 minutes incubation, the vein segments are contracted through the addition of increasing concentrations of des-Arg$^{10}$-Kallidin (0.1 nM to 30 000 nM) to the chamber.

The EC$_{50}$ values (effective concentrations of agonists required to produce 50% of the maximum response obtained with the KPSS) are calculated using the least square method.

The pK$_B$=[-log K$_B$] is obtained from the equation:

$$K_B = [A]/(\text{concentration ratio}-1)$$

where [A] is the concentration of antagonist and the (concentration ratio) represents the ratio between EC$_{50}$ in the presence of antagonists, and EC$_{50}$ in the absence of antagonists.

According to this test, the compounds of the invention cited in the description show a pK$_B$ value of between 7 and 10, which tends to show that the mode of action of these compounds involves antagonism to the B$_1$ receptor of bradykinin.

The compounds of the present invention are of use in the treatment of various forms of pain such as inflammatory hyperalgesia, allodynia, neuropathic pain associated for example with diabetes, with neuropathies (constriction of sciatica nerve, lumbago) with any form of trauma, surgery (tooth extraction, tonsil removal), interstitial cystitis, inflammatory colon disease and with cancer.

The compounds of the present invention may also be used to treat any pathology associated with neutrophil migration, such as acute respiratory distress syndrome, psoriasis, chronic lung obstructions, inflammatory diseases of the colon, rheumatoid polyarthritis.

The activity of the compounds of the invention, evidenced throughout the biological tests, is indicative of analgesic properties and permits the consideration of their therapeutic use.

According to the invention, the use is advocated of the compounds defined by formula 1, and of their salts with non-toxic acids, preferably their pharmaceutically suitable salts, as active ingredients of medicinal products intended for mammals, man in particular, to treat pain or some diseases generally characterized by massive migration of neutrophils.

Among the diseases which can be treated by administering a therapeutically efficient quantity of at least one of the formula I compounds, mention may be made of inflammatory hyperalgesia, neuropathic pain, pain associated with trauma or cancer, inflammatory diseases of the colon, rheumatoid polyarthritis, psoriasis, chronic lung obstructions or acute respiratory distress syndrome.

The compounds of the invention, on account of their mode of action, also find use in the treatment or prevention of any pathological condition in which the B$_1$ receptors of bradykinin are involved and in particular are over-expressed. In addition to the various forms of pain and inflammatory diseases already cited, the compounds of the invention may be used to treat:

certain respiratory problemes such as asthma, bronchitis, pleuresy or rhinitis of allergic or viral origin, certain forms of diabetes, certain skin diseases such as dermatitis, eczema, psoriasis, eye diseases such as glaucoma, retinitis, Alzheimer's disease, septic shock, traumas, especially involving the skull, some cancers, in particular by slowing or inhibiting the proliferation of cancer cells and more particularly cancer of the prostate.

The invention also concerns a method for treating pain or the aforesaid diseases which consists of administering a therapeutically effective quantity of the formula I compound to patients in need thereof.

The dose of the active ingredient is dependent upon the mode of administration and type of pathology: it is generally between 0.05 and 10 mg/kg of the treated patient. In relation to the intended treatment, the formula I compounds or their salts may be associated with other active ingredients, and are to be formulated with routinely used excipients.

With a view to obtaining swift action, in particular when treating acute pain, the administration mode of the medicinal product is preferably by injection, for example via intramuscular or subcutaneous routes. In cases of chronic pain, the administering of the medicinal product may be made using common galenic formulations, for example by oral route in capsule or tablet form, in which a compound of the invention is associated with excipients known to persons skilled in the art, or in adhesive patch form in which a compound of the invention is formulated with excipients known to persons skilled in the art to promote the transdermal passage of the active ingredient.

The invention claimed is:

1. A compound of formula I:

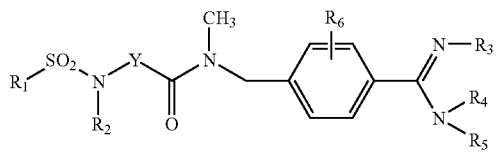

wherein:
R$_1$ is aromatic group, where said aromatic is optionally substituted by one or more atoms or groups of atoms selected from the group consisting of halogen, C$_1$-C$_3$ alkyl, C$_1$-C$_3$ alkoxy, nitro, cyano, trifluoromethyl, and trifluoromethoxy;
R$_2$ is hydrogen or C$_1$-C$_4$ alkyl, where said C$_1$-C$_4$ alkyl is optionally monosubstituted by a phenyl or —CONH$_2$ or optionally substituted by one or more fluorine atoms;
R$_3$ is hydrogen or hydroxy;
R$_4$ is hydrogen;
or R$_4$, together with R$_3$, forms a —CH=N— or a straight or branched C$_2$-C$_4$ alkylene;
R$_5$ is hydrogen or C$_1$-C$_3$ alkyl;
R$_6$ is hydrogen or halogen;
Y is straight or branched saturated C$_2$-C$_4$ alkylene or straight or branched unsaturated C$_2$-C$_4$ alkylene, where said C$_2$-C$_4$ alkylene is optionally interrupted between two carbon atoms by an oxygen atom;
or an acid addition salt thereof.

2. A compound according to claim 1,
wherein R$_1$ is chlorophenyl, dichlorophenyl, trichlorophenyl, chloro-methoxyphenyl, chloro-trifluoromethoxyphenyl, dichloro-trifluoromethyl-phenyl, chlorofluorophenyl, difluorophenyl, trifluoromethyl-phenyl, trifluoromethyl-methoxyphenyl, trifluoromethyl-chlorophenyl trifluoromethoxy-phenyl, tolyl, chlorotolyl, dichlorotolyl, dimethyltolyl, methoxytolyl, methoxymethyltolyl, dichloromethoxy, trifluoromethoxy-tolyl, naphthyl, nitrophenyl, trifluoromethyl-nitrophenyl, cyanophenyl, or thienyl.

3. A compound according to claim 1,
wherein R$_1$ is phenyl substituted by one or more atoms or groups of atoms selected from the group consisting of halogen, C$_1$-C$_3$ alkyl, and C$_1$-C$_3$ alkoxy.

4. A compound according to claim 1,
wherein R$_2$ is C$_1$-C$_4$ alkyl.

5. A compound according to claim 1,
wherein R$_2$ is hydrogen, methyl, cyclopropyl, trifluoroethyl, isopropyl, —CH$_2$CONH, —(CH$_2$)$_2$CONH, or phenethyl.

6. A compound according to claim 1,
wherein R$_3$ is hydrogen.

7. A compound according to claim 1,
wherein R$_3$ is hydroxy.

8. A compound according to claim 1,
wherein R$_4$ is hydrogen.

9. A compound according to claim 1,
wherein R$_3$ and R$_4$ together form a —N=CH— or C$_2$-C$_3$ alkylene.

10. A compound according to claim 1,
wherein R$_3$ and R$_4$ together form —N=CH—, —(CH$_2$)$_2$—, or —CH$_2$—C(CH$_3$)$_2$—.

11. A compound according to claim 1,
wherein R$_5$ is hydrogen, methyl, ethyl, or isopropyl.

12. A compound according to claim 1,
wherein R$_6$ is hydrogen, difluoro, or dichloro.

13. A compound according to claim 1,
wherein R$_5$ and R$_6$ are hydrogen.

14. A compound according to claim 1,
wherein Y is saturated C$_2$-C$_4$ alkylene or saturated C$_2$-C$_4$ alkylene interrupted by an oxygen atom.

15. A compound according to claim 1,
wherein Y is —(CH$_2$)$_2$—, —(CH$_2$)$_3$—, —(CH$_2$)$_4$—, —CH$_2$—CH=CH—, —(CH$_2$)$_2$—O—CH$_2$—, or

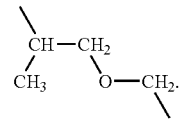

16. A compound according to claim 1,
wherein Y is —(CH$_2$)$_4$—.

17. A compound according to claim 1,
wherein Y is —(CH$_2$)$_2$—O—CH$_2$—.

18. A compound according to claim 1,
wherein said compound is:
5-[[(2,4-dichloro-3-methylphenyl)sulphonyl]methylamino]-N-[[4-(4,5-dihydro-1H-imidazol-2-yl)phenyl]methyl]-N-methyl-pentanamide;
4-[[(2,4-dichloro-3-methylphenyl)sulphonyl]methylamino]-N-[[4-(4,5-dihydro-1H-imidazol-2-yl)phenyl]methyl]-N-methyl-butanamide;
3-[[(2,4-dichloro-3-methylphenyl)sulphonyl]methylamino]-N-[[4-(4,5-dihydro-1H-imidazol-2-yl)phenyl]methyl]-N-methyl-propanamide;
4-[[(2,4-dichloro-3-methylphenyl)sulphonyl]methylamino]-N-[[4-(4,5-dihydro-1H-imidazol-2-yl)phenyl]methyl]-N-methyl-(2E)-2-butenamide;
5-[[(2-chlorophenyl)sulphonyl]methylamino]-N-[[4-(4,5-dihydro-1H-imidazol-2-yl)phenyl]methyl]-N-methyl-pentanamide;
(2E)-4-[[(2-chlorophenyl)sulphonyl]methylamino]-N-[[4-(4,5-dihydro-1H-imidazol-2-yl)phenyl]methyl]-N-methyl-2-butenamide;
3-[[(2,3-dichlorophenyl)sulphonyl]methylamino]-N-[[4-(4,5-dihydro-1H-imidazol-2-yl)phenyl]methyl]-N-methyl-propanamide;
4-[[(2,3-dichlorophenyl)sulphonyl]methylamino]-N-[[4-(4,5-dihydro-1H-imidazol-2-yl)phenyl]methyl]-N-methyl-butanamide;
5-[[(2,3-dichlorophenyl)sulphonyl]methylamino]-N-[[4-(4,5-dihydro-1H-imidazol-2-yl)phenyl]methyl]-N-methyl-pentanamide;
(2E)-4-[[(2,3-dichlorophenyl)sulphonyl]methylamino]-N-[[4-(4,5-dihydro-1H-imidazol-2-yl)phenyl]methyl]-N-methyl-2-butenamide;
5-[[(2,6-dichlorophenyl)sulphonyl]methylamino]-N-[[4-(4,5-dihydro-1H-imidazol-2-yl)phenyl]methyl]-N-methyl-pentanamide;
(2E)-4-[[(2,6-dichlorophenyl)sulphonyl]methylamino]-N-[[4-(4,5-dihydro-1H-imidazol-2-yl)phenyl]methyl]-N-methyl-2-butenamide;
5-[methyl[(1-naphthalenyl)sulphonyl]amino]-N-[[4-(4,5-dihydro-1H-imidazol-2-yl)phenyl]methyl]-N-methyl-pentanamide;
(2E)-4-[methyl[(1-naphthalenyl)sulphonyl]amino]-N-[[4-(4,5-dihydro-1H-imidazol-2-yl)phenyl]methyl]-N-methyl-2-butenamide;

5-[[(2-chlorophenyl)sulphonyl]cyclopropylamino]-N-[[4-(4,5-dihydro-1H-imidazol-2-yl)phenyl]methyl]-N-methyl-pentanamide;
5-[cyclopropyl[(2,3-dichlorophenyl)sulphonyl]amino]-N-[[4-(4,5-dihydro-1H-imidazol-2-yl)phenyl]methyl]-N-methyl-pentanamide;
5-[cyclopropyl[(2,6-dichlorophenyl)sulphonyl]amino]-N-[[4-(4,5-dihydro-1H-imidazol-2-yl)phenyl]methyl]-N-methyl-pentanamide;
5-[[(2,6-dichlorophenyl)sulphonyl](1-methylethyl)amino]-N-[[4-(4,5-dihydro-1H-imidazol-2-yl)phenyl]methyl]-N-methyl-pentanamide;
5-[(2-amino-2-oxoethyl)[(2,4-dichloro-3-methylphenyl)sulphonyl]-amino]-N-[[4-(4,5-dihydro-1H-imidazol-2-yl)phenyl]methyl]-N-methyl-pentanamide;
5-[(3-amino-3-oxopropyl)[(2,4-dichloro-3-methylphenyl)sulphonyl]-amino]-N-[[4-(4,5-dihydro-1H-imidazol-2-yl)phenyl]methyl]-N-methyl-pentanamide;
3-[[(2,3-dichlorophenyl)sulphonyl](1-methylethyl)amino]-N-[[4-(4,5-dihydro-1H-imidazol-2-yl)phenyl]methyl]-N-methyl-propanamide;
3-[[(2,6-dichlorophenyl)sulphonyl](1-methylethyl)amino]-N-[[4-(4,5-dihydro-1H-imidazol-2-yl)phenyl]methyl]-N-methyl-propanamide;
2-[2-[[(2-chlorophenyl)sulphonyl]cyclopropylamino]ethoxy]-N-[[4-(4,5-dihydro-1H-imidazol-2-yl)phenyl]methyl]-N-methyl-acetamide;
2-[2-[cyclopropyl[(2,3-dichlorophenyl)sulphonyl]amino]ethoxy]-N-[[4-(4,5-dihydro-1H-imidazol-2-yl)phenyl]methyl]-N-methyl-acetamide;
2-[2-[cyclopropyl[(2,6-dichlorophenyl)sulphonyl]amino]ethoxy]-N-[[4-(4,5-dihydro-1H-imidazol-2-yl)phenyl]methyl]-N-methyl-acetamide;
2-[2-[[(2,4-dichloro-3-methylphenyl)sulphonyl](2-phenylethyl)-amino]ethoxy]-N-[[4-(4,5-dihydro-1H-imidazol-2-yl)phenyl]methyl]-N-methyl-acetamide;
3-[[(2,6-dichlorophenyl)sulphonyl]methylamino]-N-[[4-(4,5-dihydro-1H-imidazol-2-yl)phenyl]methyl]-N-methyl-propanamide;
3-[cyclopropyl[(2,3-dichlorophenyl)sulphonyl]amino]-N-[[4-(4,5-dihydro-1H-imidazol-2-yl)phenyl]methyl]-N-methyl-propanamide;
3-[cyclopropyl[(2,6-dichlorophenyl)sulphonyl]amino]-N-[[4-(4,5-dihydro-1H-imidazol-2-yl)phenyl]methyl]-N-methyl-propanamide;
3-[(2,2,2-trifluoroethyl)[(2,3-dichlorophenyl)sulphonyl]amino]-N-[[4-(4,5-dihydro-1H-imidazol-2-yl)phenyl]methyl]-N-methyl-propanamide;
3-[(2,2,2-trifluoroethyl)[(2,6-dichlorophenyl)sulphonyl]amino]-N-[[4-(4,5-dihydro-1H-imidazol-2-yl)phenyl]methyl]-N-methyl-propanamide;
N-[[4-(4,5-dihydro-1H-imidazol-2yl)phenyl]methyl]-N-methyl-4-[methyl[[2-(trifluoromethyl)phenyl]sulphonyl]amino]-(2E)-2-butenamide;
4-[[(2,4-dichloro-3-methylphenyl)sulphonyl]amino]-N-[[4-(4,5-dihydro-1H-imidazol-2-yl)phenyl]methyl]-N-methyl-(2E)-2-butenamide;
5-[[(2,4-dichloro-3-methylphenyl)sulphonyl]methylamino]-N-[[4-(5,5-dimethyl-4,5-dihydro-1H-imidazol-2-yl)phenyl]methyl]-N-methyl-pentanamide;
5-[[(2,4-dichloro-3-methylphenyl)sulphonyl]methylamino]-N-[[4-(5,5-dimethyl-4,5-dihydro-1H-imidazol-2-yl)phenyl]methyl]-N-methyl-pentanamide;
2-[2-[[(2,3-dichlorophenyl)sulphonyl]methylamino]ethoxy]-N-methyl-N-[[4-(1,4,5,6-tetrahydro-2-pyrimidinyl)phenyl]methyl]acetamide;
2-[2-[[(2,4-dichloro-3-methylphenyl)sulphonyl]methylamino]ethoxy]-N-[[4-(4,5-dihydro-1-methyl-1H-imidazol-2-yl)phenyl]methyl]-N-methyl-acetamide;
2-[2-[[(2,3-dichlorophenyl)sulphonyl]methylamino]ethoxy]-N-[[4-(4,5-dihydro-1-methyl-1H-imidazol-2-yl)phenyl]methyl]-N-methyl-acetamide;
2-[2-[[(2,4-dichloro-3-methylphenyl)sulphonyl]methylamino]ethoxy]-N-[[4-(4,5-dihydro-1H-imidazol-2-yl)phenyl]methyl]-N-methyl-acetamide;
2-[2-[[(2,3-dichlorophenyl)sulphonyl]methylamino]ethoxy]-N-[[4-(4,5-dihydro-1H-imidazol-2-yl)phenyl]methyl]-N-methyl-acetamide;
2-[2-[[(2,6-dichlorophenyl)sulphonyl]methylamino]ethoxy]-N-[[4-(4,5-dihydro-1H-imidazol-2-yl)phenyl]methyl]-N-methyl-acetamide;
2-[2-[[(2-chlorophenyl)sulphonyl]methylamino]ethoxy]-N-[[4-(4,5-dihydro-1H-imidazol-2-yl)phenyl]methyl]-N-methyl-acetamide;
2-[2-[[(2,3-dichlorophenyl)sulphonyl]methylamino]ethoxy]-N-[[2-fluoro-4-(4,5-dihydro-1H-imidazol-2-yl)phenyl]methyl]-N-methyl-acetamide;
2-[2-[[(2,3-dichlorophenyl)sulphonyl]methylamino]propoxy]-N-[[4-(4,5-dihydro-1H-imidazol-2-yl)phenyl]methyl]-N-methyl-acetamide;
2-[2-[[(2,3-dichlorophenyl)sulphonyl]methylamino]ethoxy]-N-methyl-N-[[4-(1,4,5,6-tetrahydro-2-pyrimidinyl)phenyl]methyl]acetamide;
2-[2-[[(2,4-dichloro-3-methylphenyl)sulphonyl]methylamino]ethoxy]-N-[[4-(4,5-dihydro-1-methyl-1H-imidazol-2-yl)phenyl]methyl]-N-methyl-acetamide;
2-[2-[[(2,3-dichlorophenyl)sulphonyl]methylamino]ethoxy]-N-[[4-(4,5-dihydro-1-methyl-1H-imidazol-2-yl)phenyl]methyl]-N-methyl-acetamide;
N-[[4-(4,5-dihydro-1H-imidazol-2-yl)phenyl]methyl]-N-methyl-2-[2-[methyl[[2-(trifluoromethyl)phenyl]sulphonyl]amino]ethoxy]-acetamide;
2-[2-[[(2,4-dichlorophenyl)sulphonyl]methylamino]ethoxy]-N-[[4-(4,5-dihydro-1H-imidazol-2-yl)phenyl]methyl]-N-methyl-acetamide;
2-[2-[[(2,4-dichloro-5-methylphenyl)sulphonyl]methylamino]-ethoxy]-N-[[4-(4,5-dihydro-1H-imidazol-2-yl)phenyl]methyl]-N-methyl-acetamide;
N-[[4-(4,5-dihydro-1H-imidazol-2-yl)phenyl]methyl]-N-methyl-2-[2-[methyl[(2-nitrophenyl)sulphonyl]amino]ethoxy]acetamide;
2-[2-[[[2,6-dichloro-4-(trifluoromethyl)phenyl]sulphonyl]-methylamino]ethoxy]-N-[[4-(4,5-dihydro-1H-imidazol-2-yl)phenyl]methyl]-N-methyl-acetamide;
2-[2-[[(2-chloro-3-methylphenyl)sulphonyl]methylamino]ethoxy]-N-[[4-(4,5-dihydro-1H-imidazol-2-yl)phenyl]methyl]-N-methyl-acetamide;
2-[2-[[(2-cyanophenyl)sulphonyl]methylamino]ethoxy]-N-[[4-(4,5-dihydro-1H-imidazol-2-yl)phenyl]methyl]-N-methyl-acetamide;
N-[[4-(4,5-dihydro-1H-imidazol-2-yl)phenyl]methyl]-N-methyl-2-[2-[methyl[(2,3,4-trichlorophenyl)sulphonyl]amino]ethoxy]acetamide;
2-[2-[[(3-chloro-2-methylphenyl)sulphonyl]methylamino]ethoxy]-N-[[4-(4,5-dihydro-1H-imidazol-2-yl)phenyl]methyl]-N-methyl-acetamide;
2-[2-[[(2-chloro-4-cyanophenyl)sulphonyl]methylamino]ethoxy]-N-[[4-(4,5-dihydro-1H-imidazol-2-yl)phenyl]methyl]-N-methyl-acetamide;
N-[[4-(4,5-dihydro-1H-imidazol-2-yl)phenyl]methyl]-N-methyl-2-[2-[methyl[[2-nitro-4-(trifluoromethyl)phenyl]sulphonyl]amino]-ethoxy]acetamide;

2-[2-[[(2,6-difluorophenyl)sulphonyl]methylamino]
ethoxy]-N-[[4-(4,5-dihydro-1H-imidazol-2-yl)phenyl]
methyl]-N-methyl-acetamide;

N-[[4-(4,5-dihydro-1H-imidazol-2-yl)phenyl]methyl]-N-
methyl-2-[2-[methyl[[4-(trifluoromethoxy)phenyl]sul-
phonyl]amino]-ethoxy]acetamide;

2-[2-[[(2,5-dichlorothien-3-yl)sulphonyl]methylamino]
ethoxy]-N-[[4-(4,5-dihydro-1H-imidazol-2-yl)phenyl]
methyl]-N-methyl-acetamide;

N-[[4-(4,5-dihydro-1H-imidazol-2-yl)phenyl]methyl]-N-
methyl-2-[2-[methyl[(3-methylphenyl)sulphonyl]
amino]ethoxy]acetamide;

N-[[4-(4,5-dihydro-1H-imidazol-2-yl)phenyl]methyl]-N-
methyl-2-[2-[methyl(1-naphthalenylsulphonyl)amino]
ethoxy]acetamide;

N-[[4-(4,5-dihydro-1H-imidazol-2-yl)phenyl]methyl]-N-
methyl-2-[2-[methyl[[3-(trifluoromethyl)phenyl]sul-
phonyl]amino]-ethoxy]acetamide;

2-[2-[[(4-chloro-3-methylphenyl)sulphonyl]methy-
lamino]ethoxy]-N-[[4-(4,5-dihydro-1H-imidazol-2-yl)
phenyl]methyl]-N-methyl-acetamide;

2-[2-[[(2,4-difluorophenyl)sulphonyl]methylamino]
ethoxy]-N-[[4-(4,5-dihydro-1H-imidazol-2-yl)phenyl]
methyl]-N-methyl-acetamide;

2-[2-[[(3-chlorophenyl)sulphonyl]methylamino]ethoxy]-
N-[[4-(4,5-dihydro-1H-imidazol-2-yl)phenyl]methyl]-
N-methyl-acetamide;

N-[[4-(4,5-dihydro-1H-imidazol-2-yl)phenyl]methyl]-N-
methyl-5-[methyl[[2-(trifluoromethyl)phenyl]sulpho-
nyl]amino]pentanamide;

5-[[(2,4-dichloro-5-methylphenyl)sulphonyl]methy-
lamino]-N-[[4-(4,5-dihydro-1H-imidazol-2-yl)phenyl]
methyl]-N-methyl-pentanamide;

N-[[4-(4,5-dihydro-1H-imidazol-2-yl)phenyl]methyl-N-
methyl-5-[methyl[(3-methylphenyl)sulphonyl]amino]
pentanamide;

N-[[4-(4,5-dihydro-1H-imidazol-2-yl)phenyl]methyl]-5-
[[(4-methoxy-2,6-dimethylphenyl)sulphonyl]methy-
lamino]-N-methyl-pentanamide;

N-[[4-(4,5-dihydro-1H-imidazol-2-yl)phenyl]methyl]-N-
methyl-5-[methyl[(2,3,4-trichlorophenyl)sulphonyl]
amino]pentanamide;

N-[[4-(4,5-dihydro-1H-imidazol-2-yl)phenyl]methyl]-N-
methyl-5-[methyl[(2-nitrophenyl)sulphonyl]amino]
pentanamide;

5-[[(2,4-dichlorophenyl)sulphonyl]methylamino]-N-[[4-
(4,5-dihydro-1H-imidazol-2-yl)phenyl]methyl]-N-me-
thyl-pentanamide;

5-[[(2-chloro-3-methylphenyl)sulphonyl]methylamino]-
N-[[4-(4,5-dihydro-1H-imidazol-2-yl)phenyl]methyl]-
N-methyl-pentanamide;

N-[[4-[amino(hydroxyimino)methyl]phenyl]methyl]-5-
[[(2,4-dichloro-3-methyl)phenyl]sulphonyl]methy-
lamino]-N-methyl-pentanamide N-[[4-(aminoiminomethyl)phenyl]methyl]-5-[[(2,4-
dichloro-3-methylphenyl)sulphonyl]methylamino]-N-
methyl-pentanamide N-[[4-(4,5-dihydro-1H-imidazol-2-yl)phenyl]methyl]-2-
[2-[[(4-methoxy-2,6-dimethylphenyl)sulphonyl]me-
thylamino]ethoxy]-N-methyl-acetamide;

N-[[4-(4,5-dihydro-1-methyl-1H-imidazol-2-yl)phenyl]
methyl]-N-methyl-4-[methyl[[2-(trifluoromethyl)phe-
nyl]sulphonyl]amino]-(2E)-2-butenamide;

N-[[4-(4,5-dihydro-1-methyl-1H-imidazol-2-yl)phenyl]
methyl]-N-methyl-4-[methyl[[2-(trifluoromethyl)phe-
nyl]sulphonyl]amino]-(2E)-2-butenamide;

4-[[(2,3-dichlorophenyl)sulphonyl]methylamino]-N-[[4-
(4,5-dihydro-1H-imidazol-2-yl)-2-fluorophenyl]me-
thyl]-N-methyl-(2E)-2-butenamide;

4-[[(2-chlorophenyl)sulphonyl]methylamino]-N-[[4-(4,5-
dihydro-1H-imidazol-2-yl)-2-fluorophenyl]methyl]-N-
methyl-(2E)-2-butenamide;

N-[[4-(4,5-dihydro-1H-imidazol-2-yl)phenyl]methyl]-3-
[[(4-methoxy-2,6-dimethylphenyl)sulphonyl]methy-
lamino]-N-methyl-propanamide;

N-[[2-chloro-4-(4,5-dihydro-1H-imidazol-2-yl)phenyl]
methyl]-5-[[(4-methoxy-2,6-dimethylphenyl)sulpho-
nyl]methylamino]-N-methyl-pentanamide;

N-[[2-chloro-4-(4,5-dihydro-1H-imidazol-2-yl)phenyl]
methyl]-5-[[(4-methoxy-2,6-dimethylphenyl)sulpho-
nyl]methylamino]-N-methyl-pentanamide;

N-[[4-(4,5-dihydro-1-methyl-1H-imidazol-2-yl)phenyl]
methyl]-N-methyl-2-[2-[methyl[[2-(trifluoromethyl)
phenyl]sulphonyl]amino]-ethoxy]acetamide;

N-[[4-(4,5-dihydro-1-methyl-1H-imidazol-2-yl)phenyl]
methyl]-N-methyl-2-[2-[methyl[[2-(trifluoromethyl)
phenyl]sulphonyl]amino]-ethoxy]acetamide;

N-[[2-chloro-4-(4,5-dihydro-1H-imidazol-2-yl)phenyl]
methyl]-2-[2-[[(2-chlorophenyl)sulphonyl]methy-
lamino]ethoxy]-N-methyl-acetamide;

N-[[2-chloro-4-(4,5-dihydro-1H-imidazol-2-yl)phenyl]
methyl]-2-[2-[[(4-methoxy-2,6-dimethylphenyl)sul-
phonyl]methylamino]ethoxy]-N-methyl-acetamide;

N-[[2-chloro-4-(4,5-dihydro-1-(1-methylethyl)-1H-imidazol-2-yl)
phenyl]-methyl]-2-[2-[[(4-methoxy-2,6-dimethylphe-
nyl)sulphonyl]methyl-amino]ethoxy]-N-methyl-aceta-
mide;

N-[[2-chloro-4-(4,5-dihydro-1-methyl-1H-imidazol-2-yl)
phenyl]-methyl]-2-[2-[[(4-methoxy-2,6-dimethylphe-
nyl)sulphonyl]methyl-amino]ethoxy]-N-methyl-aceta-
mide;

N-[[2-chloro-4-(4,5-dihydro-1-methyl-1H-imidazol-2-yl)
phenyl]-methyl]-2-[2-[[(4-methoxy-2,6-dimethylphe-
nyl)sulphonyl]methyl-amino]ethoxy]-N-methyl-aceta-
mide;

N-[[2-chloro-4-(4,5-dihydro-1-methyl-1H-imidazol-2-yl)
phenyl]-methyl]-N-methyl-2-[2-[methyl[[2-(trifluo-
romethyl)phenyl]-sulphonyl]amino]ethoxy]acetamide;

N-[[2-chloro-4-(4,5-dihydro-1-methyl-1H-imidazol-2-yl)
phenyl]-methyl]-N-methyl-2-[2-[methyl[[2-(trifluo-
romethyl)phenyl]-sulphonyl]amino]ethoxy]acetamide;

2-[2-[[(2-cyanophenyl)sulphonyl]methylamino]ethoxy]-
N-[[4-(4,5-dihydro-1-methyl-1H-imidazol-2-yl)phe-
nyl]methyl]-N-methyl-acetamide;

2-[2-[[(2-cyanophenyl)sulphonyl]methylamino]ethoxy]-
N-[[4-(4,5-dihydro-1-methyl-1H-imidazol-2-yl)phe-
nyl]methyl]-N-methyl-acetamide;

2-[2-[[(2-chloro-4-methoxyphenyl)sulphonyl]methy-
lamino]ethoxy]-N-[[4-(4,5-dihydro-1-methyl-1H-imi-
dazol-2-yl)phenyl]methyl]-N-methyl-acetamide;

2-[2-[[(2-chloro-4-methoxyphenyl)sulphonyl]methy-
lamino]ethoxy]-N-[[4-(4,5-dihydro-1-methyl-1H-imi-
dazol-2-yl)phenyl]methyl]-N-methyl-acetamide;

N-[[4-(4,5-dihydro-1H-imidazol-2-yl)phenyl]methyl-N-
methyl-3-[methyl[[2-(trifluoromethyl)phenyl]sulpho-
nyl]amino]propanamide;

N-[[4-(1-ethyl-4,5-dihydro-1H-imidazol-2-yl)phenyl]
methyl]-N-methyl-2-[2-[methyl[[2-(trifluoromethyl)
phenyl]sulphonyl]-amino]ethoxy]acetamide;

N-[[4-[1-(1-methylethyl)-4,5-dihydro-1H-imidazol-2-yl]
phenyl]-methyl]-N-methyl-2-[2-[methyl[[2-(trifluo-
romethyl)phenyl]-sulphonyl]amino]ethoxy]acetamide;

N-[[4-(1H-1,2,4-triazol-5-yl)phenyl]methyl]-N-methyl-2-[2-[methyl-[(4-methoxy-2,6-dimethylphenyl)sulphonyl]amino]ethoxy]acetamide;
(2E)-4-[[(2-chloro-4-fluorophenyl)sulphonyl]methylamino]-N-[[4-(4,5-dihydro-1H-imidazol-2-yl)phenyl]methyl]-N-methyl-2-butenamide;
(2E)-4-[[[2,6-dichloro-4-(trifluoromethyl)phenyl]sulphonyl]methyl-amino]-N-[[4-(4,5-dihydro-1H-imidazol-2-yl)phenyl]methyl]-N-methyl-2-butenamide;
(2E)-4-[[(2,6-difluorophenyl)sulphonyl]methylamino]-N-[[4-(4,5-dihydro-1H-imidazol-2-yl)phenyl]methyl]-N-methyl-2-butenamide;
(2E)-4-[[(2-nitrophenyl)sulphonyl]methylamino]-N-[[4-(4,5-dihydro-1H-imidazol-2-yl)phenyl]methyl]-N-methyl-2-butenamide;
(2E)-4-[[(2,4,6-trimethylphenyl)sulphonyl]methylamino]-N-[[4-(4,5-dihydro-1H-imidazol-2-yl)phenyl]methyl]-N-methyl-2-butenamide;
(2E)-4-[[(2,5-dichlorophenyl)sulphonyl]methylamino]-N-[[4-(4,5-dihydro-1H-imidazol-2-yl)phenyl]methyl]-N-methyl-2-butenamide;
(2E)-4-[[(2,4-dichlorophenyl)sulphonyl]methylamino]-N-[[4-(4,5-dihydro-1H-imidazol-2-yl)phenyl]methyl]-N-methyl-2-butenamide;
(2E)-4-[[(3-chloro-2-methylphenyl)sulphonyl]methylamino]-N-[[4-(4,5-dihydro-1H-imidazol-2-yl)phenyl]methyl]-N-methyl-2-butenamide;
(2E)-4-[[(2-cyanophenyl)sulphonyl]methylamino]-N-[[4-(4,5-dihydro-1H-imidazol-2-yl)phenyl]methyl]-N-methyl-2-butenamide;
(2E)-4-[[(2-chloro-4-methoxyphenyl)sulphonyl]methylamino]-N-[[4-(4,5-dihydro-1H-imidazol-2-yl)phenyl]methyl]-N-methyl-2-butenamide;
(2E)-4-[[(2,4-dichloro-5-methylphenyl)sulphonyl]methylamino]-N-[[4-(4,5-dihydro-1H-imidazol-2-yl)phenyl]methyl]-N-methyl-2-butenamide;
(2E)-4-[[(2,3,4-trichlorophenyl)sulphonyl]methylamino]-N-[[4-(4,5-dihydro-1H-imidazol-2-yl)phenyl]methyl]-N-methyl-2-butenamide;
(2E)-4-[[[2-chloro-4-(trifluoromethoxy)phenyl]sulphonyl]-methylamino]-N-[[4-(4,5-dihydro-1H-imidazol-2-yl)phenyl]methyl]-N-methyl-2-butenamide;
(2E)-4-[[[4-methoxy-2-(trifluoromethyl)phenyl]sulphonyl]methyl-amino]-N-[[4-(4,5-dihydro-1H-imidazol-2-yl)phenyl]methyl]-N-methyl-2-butenamide;
(2E)-4-[[(4-methoxy-2,6-dimethylphenyl)sulphonyl]methylamino]-N-[[4-(4,5-dihydro-1H-imidazol-2-yl)phenyl]methyl]-N-methyl-2-butenamide;
5-[[(2-chloro-4-methoxyphenyl)sulphonyl]methylamino]-N-[[4-(4,5-dihydro-1H-imidazol-2-yl)phenyl]methyl]-N-methyl-pentanamide;
5-[[(4-methoxy-2-methylphenyl)sulphonyl]methylamino]-N-[[4-(4,5-dihydro-1H-imidazol-2-yl)phenyl]methyl]-N-methyl-pentanamide;
5-[[[2-methyl-4-(trifluoromethoxy)phenyl]sulphonyl]methylamino]-N-[[4-(4,5-dihydro-1H-imidazol-2-yl)phenyl]methyl]-N-methyl-pentanamide;
5-[[[4-methoxy-2-(trifluoromethyl)phenyl]sulphonyl]methylamino]-N-[[4-(4,5-dihydro-1H-imidazol-2-yl)phenyl]methyl]-N-methyl-pentanamide;
2-[2-[[(2-chloro-4-methoxyphenyl)sulphonyl]methylamino]ethoxy]-N-[[4-(4,5-dihydro-1H-imidazol-2-yl)phenyl]methyl]-N-methyl-acetamide;
2-[2-[[(4-methoxy-2-methylphenyl)sulphonyl]methylamino]ethoxy]-N-[[4-(4,5-dihydro-1H-imidazol-2-yl)phenyl]methyl]-N-methyl-acetamide.
or an acid addition salt thereof.

19. A compound according to claim 18,
wherein said acid addition salt is hydrochloride, fumarate, or trifluoroacetate.

20. A method for preparing a compound according to claim 1 or an acid addition salt thereof, comprising the steps consisting of:

a) reacting an acid of formula II:

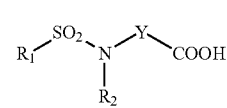

wherein
$R_1$ is aryl, where said aryl is optionally substituted by one or more atoms or groups of atoms selected from the group consisting of halogen, $C_1$-$C_3$ alkyl, $C_1$-$C_3$ alkoxy, nitro, cyano, trifluoromethyl, and trifluoromethoxy;
$R_2$ is hydrogen or $C_1$-$C_4$ alkyl, where said $C_1$-$C_4$ alkyl is optionally monosubstituted by a phenyl or —$CONH_2$ or optionally substituted by one or more fluorine atoms;
Y is straight or branched saturated $C_2$-$C_4$ alkylene or straight or branched unsaturated $C_2$-$C_4$ alkylene, where said $C_2$-$C_4$ alkylene is optionally interrupted between two carbon atoms by an oxygen atom; $R_1$ is an aromatic system that is non-substituted or substituted by one or more atoms or groups of atoms selected from the group consisting of halogen, $C_1$-$C_3$ alkyl, $C_1$-$C_3$ alkoxy, nitro, cyano, trifluoromethyl and trifluoromethoxy;
with an amine of formula III:

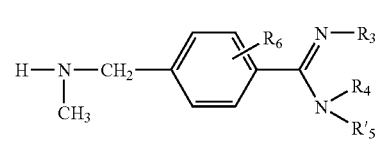

wherein
$R_3$ is hydrogen;
$R_4$ is hydrogen;
or $R_4$, together with $R_3$, forms a —CH=N— or a straight or branched $C_2$-$C_4$ alkylene;
$R'_5$ is hydrogen, $C_1$-$C_3$ alkyl, or an amino-protecting group;
$R_6$ is hydrogen or halogen;
wherein the reaction being conducted in a solvent in the presence of at least one activator agent at a temperature of room temperature to 60° C. to obtain the amide of formula:

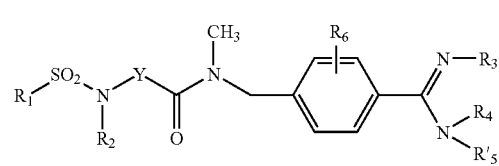

wherein $R_1$ is aryl, where said aryl is optionally substituted by one or more atoms or groups of atoms selected from the group consisting of halogen, $C_1$-$C_3$ alkyl, $C_1$-$C_3$ alkoxy, nitro, cyano, trifluoromethyl, and trifluoromethoxy;

$R_2$ is hydrogen or $C_1$-$C_4$ alkyl, where said $C_1$-$C_4$ alkyl is optionally monosubstituted by a phenyl or —$CONH_2$ or optionally substituted by one or more fluorine atoms;

$R_3$ is hydrogen;

$R_4$ is hydrogen;

or $R_4$, together with $R_3$, forms a —CH=N— or a straight or branched $C_2$-$C_4$ alkylene;

$R'_5$ is hydrogen, $C_1$-$C_3$ alkyl, or an amino-protecting group;

$R_6$ is hydrogen or halogen; and

Y is straight or branched saturated $C_2$-$C_4$ alkylene or straight or branched unsaturated $C_2$-$C_4$ alkylene, where said $C_2$-$C_4$ alkylene is optionally interrupted between two carbon atoms by an oxygen atom; $R_1$ is an aromatic system that is non-substituted or substituted by one or more atoms or groups of atoms selected from the group consisting of halogen, $C_1$-$C_3$ alkyl, $C_1$-$C_3$ alkoxy, nitro, cyano, trifluoromethyl and trifluoromethoxy;

b) if necessary, when said $R'_5$ is an amino-protecting group, reacting said compound of formula IV to remove said amino-protecting group and replace it by hydrogen, thereby obtaining said compound of formula I, where $R_5$ is hydrogen;

c) if necessary, reacting said compound of formula IV or compound of formula I with a mineral or organic acid to obtain said acid addition salt of said compound of formula IV or said compound of formula I.

21. A composition, comprising:

at least one compound according to claim 1 or an acid addition salt thereof; and at least one physiologically suitable excipient.

* * * * *